(12) United States Patent
Erasala et al.

(10) Patent No.: US 12,262,997 B2
(45) Date of Patent: Apr. 1, 2025

(54) BIOMAGNETIC DETECTION

(71) Applicant: Genetesis, Inc., Mason, OH (US)

(72) Inventors: Vineet Erasala, Mason, OH (US); Jon Von Stein, Columbus Grove, OH (US); Tatiana Sedlak, Strongsville, OH (US); Julia Prince, Toronto (CA)

(73) Assignee: Genetesis, Inc., Mason, OH (US)

( * ) Notice: Subject to any disclaimer, the term of this patent is extended or adjusted under 35 U.S.C. 154(b) by 810 days.

(21) Appl. No.: 16/636,860

(22) PCT Filed: Aug. 9, 2018

(86) PCT No.: PCT/US2018/046055
§ 371 (c)(1),
(2) Date: Feb. 5, 2020

(87) PCT Pub. No.: WO2019/032857
PCT Pub. Date: Feb. 14, 2019

(65) Prior Publication Data
US 2020/0170528 A1     Jun. 4, 2020

Related U.S. Application Data

(63) Continuation of application No. 15/673,067, filed on Aug. 9, 2017, now Pat. No. 11,134,877.

(51) Int. Cl.
*A61B 5/00*     (2006.01)
*A61B 5/05*     (2021.01)
(Continued)

(52) U.S. Cl.
CPC ............... *A61B 5/243* (2021.01); *A61B 5/05* (2013.01); *A61B 5/242* (2021.01); *G01R 33/26* (2013.01);
(Continued)

(58) Field of Classification Search
CPC .................................................... A61B 5/243
See application file for complete search history.

(56) References Cited

U.S. PATENT DOCUMENTS 4,600,886 A     7/1986    Jensen
5,122,744 A     6/1992    Koch
(Continued)

FOREIGN PATENT DOCUMENTS

CN            1259025 A     7/2000
CN            1471374 A     1/2004
(Continued)

OTHER PUBLICATIONS

A high performance compact magnetic shield for optically pumped magnetometer-based magnetoencephalography Kaiyan et al. (Year: 2019).*

(Continued)

*Primary Examiner* — Joseph M Santos Rodriguez

(57) ABSTRACT

Devices and systems as described herein is configured to sense a signal, such as a signal from an individual. In some embodiments, a signal is a magnetic field. In some embodiments, a source of a signal is an individuals organ, such as a heart muscle. A device or system, in some embodiments, comprises one or more sensors, such as an array of sensors configured to sense the signal. A device or system, in some embodiments, comprises a shield or portion thereof to reduce noise and enhance signal collection.

35 Claims, 29 Drawing Sheets

(51) Int. Cl.
*A61B 5/242* (2021.01)
*A61B 5/243* (2021.01)
*G01R 33/26* (2006.01)

(52) U.S. Cl.
CPC ... *A61B 2562/0223* (2013.01); *A61B 2562/18* (2013.01)

(56) References Cited

U.S. PATENT DOCUMENTS

| | | | |
|---|---|---|---|
| 5,697,369 A | 12/1997 | Long, Jr. et al. | |
| 5,715,821 A | 2/1998 | Faupel | |
| 5,771,894 A | 6/1998 | Richards et al. | |
| 5,785,653 A | 7/1998 | Kiyuna et al. | |
| 6,195,576 B1 | 2/2001 | John | |
| 6,230,037 B1 | 5/2001 | Tsukada et al. | |
| 6,339,328 B1 | 1/2002 | Keene et al. | |
| 6,385,479 B1 | 5/2002 | Sibbitt et al. | |
| 6,390,098 B1 | 5/2002 | LaFontaine et al. | |
| 6,522,908 B1 | 2/2003 | Miyashita et al. | |
| 6,597,940 B2 | 7/2003 | Bishop et al. | |
| 7,270,670 B1 | 9/2007 | Yencho | |
| 7,395,107 B2 | 7/2008 | Ishiyama et al. | |
| 7,599,728 B2 | 10/2009 | Feenan | |
| 7,634,360 B2 | 12/2009 | Davalos et al. | |
| 7,646,274 B2 | 1/2010 | Rapoport | |
| 7,801,591 B1 | 9/2010 | Shusterman | |
| 7,805,179 B2 | 9/2010 | Horng et al. | |
| 8,060,179 B1 | 11/2011 | Flynn | |
| 8,172,776 B2 | 5/2012 | Browne | |
| 8,310,230 B2 | 11/2012 | Haensch et al. | |
| 8,315,713 B2 | 11/2012 | Burnes et al. | |
| 8,323,188 B2 | 12/2012 | Tran | |
| 8,553,956 B2 | 10/2013 | Wu et al. | |
| 9,433,363 B1 | 9/2016 | Erasala et al. | |
| 9,788,741 B2 | 10/2017 | Erasala et al. | |
| 10,076,256 B2 | 9/2018 | Erasala et al. | |
| 10,140,421 B1 | 11/2018 | Bernard et al. | |
| 10,602,940 B1 | 3/2020 | Muchhala et al. | |
| 10,925,502 B2 | 2/2021 | Muchhala et al. | |
| 10,952,628 B2 | 3/2021 | Erasala et al. | |
| 11,134,877 B2 | 10/2021 | Erasala et al. | |
| 11,375,935 B2 | 7/2022 | Muchhala et al. | |
| 11,517,235 B2 | 12/2022 | Muchhala et al. | |
| 11,585,869 B2 | 2/2023 | Setegn et al. | |
| 2001/0029329 A1 | 10/2001 | Avrin et al. | |
| 2002/0045813 A1 | 4/2002 | Suzuki et al. | |
| 2002/0077537 A1 | 6/2002 | Avrin et al. | |
| 2002/0103428 A1 | 8/2002 | deCharms | |
| 2003/0018277 A1 | 1/2003 | He | |
| 2003/0097056 A1 | 5/2003 | Suzuki et al. | |
| 2003/0135128 A1 | 7/2003 | Suffin et al. | |
| 2003/0149354 A1 | 8/2003 | Bakharev | |
| 2004/0039291 A1 | 2/2004 | Nakai et al. | |
| 2004/0106863 A1 | 6/2004 | Seki et al. | |
| 2004/0232912 A1 | 11/2004 | Tsukamoto et al. | |
| 2004/0243022 A1 | 12/2004 | Carney et al. | |
| 2004/0254443 A1 | 12/2004 | Gott et al. | |
| 2005/0020903 A1 | 1/2005 | Krishnan et al. | |
| 2005/0096531 A1 | 5/2005 | Oonuma et al. | |
| 2005/0148844 A1 | 7/2005 | Ogata et al. | |
| 2005/0152703 A1 | 7/2005 | Ogawa | |
| 2005/0192502 A1 | 9/2005 | Ishiyama et al. | |
| 2005/0285492 A1 | 12/2005 | Hu et al. | |
| 2006/0122525 A1 | 6/2006 | Shusterman | |
| 2006/0149354 A1 | 7/2006 | Shanley et al. | |
| 2006/0234304 A1 | 10/2006 | Amann-Zalan et al. | |
| 2006/0277075 A1 | 12/2006 | Salwan | |
| 2007/0120563 A1 | 5/2007 | Kawabata et al. | |
| 2007/0167723 A1 | 7/2007 | Park et al. | |
| 2007/0167846 A1 | 7/2007 | Sternickel et al. | |
| 2007/0213600 A1 | 9/2007 | John et al. | |
| 2007/0276270 A1 | 11/2007 | Tran | |
| 2008/0033312 A1 | 2/2008 | Nakai et al. | |
| 2008/0091118 A1 | 4/2008 | Georgopoulos | |
| 2008/0108504 A1 | 5/2008 | Matsui et al. | |
| 2008/0137927 A1 | 6/2008 | Altmann et al. |
| 2008/0306359 A1 | 12/2008 | Zdeblick et al. |
| 2009/0149736 A1 | 6/2009 | Skidmore et al. |
| 2009/0172773 A1 | 7/2009 | Moore |
| 2009/0177107 A1 | 7/2009 | Guion-Johnson |
| 2009/0281413 A1 | 11/2009 | Boyden et al. |
| 2009/0295385 A1 | 12/2009 | Brazdeikis et al. |
| 2009/0295386 A1 | 12/2009 | Sato et al. |
| 2009/0299200 A1 | 12/2009 | Eggenberger et al. |
| 2010/0004708 A1 | 1/2010 | Jahns et al. |
| 2010/0036269 A1 | 2/2010 | Ferren et al. |
| 2010/0090697 A1 | 4/2010 | Savukov et al. |
| 2010/0249620 A1 | 9/2010 | Cho |
| 2011/0041520 A1 | 2/2011 | Erne et al. |
| 2011/0047105 A1 | 2/2011 | Sternickel et al. |
| 2011/0119212 A1 | 5/2011 | De Bruin et al. |
| 2011/0152703 A1 | 6/2011 | Zuckerman et al. |
| 2011/0160546 A1 | 6/2011 | Madsen |
| 2011/0224962 A1 | 9/2011 | Goldberger et al. |
| 2011/0275949 A1 | 11/2011 | Harlev et al. |
| 2011/0306896 A1 | 12/2011 | Altmann |
| 2011/0313274 A1 | 12/2011 | Subbarao |
| 2012/0197145 A1 | 8/2012 | Wu et al. |
| 2012/0219195 A1 | 8/2012 | Wu et al. |
| 2012/0239560 A1 | 9/2012 | Pourfallah et al. |
| 2012/0284332 A1 | 11/2012 | Pradeep et al. |
| 2012/0289954 A1 | 11/2012 | Lam |
| 2012/0310107 A1 | 12/2012 | Doidge et al. |
| 2013/0038325 A1 | 2/2013 | Okada |
| 2013/0057385 A1 | 3/2013 | Murakami et al. |
| 2013/0072780 A1 | 3/2013 | Espy et al. |
| 2013/0079622 A1 | 3/2013 | Wu et al. |
| 2013/0096394 A1 | 4/2013 | Gupta et al. |
| 2013/0132109 A1 | 5/2013 | Mruthyunjaya et al. |
| 2013/0184569 A1 | 7/2013 | Strommer et al. |
| 2013/0203061 A1 | 8/2013 | Kuslich et al. |
| 2013/0241929 A1 | 9/2013 | Massarwa et al. |
| 2013/0317337 A1 | 11/2013 | Wu et al. |
| 2013/0324832 A1 | 12/2013 | Wu et al. |
| 2014/0107511 A1 | 4/2014 | Banet et al. |
| 2014/0171757 A1 | 6/2014 | Kawato et al. |
| 2014/0308930 A1 | 10/2014 | Tran |
| 2014/0323848 A1 | 10/2014 | He et al. |
| 2014/0343396 A1 | 11/2014 | Sternickel et al. |
| 2014/0343397 A1 | 11/2014 | Kim et al. |
| 2014/0379269 A1 | 12/2014 | Schmitt |
| 2015/0011844 A1 | 1/2015 | Paradis |
| 2015/0011862 A1 | 1/2015 | Chaykovskyy |
| 2015/0080703 A1 | 3/2015 | Reiman |
| 2015/0150475 A1 | 6/2015 | Varcoe |
| 2015/0212166 A1 | 7/2015 | Kandori et al. |
| 2015/0366546 A1 | 12/2015 | Kamen et al. |
| 2016/0007879 A1 | 1/2016 | Gonzalez et al. |
| 2016/0044841 A1 | 2/2016 | Chamberlain |
| 2016/0066860 A1 | 3/2016 | Sternickel et al. |
| 2016/0120432 A1 | 5/2016 | Sridhar et al. |
| 2016/0131723 A1 | 5/2016 | Nagasaka |
| 2016/0135706 A1 | 5/2016 | Sullivan et al. |
| 2016/0154072 A1 | 6/2016 | Nagasaka et al. |
| 2016/0154073 A1 | 6/2016 | Nagasaka et al. |
| 2016/0287166 A1 | 10/2016 | Tran |
| 2017/0007148 A1 | 1/2017 | Kaditz et al. |
| 2017/0027498 A1 | 2/2017 | Larson et al. |
| 2017/0032922 A1 | 2/2017 | Champeaux et al. |
| 2017/0053082 A1 | 2/2017 | Pereira et al. |
| 2017/0071499 A1 | 3/2017 | Nebuya et al. |
| 2017/0135633 A1 | 5/2017 | Connor |
| 2017/0173262 A1 | 6/2017 | Veltz |
| 2017/0202509 A1 | 7/2017 | Sanderson et al. |
| 2017/0258348 A1 | 9/2017 | Erasala et al. |
| 2017/0329922 A1 | 11/2017 | Eberting et al. |
| 2017/0332918 A1 | 11/2017 | Keane |
| 2017/0352158 A1 | 12/2017 | Raina |
| 2018/0000371 A1 | 1/2018 | Gupta et al. |
| 2018/0064400 A1 | 3/2018 | Chbat et al. |
| 2018/0070841 A1 | 3/2018 | Honore et al. |
| 2018/0078146 A1 | 3/2018 | Shadforth et al. |
| 2018/0078767 A1 | 3/2018 | Rapoport et al. |
| 2018/0089531 A1 | 3/2018 | Geva et al. |

(56) References Cited

U.S. PATENT DOCUMENTS

| | | |
|---|---|---|
| 2018/0093092 A1 | 4/2018 | Howard |
| 2018/0128886 A1 | 5/2018 | Nagasaka |
| 2018/0158552 A1 | 6/2018 | Liu et al. |
| 2018/0224508 A1 | 8/2018 | Kelly et al. |
| 2018/0235470 A1 | 8/2018 | Johnson et al. |
| 2018/0236255 A1 | 8/2018 | Etkin |
| 2018/0263561 A1 | 9/2018 | Jones |
| 2018/0322351 A1 | 11/2018 | Shaker |
| 2018/0333063 A1 | 11/2018 | Muchhala et al. |
| 2018/0333104 A1 | 11/2018 | Sitek |
| 2019/0018080 A1 | 1/2019 | Marauska et al. |
| 2019/0021621 A1 | 1/2019 | Erasala et al. |
| 2019/0046059 A1 | 2/2019 | Erasala et al. |
| 2019/0108833 A1 | 4/2019 | Van Den Oord et al. |
| 2019/0117164 A1 | 4/2019 | Gupta et al. |
| 2019/0167136 A1 | 6/2019 | Kawabata et al. |
| 2019/0192021 A1 | 6/2019 | Kim et al. |
| 2019/0336231 A1 | 11/2019 | Kidd et al. |
| 2019/0365266 A1 | 12/2019 | Varcoe et al. |
| 2019/0368191 A1 | 12/2019 | Shibuya |
| 2020/0081079 A1 | 3/2020 | Khitun |
| 2020/0152330 A1 | 5/2020 | Anushiravani et al. |
| 2020/0187802 A1 | 6/2020 | Muchhala et al. |
| 2020/0211713 A1 | 7/2020 | Shadforth et al. |
| 2020/0258627 A1 | 8/2020 | Setegn et al. |
| 2020/0388287 A1 | 12/2020 | Anushiravani et al. |
| 2021/0027893 A1 | 1/2021 | Nematihosseinabadi et al. |
| 2021/0325482 A1 | 10/2021 | Setegn et al. |
| 2022/0015677 A1 | 1/2022 | Erasala et al. |
| 2023/0181077 A1 | 6/2023 | Muchhala et al. |
| 2023/0204688 A1 | 6/2023 | Setegn et al. |

FOREIGN PATENT DOCUMENTS

| | | |
|---|---|---|
| CN | 101926646 A | 12/2010 |
| CN | 102355859 A | 2/2012 |
| CN | 104188650 A | 12/2014 |
| CN | 204133457 U | 2/2015 |
| CN | 104620123 A | 5/2015 |
| CN | 113316412 A | 8/2021 |
| EP | 1302160 A1 | 4/2003 |
| EP | 3077037 A1 | 10/2016 |
| EP | 3308703 A1 | 4/2018 |
| EP | 3883457 A1 | 9/2021 |
| GB | 2179455 A | 3/1987 |
| JP | H01274498 A | 11/1989 |
| JP | H04206696 A | 7/1992 |
| JP | H04319334 A | 11/1992 |
| JP | H05317280 A | 12/1993 |
| JP | H06283888 A | 10/1994 |
| JP | H1183965 A | 3/1999 |
| JP | 2000254108 A | 9/2000 |
| JP | 2002028144 A | 1/2002 |
| JP | 2002355229 A | 12/2002 |
| JP | 2004041739 A | 2/2004 |
| JP | 2004237083 A | 8/2004 |
| JP | 2004337478 A | 12/2004 |
| JP | 2005003503 A | 1/2005 |
| JP | 2005080951 A | 3/2005 |
| JP | 2005217341 A | 8/2005 |
| JP | 2007117669 A | 5/2007 |
| JP | 2008307141 A | 12/2008 |
| JP | 2012110489 A | 6/2012 |
| JP | 2014525787 A | 10/2014 |
| JP | 2015091359 A | 5/2015 |
| JP | 2016012501 A | 1/2016 |
| JP | 2016101264 A | 6/2016 |
| JP | 2016530019 A | 9/2016 |
| KR | 20180046432 A | 5/2018 |
| WO | WO-9849938 A1 | 11/1998 |
| WO | WO-2002017769 A2 | 3/2002 |
| WO | WO-2005002313 A2 | 1/2005 |
| WO | WO-2008005513 A2 | 1/2008 |
| WO | WO-2011116229 A2 | 9/2011 |
| WO | WO-2013011515 A1 | 1/2013 |
| WO | WO-2014011940 A2 | 1/2014 |
| WO | WO-2014152110 A1 | 9/2014 |
| WO | WO-2015033244 A1 | 3/2015 |
| WO | WO-2015085011 A1 | 6/2015 |
| WO | WO-2015129756 A1 | 9/2015 |
| WO | WO-2016205731 A1 | 12/2016 |
| WO | WO-2018069287 A1 | 4/2018 |
| WO | WO-2018217655 A1 | 11/2018 |
| WO | WO-2019032857 A1 | 2/2019 |
| WO | WO-2020106284 A1 | 5/2020 |
| WO | WO-2020163593 A1 | 8/2020 |
| WO | WO-20210242868 A1 | 12/2021 |
| WO | WO-2022178314 A1 | 8/2022 |
| WO | WO-2023168392 A2 | 9/2023 |

OTHER PUBLICATIONS

European Application No. 18844754 Search Report dated Mar. 12, 2021.
PCT/US2020/017010 International Search Report and Written Opinion dated May 4, 2020.
U.S. Appl. No. 15/673,067 Final Office Action dated Oct. 13, 2020.
U.S. Appl. No. 15/673,067 Non-Final Office Action dated Feb. 5, 2021.
U.S. Appl. No. 15/673,067 Non-Final Office Action dated May 11, 2020.
U.S. Appl. No. 16/271,705 Final Office Action dated Aug. 20, 2020.
U.S. Appl. No. 16/271,705 Non-Final Office Action May 1, 2020.
International Search Report and Written Opinion for PCT/US2022/017085 issued Mar. 14, 2022.
Boussaa, et al. ECG Signals Classification Using MFCC Coefficients and ANN Classifier, 2nd International Conference on Electrical and Information Technologies ICEIT 2016.
International Application No. PCT/US18/33719 International Search Report and Written Opinion Mailed Aug. 27, 2018.
Lyons, J. Mel Frequency Cepstral Coefficient (MFCC) tutorial. Retrieved from<http://practicalcryptography.com/miscellaneous/machine-learning/guide-mel-frequency-cepstral-coefficients-mfccs/> on Jun. 6, 2017.
PCT/US2018/046055 International Preliminary Report on Patentability dated Feb. 11, 2020.
PCT/US2018/046055 International Search Report and Written Opinion dated Oct. 17, 2018.
U.S. Appl. No. 15/601,417 Non-Final Office Action Mailed Sep. 27, 2017.
U.S. Appl. No. 16/271,705 Final Office Action dated Jan. 9, 2020.
U.S. Appl. No. 16/271,705 Office Action dated Jul. 1, 2019.
PCT/US2020/017010 International Preliminary Report on Patentability dated Aug. 10, 2021.
U.S. Appl. No. 17/181,095 Final Office Action dated Sep. 29, 2021.
U.S. Appl. No. 17/181,095 Non-Final Office Action dated Jun. 3, 2021.
Mar. 29, 2022 Non-Final Office Action U.S. Appl. No. 17/181,095.
Dec. 7, 2022 Non-Final Office Action U.S. Appl. No. 17/403,029.
Amsterdam, E.A., et al., Testing of low-risk patients presenting to the emergency department with chest pain: a scientific statement from the American Heart Association, Circulation, 122(17): 1756-1776 (2010).
Arbab-Zadeh, A., Stress testing and non-invasive coronary angiography in patients with suspected coronary artery disease: time for a new paradigm, Heart Int, 7(1): e2 (2012).
CN201880048311.1 Chinese Office Action dated Mar. 8, 2022.
EP Application No. 16812571.4 94(3) Communication dated Aug. 30, 2021.
EP Application No. 18940759.6 Extended European Search Report dated Jun. 3, 2022.
EP18805647.7 Extended European Search Report dated Dec. 17, 2020.
Fenici, R., et al., Clinical validation of machine learning for automatic analysis of multichannel magnetocardiography, Proceedings of the Third International Conference on Functional Imaging

(56) References Cited

OTHER PUBLICATIONS and Modeling of the Heart (FIMH): Lecture Notes in Computer Science Book Series (LNTCS), vol. 3504: 143-152 (2005). doi:10.1007/11494621_15.
Haberkorn, W., et al., Pseudo current density maps of electrophysiological heart, nerve or brain function and their physical basis, Biomagn Res Technol, 4:5 (2006).
Heron, M., et al., Deaths: Leading Causes for 2014, Natl Vital Stat Rep, 65(5): 1-96 (2016).
JP2019-564526 Japanese Office Action dated Jan. 25, 2023.
JP2019-564526 Japanese Office Action dated Mar. 22, 2022.
Jurkko, R., et al., Non-invasive detection of conduction pathways to left atrium using magnetocardiography: validation by intra-cardiac electroanatomic mapping, Europace, 11(2): 169-177 (2009).
Killman, R., et al., Localisation of myocardial ischaemia from the magnetocardiogram using current density reconstruction method: computer simulation study, Med Biol Eng Comput, 33(5): 643-651 (1995).
Liao, Y., et al., Denoising of Magnetocardiography Based on Improved Variational Mode Decomposition and Interval Thresholding Method, Symmetry, 10(7): 269 (2018).
Moseley, M.G., et al., Emergency department observation units and the older patient, Clin Geriatr Med, 29(1): 71-89 (2013).
PCT/US2016/038209 International Preliminary Report on Patentability mailed Dec. 28, 2017.
PCT/US2016/038209 International Search Report and Written Opinion mailed Sep. 14, 2016.
PCT/US2018/033719 International Preliminary Report on Patentability mailed Nov. 26, 2019.
PCT/US2018/062113 International Search Report and Written Opinion mailed Jan. 31, 2019.
PCT/US2021/034269 International Preliminary Report on Patentability mailed Nov. 17, 2022.
PCT/US2021/034269 International Search Report and Written Opinion mailed Sep. 8, 2021.
PCT/US2022/017085 International Preliminary Report on Patentability dated Aug. 22, 2023.
PCT/US2023/063666 International Search Report and Written Opinion mailed Sep. 5, 2023.
Reinhardt, S.W., et al., Noninvasive Cardiac Testing vs Clinical Evaluation Alone in Acute Chest Pain: A Secondary Analysis of the ROMICAT-II Randomized Clinical Trial, JAMA Intern Med, 178(2): 212-219 (2018).
Tantimongcolwat, T., et al., Identification of ischemic heart disease via machine learning analysis on magnetocardiograms, Comput Biol Med, 38(7): 817-825 (2008).
U.S. Appl. No. 16/197,264 Office Action mailed Feb. 5, 2019.
U.S. Appl. No. 16/197,264 Office Action mailed Jul. 31, 2019.
U.S. Appl. No. 16/775,630 Office Action mailed Apr. 23, 2020.
U.S. Appl. No. 17/129,585 Office Action mailed Apr. 16, 2021.
U.S. Appl. No. 17/129,585 Office Action mailed Aug. 24, 2021.
U.S. Appl. No. 17/830,879 Office Action mailed Mar. 31, 2023.
U.S. Appl. No. 14/941,455 Notice of Allowance mailed Jul. 7, 2016.
U.S. Appl. No. 14/941,455 Office Action mailed Apr. 4, 2016.
U.S. Appl. No. 14/941,455 Office Action mailed Feb. 17, 2016.
U.S. Appl. No. 15/220,982 Notice of Allowance mailed May 9, 2017.
U.S. Appl. No. 15/220,982 Office Action mailed Dec. 27, 2016.
U.S. Appl. No. 15/607,053 Notice of Allowance mailed May 15, 2018.
U.S. Appl. No. 15/607,053 Office Action mailed Dec. 22, 2017.
U.S. Appl. No. 15/985,512 Notice of Allowance dated Jul. 27, 2022.
U.S. Appl. No. 15/985,512 Office Action dated Feb. 11, 2022.
U.S. Appl. No. 15/985,512 Office Action dated Feb. 12, 2021.
U.S. Appl. No. 15/985,512 Office Action dated Sep. 21, 2021.
U.S. Appl. No. 15/985,512 Office Action dated Sep. 25, 2020.
U.S. Appl. No. 16/104,528 Office Action mailed Feb. 26, 2020.
U.S. Appl. No. 16/104,528 Office Action mailed Nov. 7, 2019.
U.S. Appl. No. 17/972,889 Office Action mailed Feb. 1, 2024.
Watanabe, S., et al., Magnetocardiography in Early Detection of Electromagnetic Abnormality in Ischemic Heart Disease, J Arrhythmia, 24(1): 4-17 (2008).
Sasada, I., et al., Effective shielding for low-level magnetic fields, J Appl Phys, 64(10): 5696-5698 (1988).
U.S. Appl. No. 17/403,029 Office Action dated Oct. 6, 2023.
U.S. Appl. No. 17/403,029 Office Action mailed Jan. 29, 2024.
U.S. Appl. No. 14/941,455, filed Nov. 13, 2015, U.S. Pat. No. 9,433,363, Sep. 6, 2016, Issued.
U.S. Appl. No. 15/220,982, filed Jul. 27, 2016, U.S. Pat. No. 9,788,741, Oct. 17, 2017, Issued.
U.S. Appl. No. 15/607,053, filed May 26, 2017, U.S. Pat. No. 10,076,256, Sep. 18, 2018, Issued.
U.S. Appl. No. 16/104,528, filed Aug. 17, 2018, U.S. Pat. No. 10,952,628, Mar. 23, 2021, Issued.
U.S. Appl. No. 17/171,118, filed Feb. 9, 2021, Allowed.
U.S. Appl. No. 15/601,417, filed May 22, 2017, Abandoned.
U.S. Appl. No. 15/985,512, filed May 21, 2018, U.S. Pat. No. 11,517,235, Dec. 6, 2022, Issued.
U.S. Appl. No. 17/972,889, filed Oct. 25, 2022, Pending.
U.S. Appl. No. 15/673,067, filed Aug. 9, 2017, U.S. Pat. No. 11,134,877, Oct. 5, 2021, Issued.
U.S. Appl. No. 17/403,029, filed Aug. 16, 2021, Pending.
U.S. Appl. No. 16/197,264, filed Nov. 20, 2018, U.S. Pat. No. 10,602,940, Mar. 31, 2020, Issued.
U.S. Appl. No. 16/775,630, filed Jan. 29, 2020, U.S. Pat. No. 10,925,502, Feb. 23, 2021, Issued.
U.S. Appl. No. 17/129,585, filed Dec. 21, 2020, U.S. Pat. No. 11,375,935, Jul. 5, 2022, Issued.
U.S. Appl. No. 17/830,879, filed Jun. 2, 2022, U.S. Pat. No. 11,903,714, Feb. 20, 2021, Issued.
U.S. Appl. No. 18/411,247, filed Jan. 12, 2024, Pending.
U.S. Appl. No. 16/271,705, filed Feb. 8, 2019, Abandoned.
U.S. Appl. No. 18/084,983, filed Dec. 20, 2022, Pending.
U.S. Appl. No. 17/181,095, filed Feb. 22, 2021, U.S. Pat. No. 11,585,869, Feb. 21, 2023, Issued.
U.S. Appl. No. 17/987,232, filed Nov. 15, 2022, Pending.
U.S. Appl. No. 18/116,965, filed Mar. 3, 2023, Pending.

\* cited by examiner

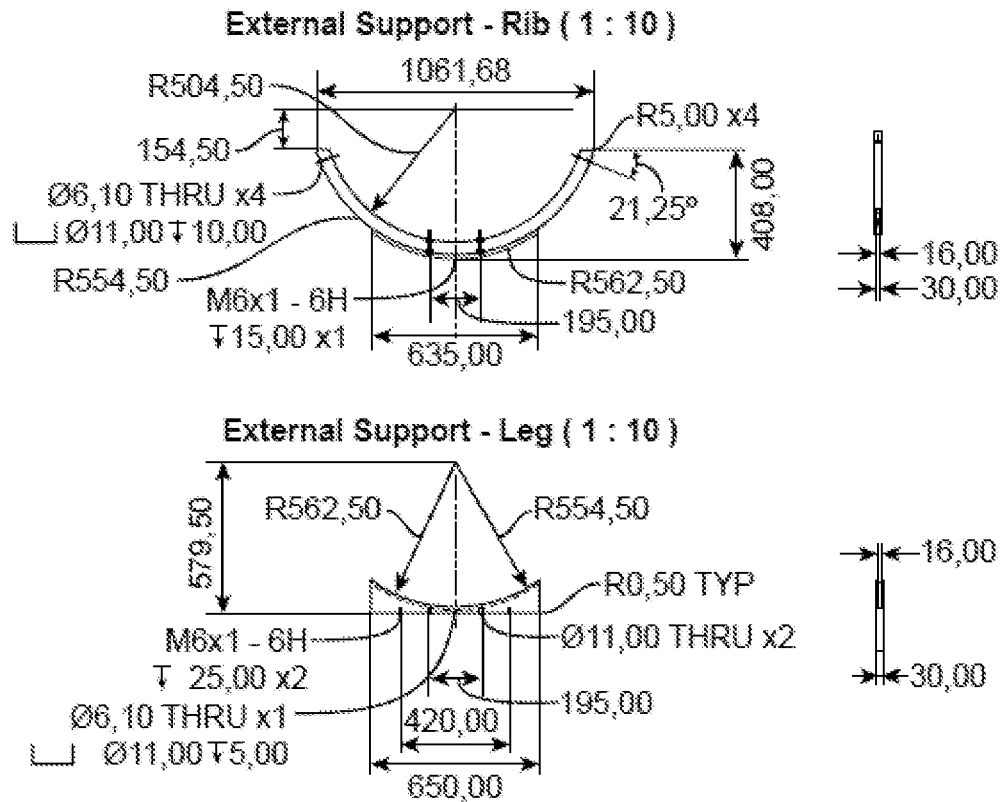
FIG. 11J
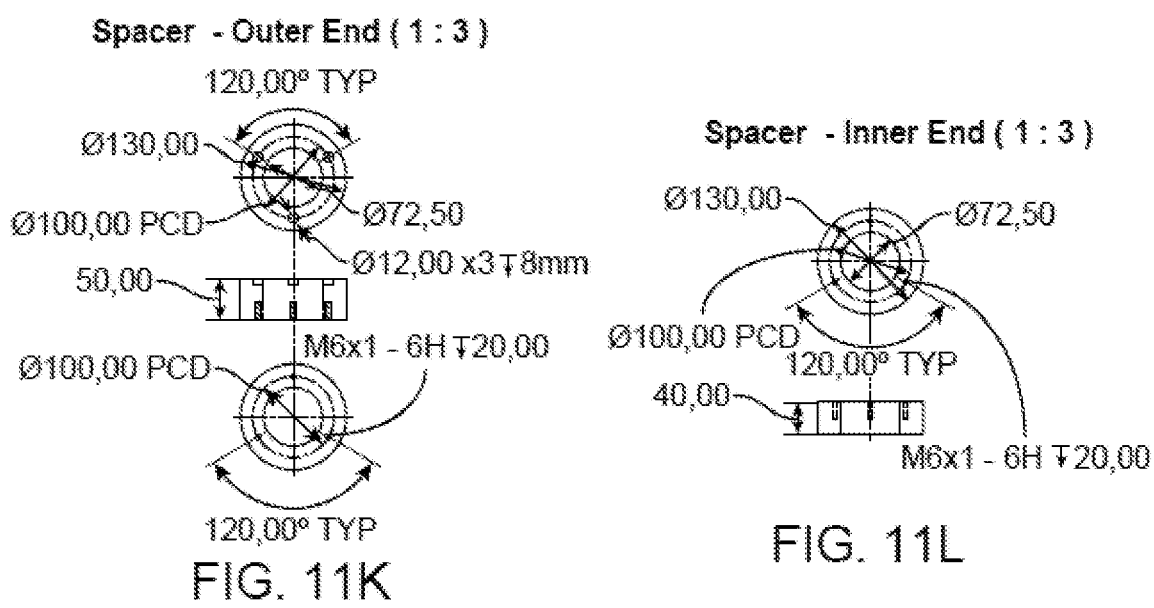
FIG. 11K
FIG. 11L

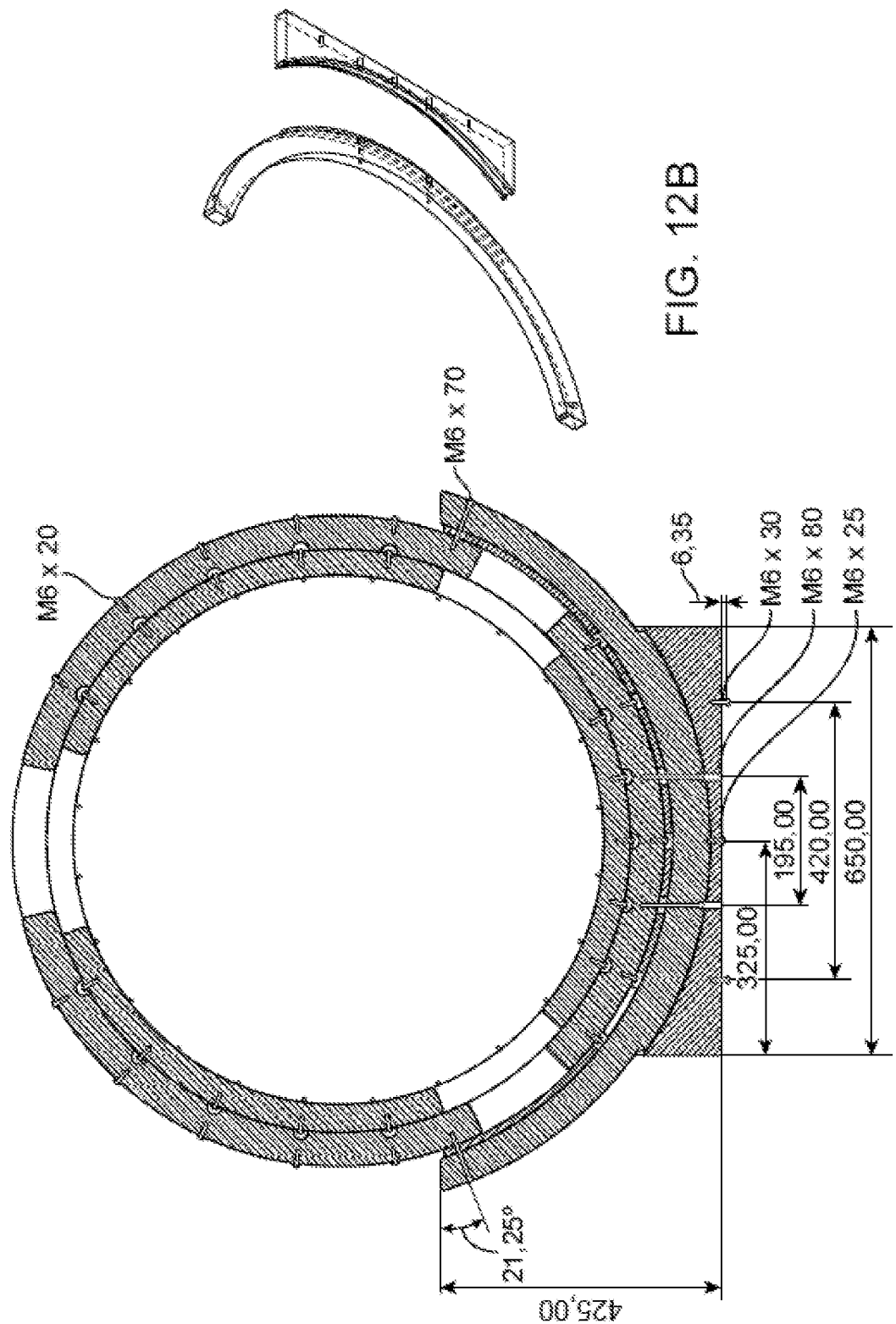

F ( 3 : 1 )

BIOMAGNETIC DETECTION

CROSS-REFERENCE

This application is a continuation-in-part of U.S. application Ser. No. 15/673,067, filed Aug. 9, 2017, which application is incorporated herein by reference.

BACKGROUND

Dynamic magnetic fields are associated with certain mammalian tissue, for example, tissue with action-potential driven physiology. Changes in the structure or function of certain tissue can be reflected in a change of the magnetic field(s) associated with and/or generated by the tissue.

SUMMARY

Described herein are systems, devices, and methods for sensing a magnetic field such as an electromagnetic field ("EMF") or a magnetocardiogram ("MCG") associated with a tissue of an individual, a portion of a body of an individual, and/or an entire body of an individual. Non-limiting examples of tissue for which a magnetic field is associated and sensed using the systems, devices, and methods described herein include blood, bone, lymph, CSF, and organs including the heart, lungs, liver, kidneys, and skin. In some embodiments, the devices and systems described herein sense a magnetic field signal associated with a portion of a body of an individual, such as, for example a torso of an individual, or a magnetic field associated with the entire body of the individual.

Described herein is a device for sensing magnetic field data associated with an individual, comprising: a movable base unit; an arm having a proximal end and a distal end, the proximal end being movably coupled to the moveable base unit so that the arm moves relative to the movable base unit with at least one degree of freedom; an array of one or more optically pumped magnetometer(s) coupled to the distal end of the arm, the optically pumped magnetometer array configured to sense the magnetic field associated with the individual. In some embodiments, the device comprises a shield configured to attenuate a magnetic field or fields associated with an environment. In some embodiments, the shield is configured to contain a portion of a body of the individual which is associated with the magnetic field data. In some embodiments, the portion of the body of the individual which is associated with the magnetic field is the chest of the individual. In some embodiments, the arm of the device or a system comprises a joint about which the arm is configured to articulate. In some embodiments, the optically pumped magnetometer array is movably coupled to the distal end so that the optically pumped magnetometer moves relative to the arm with at least one degree of freedom. In some embodiments, the optically pumped magnetometer is part of an array. In some embodiments, the array is arranged to conform to a specific portion of a body of the individual. In some embodiments, the device comprises a processor and a non-transitory computer readable media including a computer program configured to cause the processor to: receive the magnetic field data that is sensed by the optically pumped magnetometer; and filter the magnetic field data. In some embodiments, the device comprises a gradiometer wherein the computer program causes the processor to filter the data by cancelling out a magnetic field associated with an environment. In some embodiments, the computer program causes the processor to filter the data by subtracting a frequency based measurement from the magnetic field data. In some embodiments, the computer program causes the processor to generate a visual representation of the magnetic field data comprising a waveform.

Also described herein is a method for sensing magnetic field data associated with an individual, comprising: positioning a mobile electromagnetic sensing device within proximity to the individual; positioning an arm of the mobile electromagnetic sensing device that is coupled to a base unit within proximity to optically pumped magnetometer within proximity to a portion of a body of the individual associated with the magnetic field data; and sensing the magnetic field data. In some embodiments, the method comprises shielding at least a portion of the individual from a magnetic field associated with an environment. In some embodiments, the shield is configured to contain the portion of the body of the individual which is associated with the magnetic field data. In some embodiments, the portion of the body of the individual which is associated with the magnetic field is a chest of the individual. In some embodiments, the arm of the device or a system comprises a joint about which the arm is configured to articulate. In some embodiments, the optically pumped magnetometer is movably coupled to the arm so that the optically pumped magnetometer moves relative to the arm with at least one degree of freedom. In some embodiments, the optically pumped magnetometer is part of an array. In some embodiments, the array is arranged to conform to a specific portion of a body of the individual.

In some embodiments, the method comprises generating a visual representation of the magnetic field data comprising a waveform. In some embodiments, the method comprises generating a visual representation of the magnetic field data comprising a two dimensional cubic interpolation between two or more sensors in a magnetometer array for each timestamp of recorded data. In some embodiments, a visual representation includes color values that are associated with magnetic field values displayed in two dimensional (2D) space. Playback of successive visual representations of the sensed magnetic field data, in some embodiments, comprises a dynamic 2D animation summarizing electromagnetic activity detected from an individual.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 11A-L shows multiple views of one example of a shield.

FIGS. 12A-B shows multiple views of one example of external supports for a shield.

DETAILED DESCRIPTION

Figure 1:
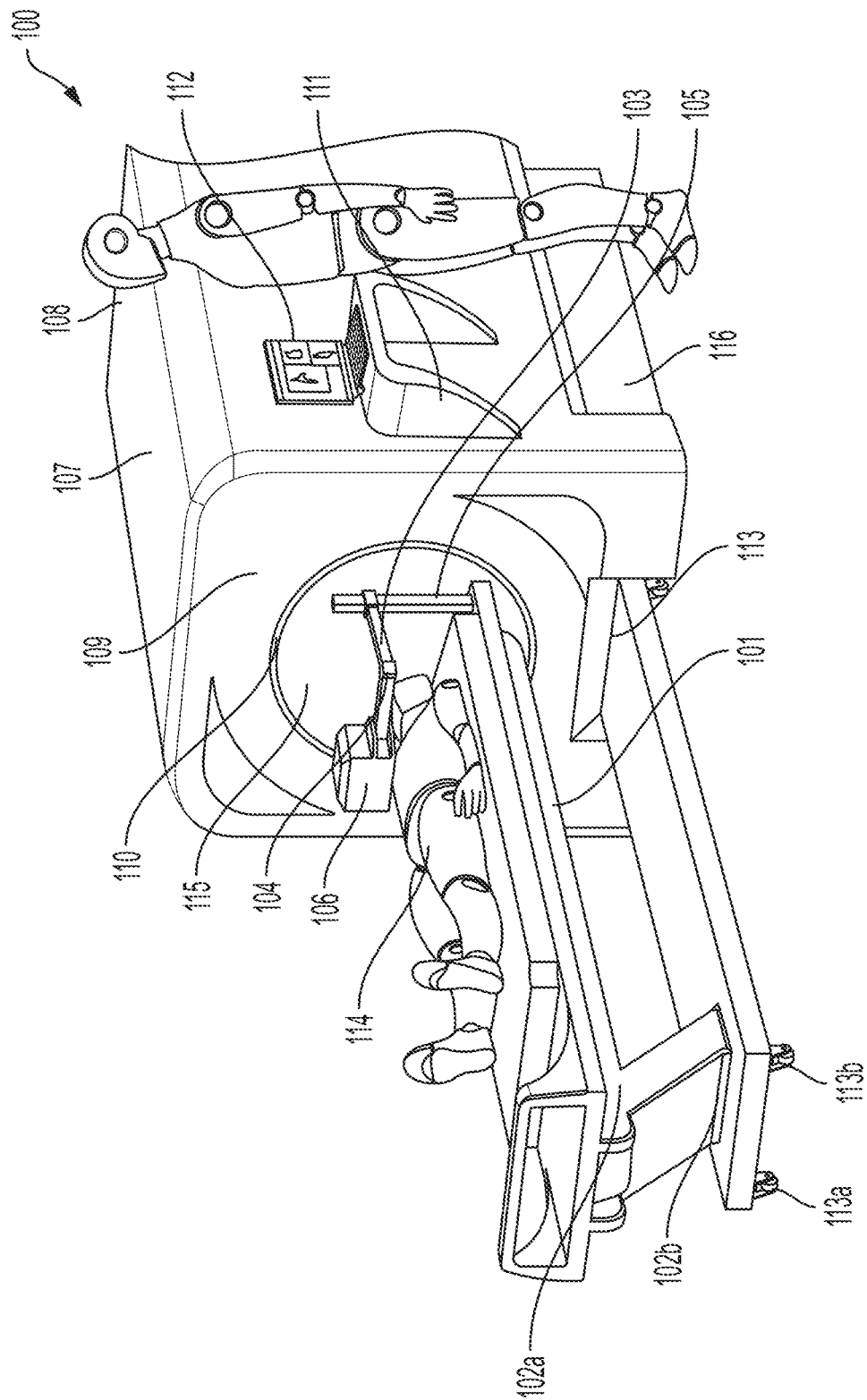
FIG. 1 shows one example of a sensor array, a shield, and a base unit.

While various embodiments are shown and described herein, it will be obvious to those skilled in the art that such embodiments are provided by way of example only. It should be understood that various alternatives to the embodiments herein are employed.

As used herein, the singular forms "a", "an", and "the" include plural references unless the context clearly dictates otherwise. Any reference to "or" herein is intended to encompass "and/or" unless otherwise stated.

As used herein, the term "about" may mean the referenced numeric indication plus or minus 15% of that referenced numeric indication.

Devices and Systems for Sensing a Magnetic Field

Described herein are devices and systems configured to sense a magnetic field associated with one or more tissues, one or more body portions, one or more organs, or an entire body of an individual. Non-limiting examples of organs and organ systems having a magnetic field that is sensed by the devices and systems described herein include the brain, heart, lungs, kidneys, liver, spleen, pancreas, esophagus, stomach, small bowel, and colon, the endocrine system, respiratory system, cardiovascular system, genitourinary system, nervous system, vascular system, lymphatic system, and digestive system. Non-limiting examples of tissue having a magnetic field that is sensed by the devices and systems described herein includes inflammatory tissue (including areas of inflamed tissue), blood vessels and blood flowing within blood vessels, lymphatic vessels and lymph flowing within lymphatic vessels, bone, and cartilage. Magnetic field data that is sensed is further processed in order to make determinations or assist a user (e.g. a healthcare provider) in making a determination about the one or more tissues, the one or more body portions, the one or more organs, or the entire body of the individual that is associated with that sensed magnetic field. For example, in some embodiments, a device as described herein is used to determine a prognosis of an individual, such as, for example, predicting a likelihood of an individual developing a disease or condition based on one or more magnetic fields that are sensed using the device. For example, in some embodiments, a device as described herein is used to determine a diagnosis, such as, for example, confirming a diagnosis or providing a diagnosis to an individual for a disease or condition based on one or more magnetic fields that are sensed using the device. For example, in some embodiments, a device as described herein is used to provide monitoring, such as monitoring a progression of a disease or condition in an individual, monitoring an effectiveness of a therapy provided to an individual, or a combination thereof based one or more magnetic fields that are sensed using the device. It should be understood that the devices and systems described herein are suitable for measuring a magnetic field associated with any type of tissue.

In some embodiments of the devices and systems described herein, sensed magnetic field data associated with a heart is used to generate a magnetocardiogram. In these embodiments of the devices and systems described herein, the devices and systems are utilized as a magnetocardiograph which is, for example, a passive, noninvasive bioelectric measurement tool intended to detect, record, and display magnetic fields that are naturally generated by electrical activity of a heart.

In some embodiments, a device or system as described herein is configured to measure one or more biomarkers in addition to a magnetic field. Non-limiting examples of biomarkers sensed in addition to a magnetic field using embodiments of the devices and systems described herein include a body temperature, a heart rate, blood pressure, an echocardiogram (ECG), a magnetic field, or any combination thereof.

In some embodiments, an individual, whose magnetic field is sensed, is in good health. In some embodiments, an individual, whose magnetic field is sensed, is an individual suspected of having a condition or disease. In some embodiments, an individual, whose magnetic field is sensed, is an individual having received a previous diagnosis of having a condition or disease.

In some embodiments, a condition or disease being identified in an individual is a cardiac condition or disease. In some embodiments, a cardiac condition or disease being identified in an individual comprises rheumatic heart disease, hypertensive heart disease, ischemic heart disease, cerebrovascular disease, inflammatory heart disease, valvular heart disease, an aneurysm, a stroke, atherosclerosis, arrhythmia, hypertension, angina, coronary artery disease, coronary heart disease, a heart attack, cardiomyopathy, pericardial disease, congenital heart disease, heart failure, or any combination thereof.

A device as described herein, in some embodiments, comprises one or more sensors. In some embodiments, two or more sensors are arranged in a sensor array. In some embodiments, a device as described herein includes an electromagnetic shield, and some embodiments of the devices described herein do not include a shield.

Systems as described herein, in some embodiments, comprise any device as described herein and one or more local and/or remote processors.

Sensors and Sensor Arrays for Sensing a Magnetic Field

In some embodiments of the devices and systems described herein, a device comprises a sensor, such as an optically pumped magnetometer (OPM) as a measurement tool, which, in some embodiments, utilizes nonradioactive self-contained alkali metal cells coupled with a closed pumping laser and photodetector setup to measure minute magnetic fields. In some embodiments of the devices and systems described herein, the devices and systems utilize OPMs in an n×n array (or grid) or alternative geometric configuration to collect magnetic field data at n discrete locations over, for example, a portion of a body of an individual such as a chest area, which, in some embodiments, is digitized using pickup electronics.

OPMs are typically configured to utilize nonradioactive self-contained alkali metal cells coupled with a closed pumping laser and photodetector setup to measure minute magnetic fields. Compared to superconducting quantum interference devices (SQUIDs), which are typically also used to detect these biomagnetic fields, OPM sensors are significantly smaller and typically do not require the use of cryogenic cooling.

The Earth's magnetic field is naturally present everywhere on Earth, and the amplitude is about 50 microtesla. OPM performance is enhanced in at least two exemplary ways in the presence of the Earth's ambient magnetic field. In a first OPM enhancing technique, a reference value representing Earth's magnetic field is used as part of a vector subtraction to isolate a signal of interest in an OPM. Another technique involves the use of a gradiometer for active noise cancellation for the OPM.

A sensor array configuration, as utilized in some embodiments of the devices and systems described herein, comprises a custom array configuration. In some embodiments, a sensor array configuration is customized to an individual's anatomy. In some embodiments, a sensor array configuration is customized to a location on the individual which is measured, such as a chest location or a head location. In some embodiments, a sensor array configuration is customized to a measurement type that a device is programmed to acquire. In some embodiments, a sensor array configuration is customized to be operatively coupled with a shield and/or an arm. In some embodiments, a sensor array configuration is interchangeable with a different array configuration — a user may perform with interchange. An array configuration, in some embodiments, comprises an arc (such as a generally curved shape) having a depth and comprising a radius from about 20 cm to about 50 cm or from about 10 cm to about 60 cm. An array configuration, such as an arc configuration, in some embodiments, comprises one or more variable inter-magnetometer distances and variable sensor densities. An array configuration, in some embodiments, comprises a concave structure (such as a concave structure configured to wrap or form around a body region, such as a head or chest). One or more magnetometers is positioned on at least a portion of a surface of the concave structure. A concave array configuration, in some embodiments, comprises one or more variable inter-magnetometer distances and variable sensor density.

In some embodiments, a sensor array n×n sensors. In some embodiments, a sensor array is a 2D rectangular array, such as a 2×2 array or a 4×4 array. In some embodiments, a sensor array is a 2D non-rectangular array, such as a 2×1 array or a 4×1 array. In some embodiments, a sensor array is a circular array or a semicircular array, such as a 3D array of sensors positioned in an arc or concave structure. In some embodiments, a sensor array is a 2D array or a 3D array. In some embodiments, a sensor of a sensor array comprises x, y, and z coordinates. An array, in some embodiments, comprises a single sensor, such as n×n=1×1. An array, in some embodiments, comprises two sensors, such as n×n=2×1. An array, in some embodiments, comprises three sensors. An array, in some embodiments, comprises four sensors. An array, in some embodiments, comprises nine sensors. An array, in some embodiments, comprises sixteen sensors. An array, in some embodiments, comprises 25 sensors. An array, in some embodiments, comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 sensors or more. In some embodiments, a sensor array comprises 8 sensors. In some embodiments, a sensor array comprises 16 sensors. In some embodiments, a sensor array comprises a single sensor housed in a single housing. In some embodiments, a sensor array comprises a plurality of sensors housed in a single housing, such as a housing having multiple sensor configurations or changeable sensor configurations. In some embodiments, a sensor array comprises a plurality of sensors housed in a plurality of housings. In some embodiments, a sensor array comprises a plurality of sensors, each sensor housed in a separate housing. In some embodiments, a first sensor and second sensor of a sensor array is different. In some embodiments, a first sensor and a second sensor of a sensor array is the same. In some embodiments, each sensor of a sensor array is unique. In some embodiments, each sensor of a sensor array is identical. In some embodiments, a subset of sensors within a sensor array is unique. In some embodiments, a subset of sensors within a sensor array is identical. Spatial positioning of a sensor in a sensor array is adjustable, such as by a user or automated by a controller. In some embodiments, spatial positioning of a sensor in a sensor array is fixed. In some embodiments, a number of sensors in a sensor array is selected based on an application. In some embodiments, a number of sensors in a sensor array is selected based on a type of measurement or a location of a measurement. An array, in some embodiments, comprises a single channel array or a multi-channel array. In some embodiments, increasing a number of sensors of a sensor array increases a resolution of a measurement taken by the array. In some embodiments, a sensor array of sensors is densely packed, such as substantially adjacent or proximal one another. An array of sensors is sparsely spaced, such as having a spacing between one another. In some embodiments, a subset of sensors of a sensor array is densely packed. In some embodiments, a subset of sensors of a sensor array is sparsely spaced or densely spaced. In some embodiments, centerpoints of any two sensors of a densely packed subset of sensors is spaced less than about: 5, 4.5, 4, 3.5, 3, 2.5, 2, 1.5, 1, 0.5, 0.1 centimeters (cm) apart. In some embodiments, centerpoints of densely packed sensors is spaced centerpoint to centerpoint from about 0.1 cm to about 2.0 cm or from about 0.1 cm to about 1.5 cm or from about 1.0 cm to about 2.0 cm. In some embodiments, centerpoints of any two sensors of a sparsely packed subset of sensors is spaced more than about: 1.5, 2, 2.5, 3, 3.5, 4, 4.5, 5, 8, 10 cm apart. In some embodiments, centerpoints of sparsely packed sensors is spaced centerpoint to centerpoint from about 1.5 cm to about 3 cm or from about 2 cm to about 5 cm or from about 2.5 cm to about 8 cm. In some embodiments, a center point is a central location of a sensor, such as a central axis. In some embodiments, a centerpoint of a circular sensor is a central point at which all other edge points are of equal distance.

In some embodiments, a densely packed array indicates intermagnetometer placement of less than 1.5 cm, while magnetometer placement of greater than about 1.5 cm constitutes a sparsely packed array.

In some embodiments, a housing is configured to house a sensor or a sensor array of sensors. In some embodiments, the housing is configured to accommodate a single configuration of sensor spacing within the housing. In some embodiments, the housing is configured to accommodate multiple configurations of sensor spacing within the housing. In some embodiments, the housing accommodates (i) adjusting sensor spacing, such as a dense spacing or a sparse spacing, or (ii) varying a number of sensors within the array. In some embodiments, a housing is a universal housing for a plurality of arrays and array configurations.

In some embodiments, a sensor is configured to sense a presence of or measure a parameter of a magnetic field. A sensor, in some embodiments, comprises a sensitivity to a magnetic field of about 10 femtotesla per root Hertz (fT/√Hz). A sensor, in some embodiments, comprises a sensitivity of from about 1 fT/√Hz to about 20 fT/√Hz. A sensor, in some embodiments, comprises a sensitivity of from about 5 fT/√Hz to about 15 fT/√Hz. A sensor, in some embodiments, comprises a sensitivity of from about 0.1 fT/√Hz to about 30 fT/√Hz. A sensor, in some embodiments, comprises a sensitivity of from about 0.5 fT/√Hz to about 12 fT/√Hz. A sensor, in some embodiments, comprises a sensitivity of from about 1 fT/√Hz to about 15 fT/√Hz. A sensor, in some embodiments, comprises a sensitivity of about: 0.001, 0.005, 0.01, 0.05, 0.1, 0.5, 1, 2, 3, 4, 5, 6, 7, 8, 10, 11, 12, 13, 14, 15, 16, 17, 18, 19, 20 fT/√Hz.

In some embodiments, a sensor does not require a cooling element, such as cryogenic cooling, to collect a measurement. In some embodiments, a sensor collects a measurement over a temperature range of from about 30 degrees Fahrenheit (F) to about 110 degrees F. In some embodiments, a sensor collects a measurement over a temperature range of from about 50 degrees F. to about 110 degrees F. In some embodiments, a sensor collects a measurement over a time period of from about 1 second to about 5 hours without a need for a cooling element. In some embodiments, a sensor collects a measurement over a time period of from about 1 second to about 1 hour without a need for a cooling element. In some embodiments, a sensor collect a measurement over a time period of from about 1 second to about 30 minutes without a need for a cooling element.

A noise source, in some embodiments, comprises a magnetic field strength. In some embodiments, a strength of a magnetic field of a noise source is measured in units of Tesla (T). Noise, such as ambient noise, in some embodiments, comprises a magnetic field strength of less than about 100 nanotesla (nT). Noise, in some embodiments, comprises a magnetic field strength of less than about 1000 nT. Noise, in some embodiments, comprises a magnetic field strength of less than about 500 nT. Noise, in some embodiments, comprises a magnetic field strength of less that about 200 nT. Noise, in some embodiments, comprises a magnetic field strength of less than about 120 nT. Noise, in some embodiments, comprises a magnetic field strength of less than about 80 nT. A noise source, such as a magnetic field of the Earth, in some embodiments, comprises magnetic field strength of about 50 microtesla (mT). Noise, in some embodiments, comprises a magnetic field strength of from about 40 mT to about 60 mT. Noise, in some embodiments, comprises a magnetic field strength of from about 10 mT to about 100 mT. Noise, in some embodiments, comprises an amplitude component, a frequency component, or a combination thereof, and, in some embodiments, comprises both sources that is direct current (DC), alternating current (AC), or a combination of the two.

Electromagnetic Shield

Some embodiments of the devices and systems as described herein are configured to provide an electromagnetic shield to reduce or eliminate the ambient magnetic field of the Earth. A shield as described herein, in some embodiments, comprises a metal alloy (e.g. permalloy or mumetal), which when annealed in a hydrogen furnace provides exceptionally high magnetic permeability, thereby isolating regions protected by the shield (e.g. within a shield shaped as a chamber) from the Earth's magnetic field.

A chamber or shield as described herein minimizes interior magnetic fields, and, in some embodiments, is constructed with one closed end and one open end. The closed end, in some embodiments, takes the form of a flat, conical, or domed endcap.

In some embodiments, utilization of a shield with sensor, such as a sensor array provides a reduction of noise such that the sensor collects a measurement that is substantially free of a noise or collects a measurement in which a noise is significantly reduced. A noise, in some embodiments, comprises a noise from a noise source. In some embodiments, a noise source includes a high frequency noise, such as greater than about 20 Hz, a middle frequency noise, such as from about 1 Hz to about 20 Hz, a low frequency noise such as from about 0.1 Hz to about 1 Hz, or any combination thereof. In some embodiments, a noise source includes any structure comprising metal. In some embodiments, a structure comprising metal includes a metal implant such as a pacemaker, a defibrillator, an orthopedic implant, a dental implant, or others. In some embodiments, a structure comprising metal includes a metal tool, a metal door, a metal chair, or others. In some embodiments, a noise source includes operation of a device such as a fan, an air conditioner, a clinical apparatus, or vibrations of a building. In some embodiments, a noise source includes operation of a power supply or an electronic device such as a computer comprising a monitor or graphical user interface.

A shield or portion thereof, in some embodiments, comprises a single layer of material. A shield or portion thereof, in some embodiments, comprises a plurality of layers of a material. A shield or portion thereof, in some embodiments, comprises a plurality of layers, wherein at least two of a plurality of layers comprise different materials. A shield or portion thereof, in some embodiments, comprises 2 layers. A shield or portion thereof, in some embodiments, comprises 3 layers. A shield or portion thereof, in some embodiments, comprises 4 layers. A shield or portion thereof, in some embodiments, comprises 5 layers. A shield or portion thereof, in some embodiments, comprises 6 layers.

A layer of a shield or portion thereof, in some embodiments, comprises a thickness from about 0.1 to about 10 millimeters. In some embodiments, a layer of a shield has a thickness from about 0.5 to about 5 millimeters. In some embodiments, a layer of a shield has a thickness from about 0.1 to about 2 millimeters. In some embodiments, a layer of a shield has a thickness from about 0.8 to about 5 millimeters. A thickness is substantially the same along a length or a circumference of a shield. In some embodiments, a thickness of a layer of a shield varies along a length or circumference of a shield.

In some embodiments, a shield comprises a plurality of layers. In some embodiments, a space is present between at least two layers of the plurality of layers. In some embodiments, a space is present between each layer of the plurality of layers. In some embodiments, a space is present between a subset of layers of the plurality of layers. In some embodiments, a first layer of a shield is configured to be adjacent a second layer of a shield. In some embodiments, a first layer of a shield is configured to be attached or bonded to a second layer of a shield. In some embodiments, a first layer of a shield is configured to be positioned from about 0.1 inches to about 5 inches from a second layer. In some embodiments, a first layer of a shield is configured to be positioned from about 1 inch to about 3 inches from a second layer. In some embodiments, a first layer of a shield is configured to be positioned from about 1 inch to about 20 inches from a second layer. In some embodiments, a first layer of a shield is configured to be positioned from about 1 inch to about 10 inches from a second layer.

In some embodiments, a length of a shield, such as an internal length or an external length, is about 2× an internal diameter of a shield. In some embodiments, a length of a shield is from about 0.5× to about 3× an internal diameter of a shield. In some embodiments, a length of a shield is from about 1× to about 3× an internal diameter of a shield. In some embodiments, a length of a shield is from about 1.5× to about 3× an internal diameter of a shield.

In some embodiments, a length of a shield is configured to accommodate at least a portion of an individual. In some embodiments, a length of a shield is configured to accommodate an individual. In some embodiments, a diameter of a shield, such as an internal diameter, is configured to accommodate at least a portion of an individual. In some embodiments, a diameter of a shield, such as an internal diameter, is configured to accommodate an individual. In some embodiments, an individual is a human subject. In some embodiments, a human subject is an adult subject, a pediatric subject, or a neonatal subject.

In some embodiments, a length of a shield is from about 40 inches to about 100 inches. In some embodiments, a length of a shield is from about 50 inches to about 90 inches. In some embodiments, a length of a shield is from about 40 inches to about 150 inches. In some embodiments, a length of a shield is from about 60 inches to about 90 inches.

In some embodiments, a diameter of a shield is from about 40 inches to about 60 inches. In some embodiments, a diameter of a shield is from about 45 inches to about 55 inches. In some embodiments, a diameter of a shield is from about 50 inches to about 70 inches.

In some embodiments, a shield or portion thereof is configured in a substantially cylindrical shape. In some embodiments, a shield or portion thereof is configured in a substantially conical shape. In some embodiments, a shield comprises a first end and a second end. In some embodiments, a first end of a shield comprises a substantially cylindrical shape and a second end of a shield comprises a conical shape. In some embodiments, a shield is configured with a first end having a cylindrical shape that is tapered, such as gradually tapered, to a second end having a conical shape.

In some embodiments, a shield comprises an internal volume configured for placing an individual, a sensor, or a combination thereof within the internal volume. When an individual is placed into an internal volume of a shield, reducing an excess of internal volume is desirable. For example, providing a shield having a tapered end or a conical end reduces an excess of internal volume, improves spatial homogeneity of a measurement taking by a sensor, reduces noise, or any combination thereof.

In some embodiments, a measurement collected from a sensor is collected from inside an internal volume of a shield. In some embodiments, a measurement is collected in the absence of an individual. In some embodiments, a measurement is collected in the presence of an individual. In some embodiments, a shield comprises a portion of an internal volume having a greater spatial homogeneity or greater amount of noise reduction as compared with a different portion. For example, a tapered end or a conical shaped end of an internal volume has greater spatial homogeneity of a measurement, a noise reduction, or both as compared to a cylindrical shaped end. In some embodiments, an individual is positioned within an internal volume of a shield such that an area of the subject desired to be measured by the sensor is positioned within a portion of the internal volume having greater spatial homogeneity of a measurement, a reduction in noise, or both.

In some embodiments, altering a length of a shield, altering a diameter of a shield, altering a shape of a shield (such as a tapering) alters noise reduction and quality of a measurement within an internal volume of a shield. Each is independently altered or collectively altered to optimize noise reduction or improve quality of a measurement taken by a sensor.

In some embodiments, a shield comprises a coil, such as a Helmholtz coil. In some embodiments, a coil generates a current within the coil. In some embodiments, addition of a coil to a shield improves a quality of a measurement (such as a spatial homogeneity of a measurement), reduces a noise, or a combination thereof In some embodiments, a shield comprises a plurality of coils. A shield, in some embodiments, comprises a single coil. A shield, in some embodiments, comprises two coils. A shield, in some embodiments, comprises three coils. A shield, in some embodiments, comprises from 1 to 3 coils. In some embodiments, a coil is positioned within a portion of a shield. In some embodiments, a coil is positioned within a portion of a shield that a measurement occurs. In some embodiments, a position of a coil is adjustable, such as by a controller or by a user. In some embodiments, a position of a coil is adjusted for each measurement of a sensor. In some embodiments, a position of a coil is pre-programed accordingly to a type of measurement of a sensor. In some embodiments, a position of a coil is adjustable with an accuracy of from about 0.1 inches to about 5 inches. In some embodiments, a coil provides feedback to a user or to a controller that a desired positioned is achieved by the coil. In some embodiments, a feedback from a coil to a user or to a controller occurs prior to a measurement, during a measurement, or after a measurement of a sensor. In some embodiments, a feedback from a coil confirms that a desired position (such as a position corresponding to a position of an individual desired to be measured) is reached.

In some embodiments, a shield is modular. In some embodiments, a shield or portion thereof is disposable. In some embodiments, a shield is configured to accept at least a portion of an individual, at least a portion of a sensor array, or a combination thereof. A portion of an individual, in some embodiments, comprises a head, an arm, or a leg that is placed into an inner volume of a shield. A portion of an individual, in some embodiments, comprises an individual from a mid-section to a head or from a mid-section to a foot.

In some embodiments, a shield is not modular. In some embodiments, a shield is configured to interact with one or more modular units. For example, a modular unit, such as base unit, is modular and configured to modulate in relation to a shield that is stationary or non-modular.

In some embodiments, a shield or portion thereof is configured for subject comfort. In some embodiments, a shield or portion thereof is configured with lighting, such as an internal volume of a shield, in some embodiments, comprises a lighting source. In some embodiments, a shield or portion thereof is configured with venting, such as one or more ports or openings, such as one or more openings positioned on an internal surface of a shield.

A shield, in some embodiments, comprises a single material. A shield, in some embodiments, comprises more than one material. A shield or a portion thereof, in some embodiments, comprises a metal, a metal alloy, or a combination thereof. A shield or a portion thereof, in some embodiments, comprises a permalloy or a mumetal. A shield or a portion thereof, in some embodiments, comprises aluminum, copper, gold, iron, nickel, platinum, silver, tin, zinc, or any combination thereof. A shield or a portion thereof, in some embodiments, comprises brass, bronze, steel, chromoly, stainless steel, titanium, or any combination thereof.

A shield or a portion thereof, in some embodiments, comprises nickel, iron, or a combination thereof. In some embodiments, a shield or portion thereof comprises from about 70% to about 90% by weight of nickel. In some embodiments, a shield or portion thereof comprises from about 75% to about 85% by weight of nickel. In some embodiments, a shield or portion thereof comprises from about 10% to about 30% by weight of iron. In some embodiments, a shield or portion thereof comprises from about 15% to about 25% by weight of iron. In some embodiments, a shield or portion thereof comprises from about 70% to about 90% by weight of nickel and from about 10% to about 30% by weight of iron. In some embodiments, a shield or portion thereof comprises from about 40% to about 60% by weight nickel and about 50% to about 60% by weight of iron. In some embodiments, a shield or portion thereof comprising a permalloy or a mumetal also comprises one or more additional elements such as molybdenum.

A shield or portion thereof, in some embodiments, comprises a material having a high permeability. For example, a material , in some embodiments, comprises a relative permeability of from about 50,000 to about 900,000 as compared to for example steel having a relative permeability of from about 4,000 to about 12,000. A material, in some embodiments, comprises a relative permeability of from about 75,000 to about 125,000. A material, in some embodiments, comprises a relative permeability of from about 400,000 to about 800,000. A material, in some embodiments, comprises a relative permeability of greater than about 50,000. A material, in some embodiments, comprises a relative permeability of greater than about 75,000. A material, in some embodiments, comprises a relative permeability of greater than about 100,000. A material, in some embodiments, comprises a relative permeability of greater than about 200,000. A material, in some embodiments, comprises a relative permeability of greater than about 300,000. A material, in some embodiments, comprises a relative permeability of greater than about 400,000. A material, in some embodiments, comprises a relative permeability of greater than about 500,000. A material, in some embodiments, comprises a relative permeability of greater than about 600,000. A material, in some embodiments, comprises a relative permeability from about 80,000 to about 900,000. A material, in some embodiments, comprises a relative permeability from about 400,000 to about 800,000.

In some embodiments, a shield is monolith in form. In some embodiments, a shield is formed of a plurality of subcomponents configured together. In some embodiments, a shield is 3D printed. A shield, in some embodiments, comprises a material formed in a hydrogen furnace, such as a shield comprising one or more materials annealed in a hydrogen furnace.

Described herein are devices and systems configured to sense a magnetic field associated with, for example, a tissue, a body part, or an organ of an individual. In some embodiments of the devices and systems described herein, a device for sensing a magnetic field comprises a mobile base unit and one or more magnetic field sensors. In some embodiments of the devices and systems described herein, a device for sensing a magnetic field comprises a mobile base unit, one or more magnetic field sensors, and a shield for shielding ambient electromagnetic noise.

In some embodiments of the devices and systems described herein, a device for sensing a magnetic field comprises a mobile base unit that is configured for portability. In some embodiments, a mobile base unit includes wheels or a track upon which the mobile base unit is moved on a surface. In some embodiments, a mobile base unit is hand-held. A mobile base unit is configured, in some embodiments, to comprise a housing containing electronic components.

In some embodiments of the devices and systems described herein, a device for sensing a magnetic field comprises one or more magnetic field sensors such as, for example, one or more OPMs.

In some embodiments of the devices and systems described herein, a device for sensing a magnetic field comprises one or more coupling mechanisms for receiving and coupling with one or more sensors. In some embodiments of the systems and devices described herein, a device for sensing a magnetic field coupler comprises one or more arms or extensions that connect with the mobile base unit. In some embodiments of the devices and systems described herein, a device for sensing a magnetic field includes one or more extensions or arms configured to move, rotate, and/or articulate so as to position one or more sensors for sensing a magnetic field within proximity to an individual whose magnetic field is to be sensed.

In some embodiments, a device or system as described herein comprises a mechanical housing that comprises one or more nonferrous materials, such as, for example, an aluminum alloy, a rubber, a plastic, a wood or any combination thereof to minimize an amount of interference seen in a biomagnetic signal from a device or system itself.

Exemplary Embodiments

FIG. 1 shows an exemplary embodiment of a device for sensing a magnetic field 100 as described herein comprising a shield 107. A device for sensing a magnetic field 100 comprises a shield 107 and one or more sensors 106 (such as an optically pumped magnetometer). In some embodiments, two or more sensors 106 are arranged in an array.

A shield 107 comprises an open end 109 and a closed end 108. In some embodiments, the open end 109 is positioned adjacent to the closed end 108. In some embodiments, the open end 109 is positioned opposite to the closed end 108. A shield 107, in some embodiments, comprises one or more openings. One or more openings of the shield 107 are configured to receive at least a portion of a base unit 101, at least a portion of an individual 114, at least a portion of the one or more sensors 106, or any combination thereof.

For example, a shield 107 comprises an opening, such as a recess opening 113 configured to receive a portion of a base unit 101. A shield 107, in some embodiments, comprises an opening 115 configured to receive at least a portion of a base unit 101, at least a portion of an individual 114, at least a portion of one or more sensors 106, or any combination thereof. A shield 107 comprises an inner surface 110. In some embodiments, an inner surface 110, which, in some embodiments, comprises a coating. In some embodiments, an inner surface 110 of a shield 107 defines an inner volume of a shield. An inner volume of a shield 107 is a volume into which a portion of an individual 114, a portion of a sensor, a portion of a base unit 101, or any combination thereof is received. A shield 107 comprises a shield portion 116 configured to store a component of a device for sensing a magnetic field, such as an electronic driver. A shield portion 116, in some embodiments, comprises a drawer, a shelf, a cabinet, a compartment, or a section of a shield 107. A shield portion 116, in some embodiments, is positioned on a side portion of a shield. A shield portion 116, in some embodiments, is positioned on a bottom of a shield 107.

In some embodiments, a device for sensing a magnetic field 100 as described herein comprises a base unit 101. In the exemplary embodiment shown in FIG. 1, a base unit 101 comprises a bed or gurney on which an individual 114 lies.

In some embodiments, a device for sensing a magnetic field 100 as described herein is operatively coupled with a base unit 101. In some embodiments, a shield 107 is configured to receive a portion of a base unit 101. For example, a recess opening of a shield 107 is, in some embodiments, configured to receive at least a portion of a base unit 101, as shown in FIG. 1. In some embodiments, a base unit 101 is directly attachable to one or more sensors 106.

A base unit 101, in some embodiments, is configured as a stationary base unit 101. A base unit 101, in some embodiments, is configured as a mobile base unit 101. In some embodiments, a shield 107 is movable relative to a base unit 101. In some embodiments, a base unit 101 is movable relative to a shield 107. In some embodiments, a base unit 101 and a shield 107 are movable relative to one another.

In the exemplary embodiment shown in FIG. 1, a base unit 101 is configured as a movable base unit 101, A movable base unit 101, in some embodiments, is configured to move in one or more degrees of freedom (e.g. relative to a shield 107). In some embodiments, a movable base unit 101 is configured to move along an x axis, a y axis, a z axis, or any combination thereof. A movable base unit 101, in some embodiments, comprises one or more rotating elements such as a wheel (113a, 113b), a roller, a conveyor belt, or any combination thereof configured to provide movement of a base unit 101 or a portion thereof. In some embodiments, a base unit 101 comprises one rotating element. In some embodiments, a base unit 101 comprises two rotating elements. In some embodiments, a base unit 101 comprises three rotating elements. In some embodiments, a base unit 101 comprises four rotating elements. In some embodiments, a base unit 101 comprises more than four rotating elements. In some embodiments, a rotating element is positioned at one or both ends of a base unit 101. In some embodiments, a base unit 101 comprises a non-rotating element configured to be received into a track or channel such that the base unit 101 is movable along the track or channel. In some embodiments, the track or channel is positioned adjacent thereto a shield 107, such that the base unit 101 is movable towards, away, or both from the shield along the track or channel.

A base unit 101, in some embodiments, comprises one or more pivots (102a, 102b). In some embodiments, a base unit 101 comprises one pivot. In some embodiments, a base unit 101 comprises two pivots. In some embodiments, a base unit 101 comprises more than two pivots. A pivot 102a, 102b, in some embodiments, is configured to permit movement of a base unit 101 such as by accommodating an individual being positioned onto a base unit 101. A pivot 102a, 102b, in some embodiments, is configured to permit movement of a base unit 101 such as to position the base unit 101 within an inner volume of a shield 107. A pivot 102a, 102b, in some embodiments, is configured to provide movement to the base unit 101, providing one or more degrees of freedom.

In some embodiments, one or more sensors 106 are operatively coupled to an arm 103. An arm 103, in some embodiments, is a movable arm 103. In some embodiments, the device has an extensible arm 103, at the end of which, a sensor array 106 is housed. In some embodiments, any type of OPM is used as one or more of the one or more sensors 106. In some embodiments, an arm 103 is movable in at least one degree of freedom. An arm 103, in some embodiments, comprises a joint 104 configured to provide movement to the arm 103. In some embodiments, an arm 103 comprises more than one joint 104. In some embodiments, an arm 103 comprises two joints 104. An arm 103, in some embodiments, is operatively coupled one or more sensors 106 and to a base unit 101, such as shown in FIG. 1. An arm 103, as shown in FIG. 1, is operatively coupled to a base unit 101 by a beam 105.

In some embodiments, a device for sensing a magnetic field 100 as described herein comprises a computer processor 112, as shown in FIG. 1. A computer processor 112, in some embodiments, comprises a graphical user interface. A computer processor 112, in some embodiments, comprises a touchscreen.

A device for sensing a magnetic field 100, as shown in FIG. 1, comprises a stand 111 configured to, for example, receive a computer processor 112. A stand 111, in some embodiments, is positioned adjacent to a shield 107 or a base unit 101 of a device for sensing a magnetic field 100. A stand 111, in some embodiments, is integral to or attachable to a shield 107 or a base unit 101 of a device for sensing a magnetic field 100.

In some embodiments of the device 100 shown in FIG. 1, the device is essentially stationary. It should be understood that other embodiments of the device 100 (and systems) described herein are configured to be mobile.

In some embodiments, the device 100 includes a compartment 116 or a tabletop to house electronics, a computer interface, and a power supply, and in others it includes a separate unit to house these components, connected to the first component by wiring. In some embodiments, the device 100 requires a power supply via an electrical outlet. In some embodiments, standard operating procedure include extending a device's arm 103 and lowering a base of a sensor unit 106 to a position, such as a position that is within 2 centimeters adjacent a skin surface of an individual (such as an individual's 114 chest, head, or other region of interest). The device 100, in some embodiments, is calibrated using a software application that is provided with the device or provided separately. In some embodiments, a biomagnetic signal of interest is displayed and recorded for immediate or later analysis.

Operation of a device (or system) 100 as described herein, in some embodiments, is controlled using either a software User Interface (UI) or manual UI or a combination UI including software and manual elements. In some embodiments, a UI is installed on site, on a provided accessory computer. The use of the device is prescribed by a medical professional such as a physician to determine more information regarding an individual's condition. Within the UI, User preferences and acquisition parameters are chosen, including a sampling rate and an axis operation of the device or system. From the software user interface, magnetic field signals from an individual, such as signals corresponding to an individual's heart, is displayed and saved to a file. In some embodiments, the device or system is configured to measure cardiac electrical activity, creating waveforms similar to electrocardiograph recordings which may demonstrate points of interest in a cardiac cycle.

One or more sensors 106 are arranged in an array wherein one or more optically pumped magnetometers outputs one or more waveforms. An array, in some embodiments, outputs one waveform per sensor of the array. In some embodiments, individual waveforms of individual sensors are combined into a single waveform. An array, in some embodiments, outputs a single waveform which comprises a combination of waveforms from each sensor of the array. In some embodiments, magnetic field data is visualized as a series of 2D images made from interpolated magnetic field values between sensors. In some embodiments, an array comprises at least one OPM and at least one other type of magnetomitor. In some embodiments, an array comprises only OPMs.

The shield 107, in some embodiments, is housed in a shrouded structure, and the total device length, in some embodiments, is at minimum of about 2.25 meters (m) in length, with a bore opening (or an internal opening diameter) of about 0.8 m.

In some embodiments, in order to insert an individual into a shield 107, a base unit 101 such as a bed platform is used upon which the subject is positioned. During device use, a flexible jointed arm 103 with x-y-z translational movement is configured to occupy any point within a semicircle defined by total arm length at extension is used to position an array of n-optically pumped magnetometers in a wide range of geometries on or proximally above a portion of an individual (such as an individual's 114 chest, head, or other organ) using a set standard operating procedure based on an organ of interest, a condition or disease of interest, or a combination thereof. In some embodiments, after this point, the sensor array is turned on and at least a portion of the subject, at least a portion of the base unit 101 (e.g. bed platform), or a combination thereof is slid into the shield 107. Using a provided computer application, fast calibration of the sensors occurs, and then the magnetic field of the organ of interest is displayed, and recorded, or a combination thereof for immediate or later analysis. In some embodiments, electronic drivers for the sensors are housed either underneath the shield 107 portion of the device 100, or are housed in an adjacent cart with computer control.

The system, in some embodiments, comprises a touch screen computer interface (such as a graphical user interface) housed on a side of the device itself, or on said adjacent cart.

Figure 2:
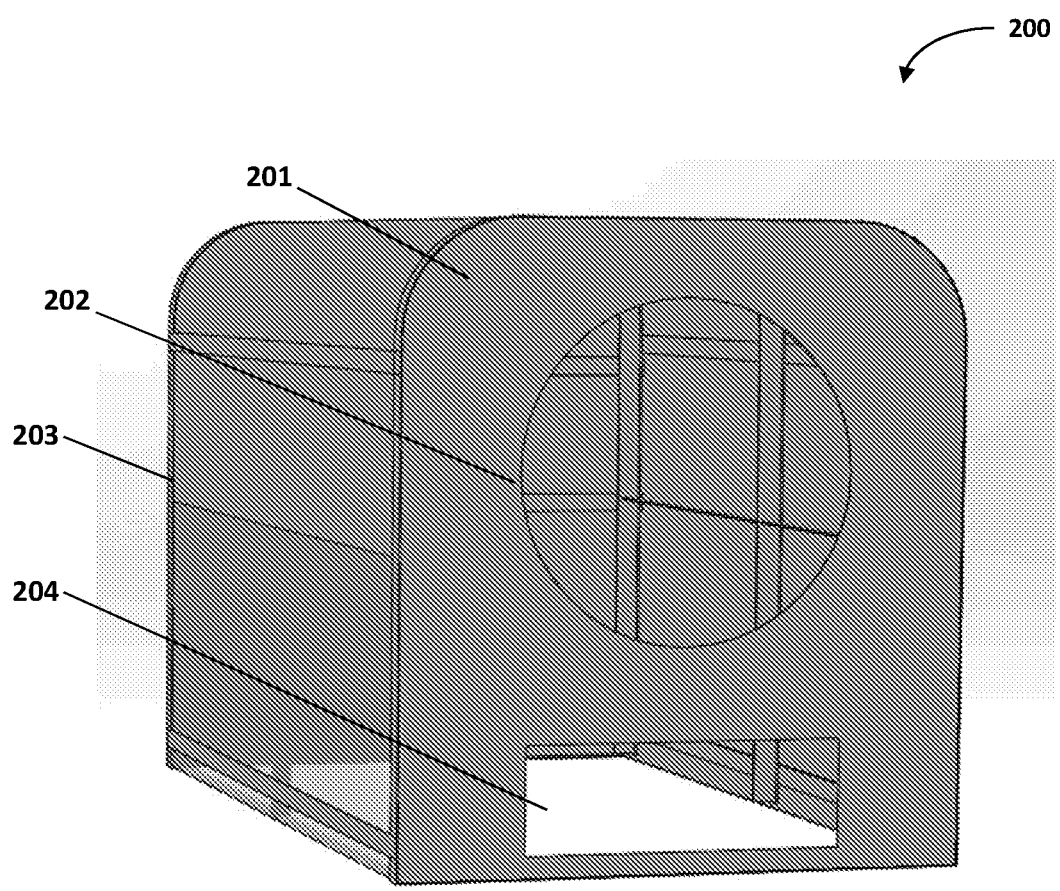
FIG. 2 shows one example of a shield.

As shown in FIG. 2, a shield, in some embodiments, comprises a shield frame 200. A shield frame 200, in some embodiments, provides a macrostructure or shape for the shield. In some embodiments, a shield frame 200 is positioned at an inner surface or an outer surface of the shield. In some embodiments, a shield frame 200 is configured to receive one or more portions of a base unit. In some embodiments, a shield frame 200 comprises an open end 201 and a closed end 203. In some embodiments, an opening 202 is positioned on the open end 201, such as an opening configured to receive a portion of a base unit. In some embodiments, an opening, such as a recess opening 204, is positioned on the open end 201 or a closed end 203, and is configured to receive a portion of a base unit. In some embodiments, a shield frame 200 comprises individual elements operatively connected to form the shield frame 200 or the shield frame 200, in some embodiments, comprises a single monolith frame or 3D printed frame. In some embodiments, a shield frame 200 comprises one or more layers.

Figure 3:
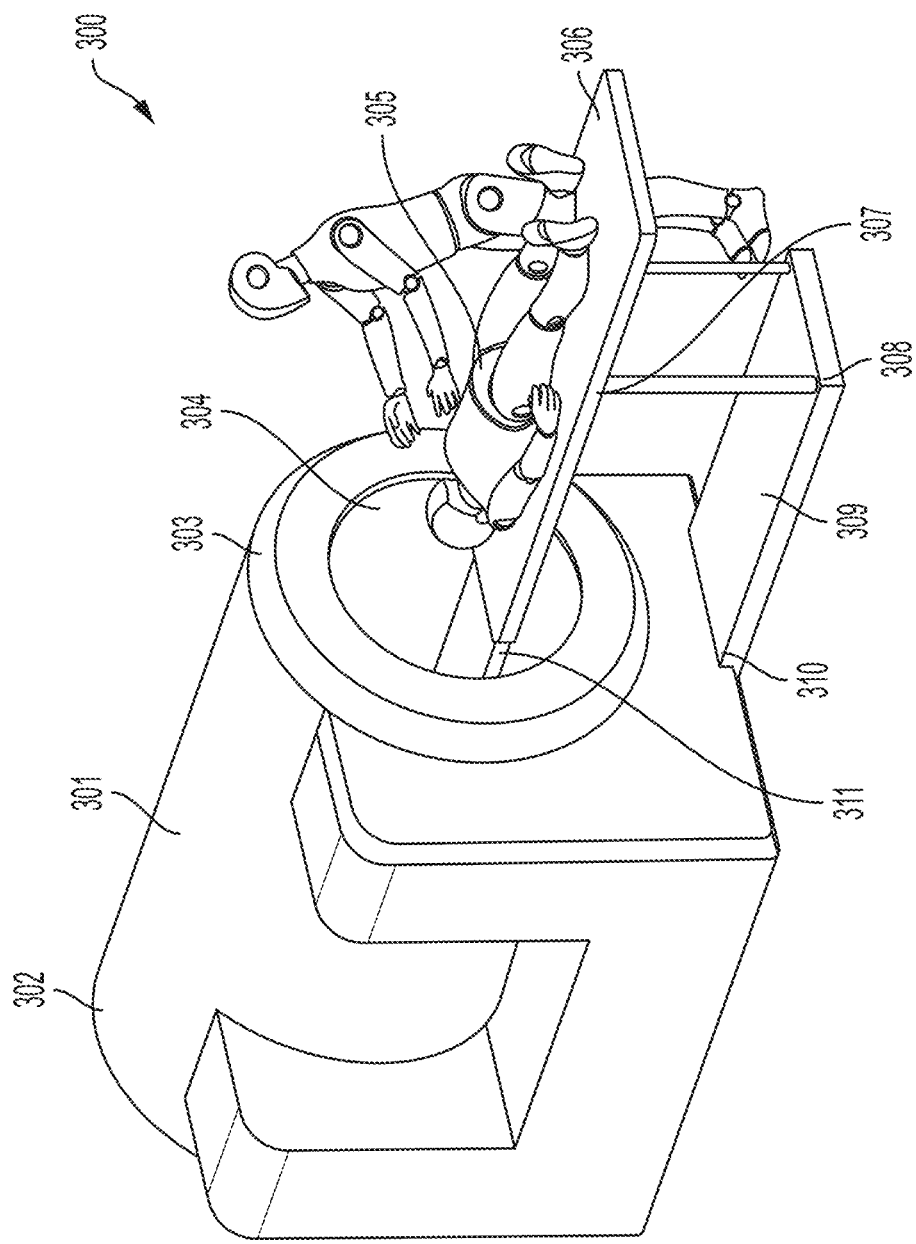
FIG. 3 shows one example of a shield and base unit.

As shown in FIG. 3, an exemplary embodiment of a device or system 300 as described herein comprises a shield 301. The shield 301 comprises a closed end 302 and an open end 303. In some embodiments, an open end 303 of a shield 301 is positioned opposite a closed end 302 of the shield 301. In some embodiments, an open end 303 of a shield 301 is positioned adjacent to a closed end 302 of the shield 301. In some embodiments, an open end 303 is configured to position a sensor, an individual 305, a base unit 306 (such as a movable base unit), or any combination thereof within an inner volume of the shield 301. In some embodiments, a shield 301 comprises an inner surface 304. In some embodiments, an inner surface 304 of a shield 301 spatially defines an inner volume of the shield 301. In some embodiments, an inner surface 304 is configured to interface with an individual 305. In some embodiments, an inner surface 304 comprises venting or lighting to accommodate an individual 305. In some embodiments, a base unit 306 comprises one or more pivots, such that one or more portions of a base unit 306 is adjustable. For example, a base unit 306, in some embodiments, comprises a first pivot 307 and a second pivot 308. In some embodiments, a pivot is configured to adjust a position of a base unit 306 relative to a shield 301. In some embodiments, a pivot is configured to adjust a position of a base unit 306 relative in an inner volume of a shield 301. In some embodiments, a base unit 306 comprises 1, 2, 3, 4, 5, 6, 7, 8 or more pivots. In some embodiments, a pivot provides a movement in one or more degrees of freedom. In some embodiments, a pivot provides a bending motion. In some embodiments, a pivot provides a rotational motion. In some embodiments, a pivot provides an extending motion. In some embodiments, a base unit 306 comprises a base 309. In some embodiments, a base 309 is configured to support a portion of the base unit 306 that holds an individual 305, a sensor, a sensor array or a combination thereof. In some embodiments, a base 309 is configured to move into an opening 310 of a shield 301, such that a portion of the base unit 306 that holds an individual 305, an array, or a combination thereof is moved into and out of an internal volume of the shield 301. In some embodiments, an internal volume of a shield 301 comprises a structure 311, such as a track or channel or rod or protrusion that is configured to accept a portion of the base unit 306 (such as a portion associated with an individual 305, an sensor or both) as the portion is moved into and out of the internal volume of the shield 301.

Figure 4:
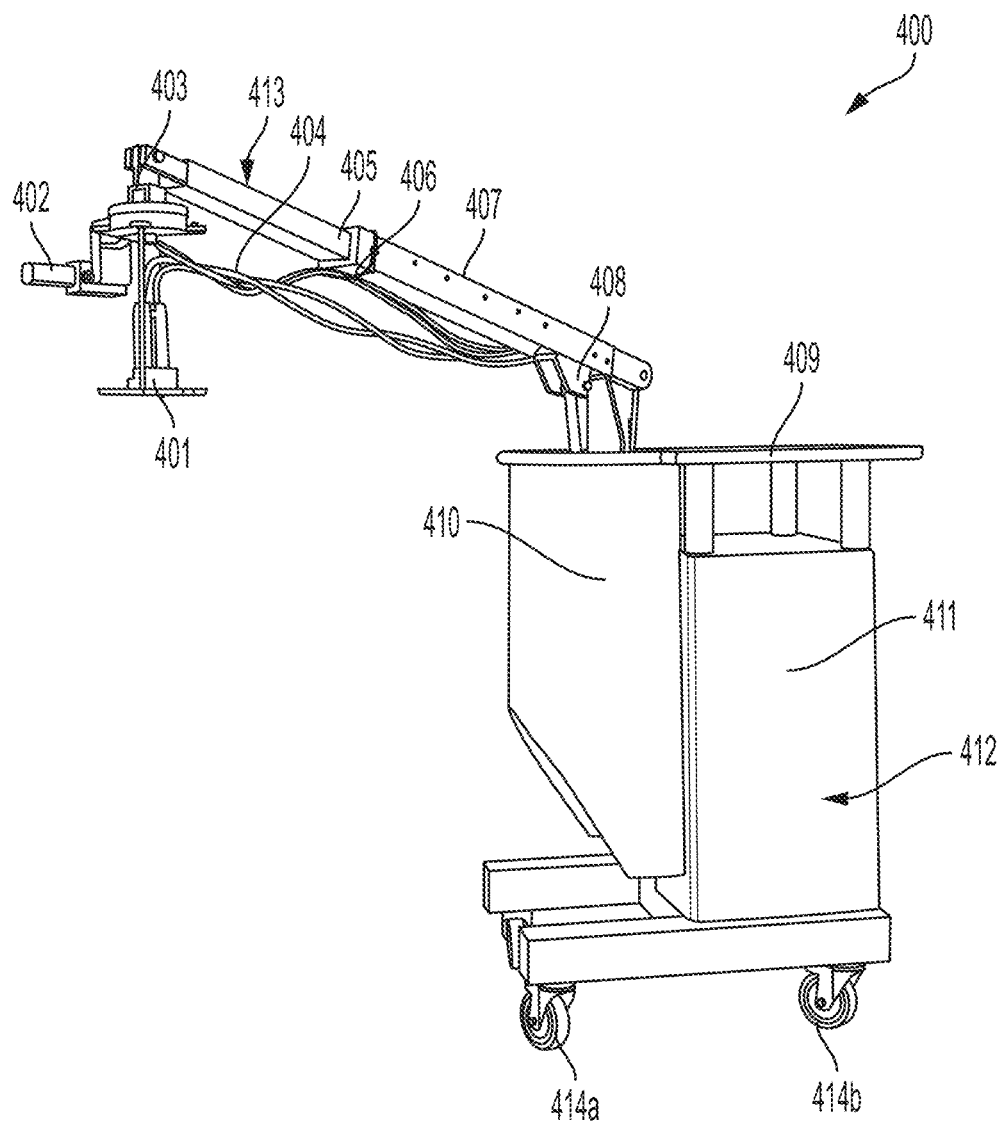
FIG. 4 shows one example of a sensor array operatively coupled to a base unit.

As shown in FIG. 4, an exemplary device or system 400 as described herein comprises a base unit 412 (such as a mobile base unit 412) and one or more sensors that in some embodiments comprise an array of sensors 401 (such as an optically pumped magnetometer).

In some embodiments, a device 400 comprises a structure 402, such as a handle, a beam, or rod, or protrusion that is configured to allow a user to adjust a position of the array 401.

In some embodiments a device 400 comprises one or more pivots (such as 403 or 408). In some embodiments, a pivot adjusts a position of a base unit 412 or a subcomponent thereof, a position of an array 401, or a combination thereof In some embodiments, a pivot (403 or 408) is adjusted manually, automatically, or a combination thereof. In some embodiments, a pivot (403 or 408) is adjusted by a user, by a controller, or a combination thereof. In some embodiments, a pivot (403 or 408) is configured to provide movement in one or more degrees of freedom. In some embodiments, a pivot (403 or 408) provides a bending motion. In some embodiments, a pivot (403 or 408) provides an extending motion. In some embodiments, a pivot (403 or 408) provides a rotational motion.

In some embodiments, a base unit 412 comprises one or more compartments (such as 410 or 411). In some embodiments, a base unit 412 comprises a single compartment. In some embodiments, a base unit 412 comprises two compartments. In some embodiments, a base unit 412 comprises a plurality of compartments. In some embodiments, a base unit 412 comprises three compartments. In some embodiments, a first compartment and a second compartment are different. In some embodiments, a first compartment and a second compartment are the same. In some embodiments, a first compartment is larger in size than a second compartment. In some embodiments, a first compartment is positioned adjacent to a second compartment. In some embodiments, a first compartment is positioned above a second compartment. In some embodiments, a first compartment is positioned within a second compartment. In some embodiments, a compartment is configured to house one or more components. For example, a compartment is configured to house a power source, such that a base unit 412 is not restricted to remain proximal to a wall outlet or external power source. In some embodiments, a compartment is configured to house a computer including an operating system, a database, a monitor, a graphical user interface, or any combination thereof In some embodiments, a compartment is configured to house one or more sensors or a housing for a sensor.

In some embodiments, a base unit 412 comprises one or more compartments (such as 409 or 410). In some embodiments, a base unit 412 comprises a single compartment. In some embodiments, a base unit 412 comprises two compartments. In some embodiments, a base unit 412 comprises a plurality of compartments. In some embodiments, a base unit 412 comprises three compartments. In some embodiments, a first compartment and a second compartment are different. In some embodiments, a first compartment and a second compartment are the same. In some embodiments, a first compartment is larger in size than a second compartment. In some embodiments, a first compartment is positioned adjacent to a second compartment. In some embodiments, a first compartment is positioned above a second compartment. In some embodiments, a first compartment is positioned within a second compartment. In some embodiments, a compartment is configured to house one or more components. For example, a compartment is configured to house a power source, such that a base unit 412 is not restricted to remain proximal to a wall outlet or external power source. In some embodiments, a compartment is configured to house a computer including an operating system, a database, a monitor, a graphical user interface, or any combination thereof In some embodiments, a compartment is configured to house one or more sensors or a housing for a sensor.

In some embodiments, a base unit 412 comprises a surface 409, such as a flat surface. The surface 409 is configured to hold a computer or other component of the system. In some embodiments, a base unit 412 comprises one or more rotating elements (such as 414a or 414b). In some embodiments, a rotating element comprises a wheel (414a, 414b), a roller, a conveyor belt, or any combination thereof configured to provide movement of a base unit 412. A base unit 412, in some embodiments, comprises an arm 413. In some embodiments, one end of an arm 413 is configured to associate with the array 401 of sensors. In some embodiments, a second end of an arm 413 is configured to associate with the base unit 412, at for example a compartment 410 or 411 or a surface 409. In some embodiments, an arm 413 is adjustable. For example, an arm 413 is extendible in length, such as a first portion 405 of an arm 413 that extends from a second portion 407 of an arm 413. In some embodiments, a first 405 or second 407 portion of an arm 413 comprises a lock element (such as a knob or protrusion or pin-in-groove) for securing the arm 413 or the first 405 or second 407 portion of the arm 413 in an extended, flexed, or collapsed position.

In some embodiments, a pivot 408 is positioned at a first end 405 of an arm 413, at a second end 407 of an arm 413 (as shown in FIG. 4), or a combination thereof. In some embodiments, a pivot 403 is positioned at an end of an arm 413 that is adjacent an array 401. In some embodiments, a pivot 408 is positioned at an end of an arm 413 that is adjacent a compartment 410 or 411 or a surface 409. In some embodiments, a base unit 412 comprises wiring 404, such as one or more wires. Wiring 404 is configured to associate with one or more sensors of an array 401, one or more power sources of the base unit 412, one or more computers of the base unit 412, or any combination thereof. The base unit 412, in some embodiments, comprises a wire securing element 406 (such as a tie or latch or hook) to secure one or more wires of the base unit 412. In some embodiments, a wire securing element 406 is positioned on an arm 413 of the base unit 412. In some embodiments, a wire securing element 406 is positioned in a compartment of the base unit 412. In some embodiments, a wire securing element 406 is positioned proximal an array 401, proximal an extension point of an arm 413, proximal a pivot (403 or 408), or any combination thereof.

In some embodiments, a device 400 is combined with a shield (not shown) such as, for example, a disposable shield or a modular shield. In some embodiments, a shield is separate from a base unit 412. In some embodiments, a shield is associated with a base unit 412, such as attached to a base unit 412 at a position that is proximal the array 401.

In some embodiments, a shield is integral to the device 400. In some embodiments, a shield, an array 401, an arm 413, or any combination thereof is operatively connected (such as by wiring or wirelessly) to a controller or computer system.

Figure 5:
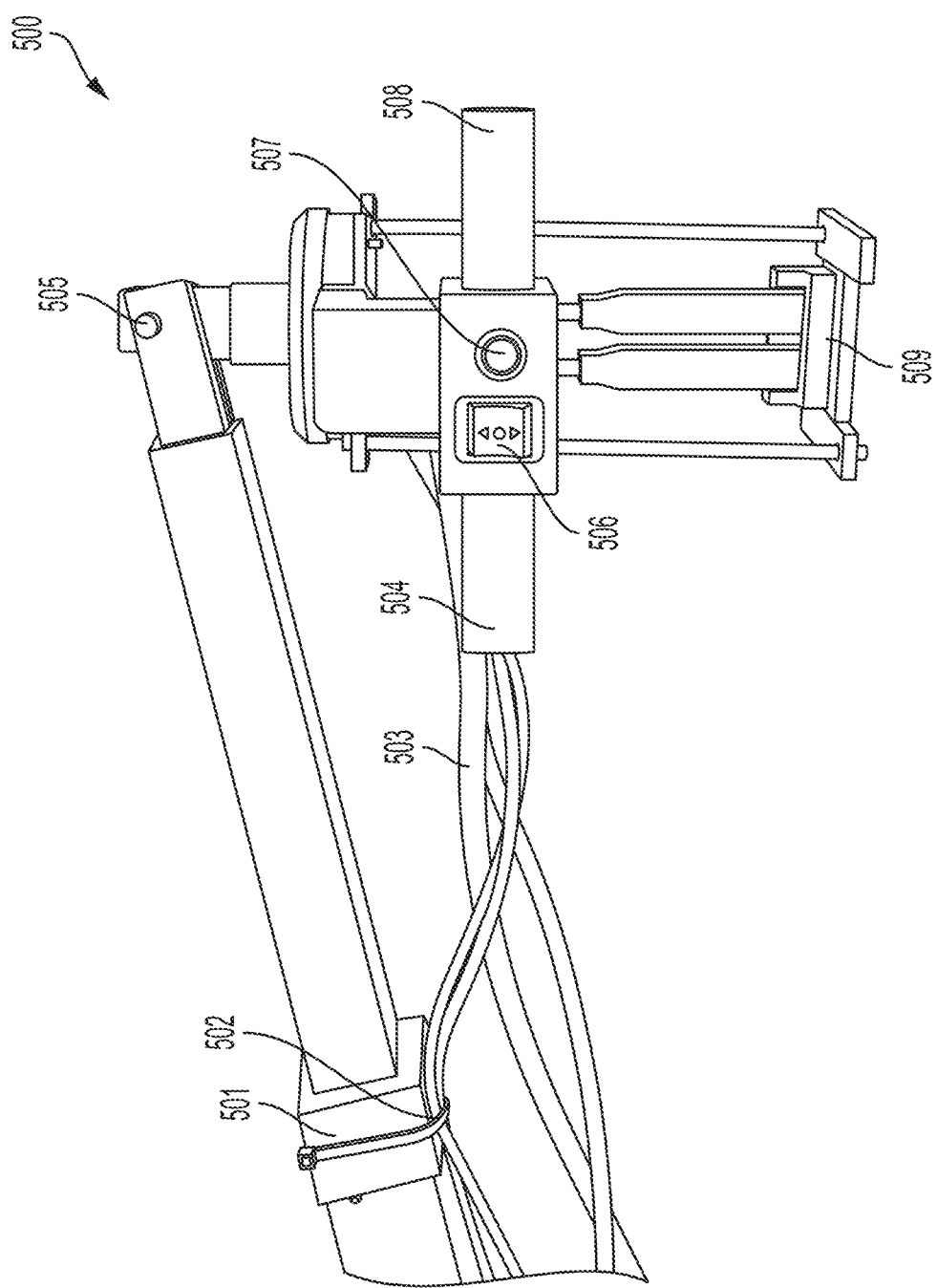
FIG. 5 shows one example of a sensor array operatively coupled to an arm.

As shown in FIG. 5, in some embodiments of the devices and systems described herein, an arm 500 of a mobile cart device comprises an articulating and/or extending mechanism 501. As shown in FIG. 5, in some embodiments an extending mechanism 501 comprises a telescoping housing for a portion of arm 500 to telescope in and out of. In some embodiments, an articulating mechanism 501 comprises a joint.

An arm 500, in some embodiments, comprises one or more holders 502, such as a holder for securing a wiring component 503 to a position on the arm 500. In some embodiments, a holder 502 is located at any position along a length of an arm 500. In some embodiments, a location of a holder 502 along a length of an arm 500 is adjustable. In some embodiments, a housing or tubing 504 is configured to house one or more wiring components 503. In some embodiments, a wiring component 503 operatively connects a sensor array to one or more components, such as a computer or power source. The arm 500, in some embodiments, comprises a first and second end. In some embodiments, a first end of the arm 500 is configured to be coupled to the sensor array 509. The first end is coupled to the sensor array by a pivot 505. In some embodiments, a pivot 505 provides one or more degrees of freedom of movement to the sensor array 509. In some embodiments, a position of a sensor array is adjusted by employing an actuator, such as a motorized button 506. The actuator, in some embodiments, adjusts a linear motion of the sensor array such as towards or away from a surface of an individual. In some embodiments, the actuator has a separate power button 507. In some embodiments, the motorized button 506 and the power button are the same. In some embodiments, the actuator comprises a bar or a handle 508. The bar is configured for manual adjustment of the arm 500 position, the sensor array position, or a combination thereof.

Figure 6:
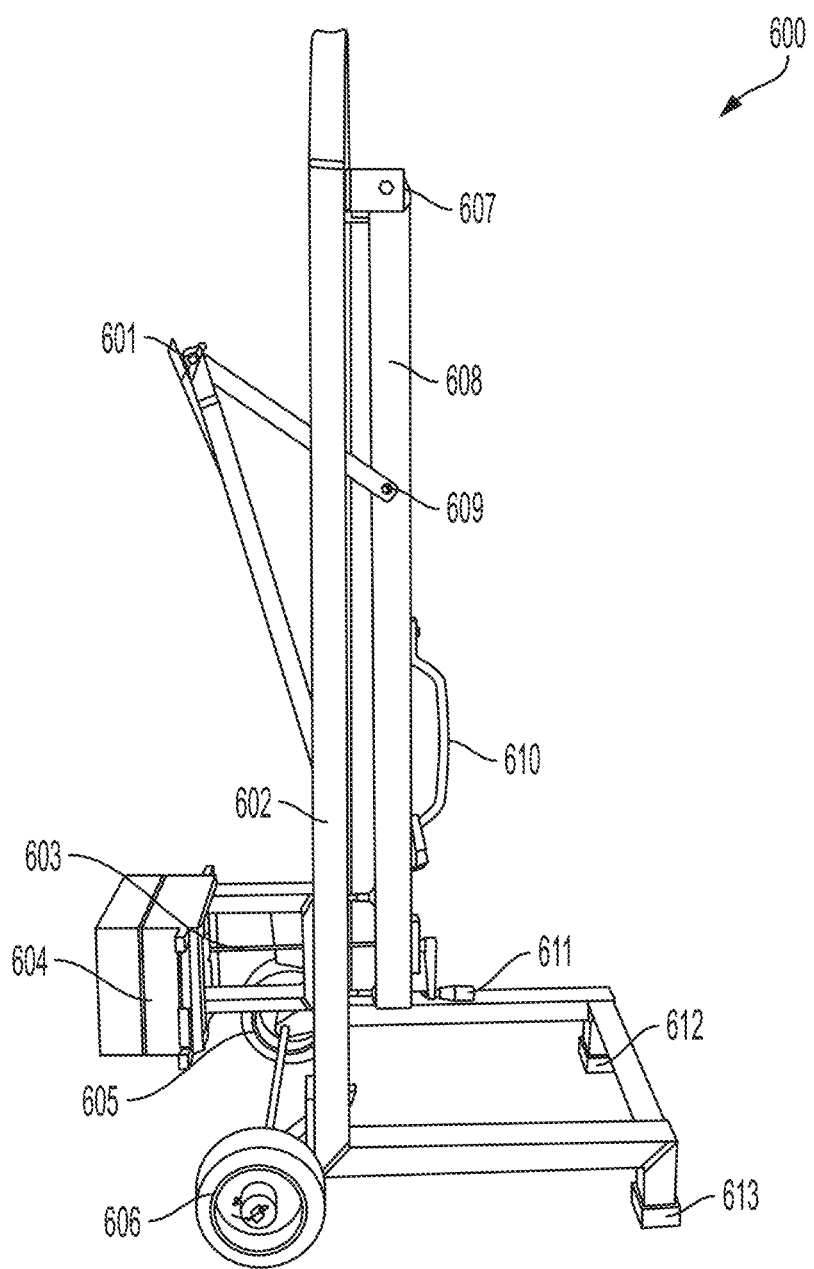
FIG. 6 shows one example of a sensor array operatively coupled to a base unit.
Figure 7:
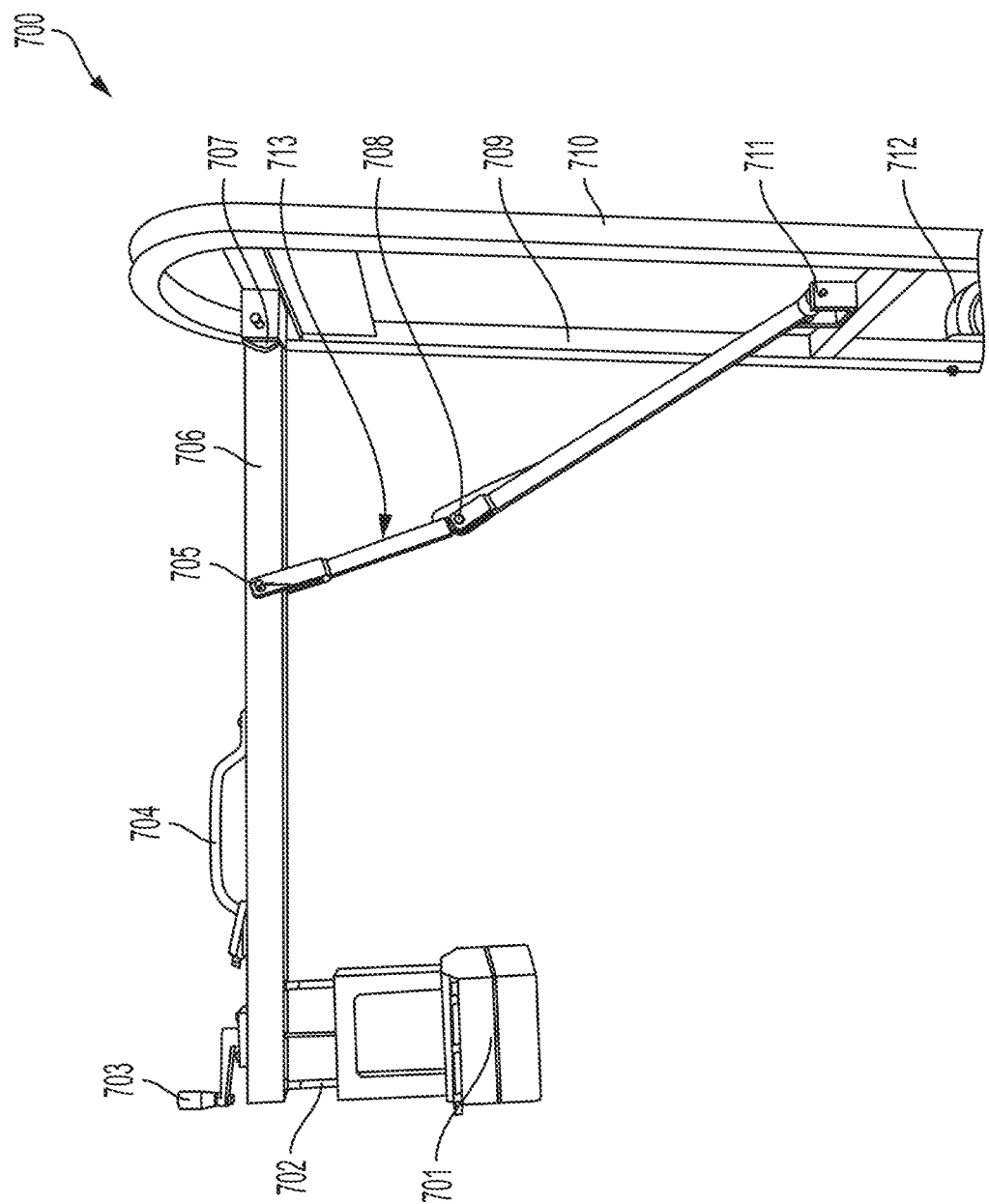
FIG. 7 shows one example of a sensor array operatively coupled to an arm of a base unit.

In some embodiments, a mobile cart device is configured to transition from an extended configuration as shown in FIG. 7 to a collapsed configuration as shown in FIG. 6. In some embodiments, a mobile cart device is configured to transition between two configurations one or more times. In some embodiments, a mobile cart device is configured for a user to manually transition the device between two configurations. In some embodiments, a mobile cart device is configured for automatic transition between two configurations, such as automated by a motor system operatively coupled to a controller.

FIG. 6 shows an exemplary mobile cart device 600 in a collapsed configuration. As shown in FIG. 6, a mobile cart device 600 comprises a sensor array 604, such as an optically pumped magnetometer. The sensor array 604 is coupled to a first end of an arm 608. In some embodiments, a second end of the arm 608 is coupled at location 607 to a top end of a vertical beam 602 or frame. The coupling, in some embodiments, comprises a pivot. In some embodiments, a pivot coupling is configured to transition the device 600 from an extended configuration to a collapsed configuration. In some embodiments, a cross beam 601 is coupled at location 609 to the arm 608 at any position between the first end and the second end. In some embodiments, a cross beam 601 is coupled to the arm 608 at a midpoint between the first end and the second end of the arm 608. In some embodiments, the cross beam 601 comprises a pivot, such as a pivot positioned at a midpoint along the cross beam 601. In some embodiments, a cross beam pivot is configured to transition the device 600 from an extended configuration to a collapsed configuration. In some embodiments, a cross beam 601 is configured to bend or to pivot such that the first end coupled to the sensor array 604 is moved towards a bottom end of the vertical beam 602. One or more pivots of a device 600 are locked in a configuration, such as an extended configuration or a collapsed configuration, such as by a locking element at position 607 or 601, or both.

In some embodiments, a mobile cart device 600 comprises a handle 610, such as a handle that is coupled to the arm 608. The handle 610, in some embodiments, facilitates actuation of the arm 608 to transition the device 600 between an extend configuration and a collapsed configuration. In some embodiments, a mobile cart device 600 comprises one or more rotating elements (such as wheels 605 and 606) configured to rotate such that the mobile cart device 600 is moved. In some embodiments, a mobile cart device 600 comprises one or more anchoring elements (such as rubber feet 612 and 613) configured to secure the mobile cart device 600 in a desired location. In some embodiments, a mobile cart device 600 comprises a handle 611. In some embodiments, a handle 611 is configured to actuate one or more elements of the device 600. For example, a handle 611 is configured to actuate an arm 608 of the device 600 relative to the frame. In some embodiments, a handle 611 is configured to actuate a sensor array 604 relative to the arm 608. In some embodiments, a handle 611 translates a sensor array 604 in linear motion towards or away from an arm 608. In some embodiments, a handle 611 is configured to rotate. In some embodiments, a handle 611 is operatively coupled to a drive screw 603 for translating rotational motion of the handle 611 to linear motion of the sensor array 604.

FIG. 7 shows an exemplary mobile cart device 700 similar to FIG. 6 and in an extended configuration. A device 700 comprises a sensor array 701, comprising one or more optically pumped magnetometer. The sensor array 701 is operatively coupled to a first end of an arm 706 of the device 700 by one or more shafts (such as a linear motion shaft 702). In some embodiments, a second end of the arm 706 is coupled at location 707 to one or more vertical beams (such as beam 709 and beam 710). The coupling located at location 707, in some embodiments, comprises a pivot. The coupling is configured to transition the arm 706 between an extended configuration and a collapsed configuration. In some embodiments, the coupling is configured to move the sensor array 701 towards and away from the vertical beam.

The arm 706, in some embodiments, comprises a handle 704, a handle 703, or both configured to actuate a portion of the device 700. For example, handle 704 is configured to move the arm 706 relative to the frame. Handle 703 is configured to move the sensor array 701 relative to the arm 706. A device 700, in some embodiments, comprises a cross beam 713. In some embodiments, a first end 705 of a cross beam 713 is coupled to the arm 706, at a position between the first end and the second end of the arm 706, such as a midpoint position. In some embodiments, a second end 711 of the cross beam 713 is coupled to the frame, such as to a vertical beam or a cross beam 713 positioned between two vertical beams. A cross beam 713, in some embodiments, comprises a pivot 708. In some embodiments, a pivot is positioned at a midpoint on the cross beam 713. In some embodiments, a pivot 708 is configured to bend. In some embodiments, a pivot 708 is configured to transition the device between a collapsed configuration and an extended configuration. In some embodiments, a pivot 708 is reversibly lockable. A device 700, in some embodiments, comprises one or more rotating elements, such as a wheel 712, configured to move the device between locations.

Figure 8:
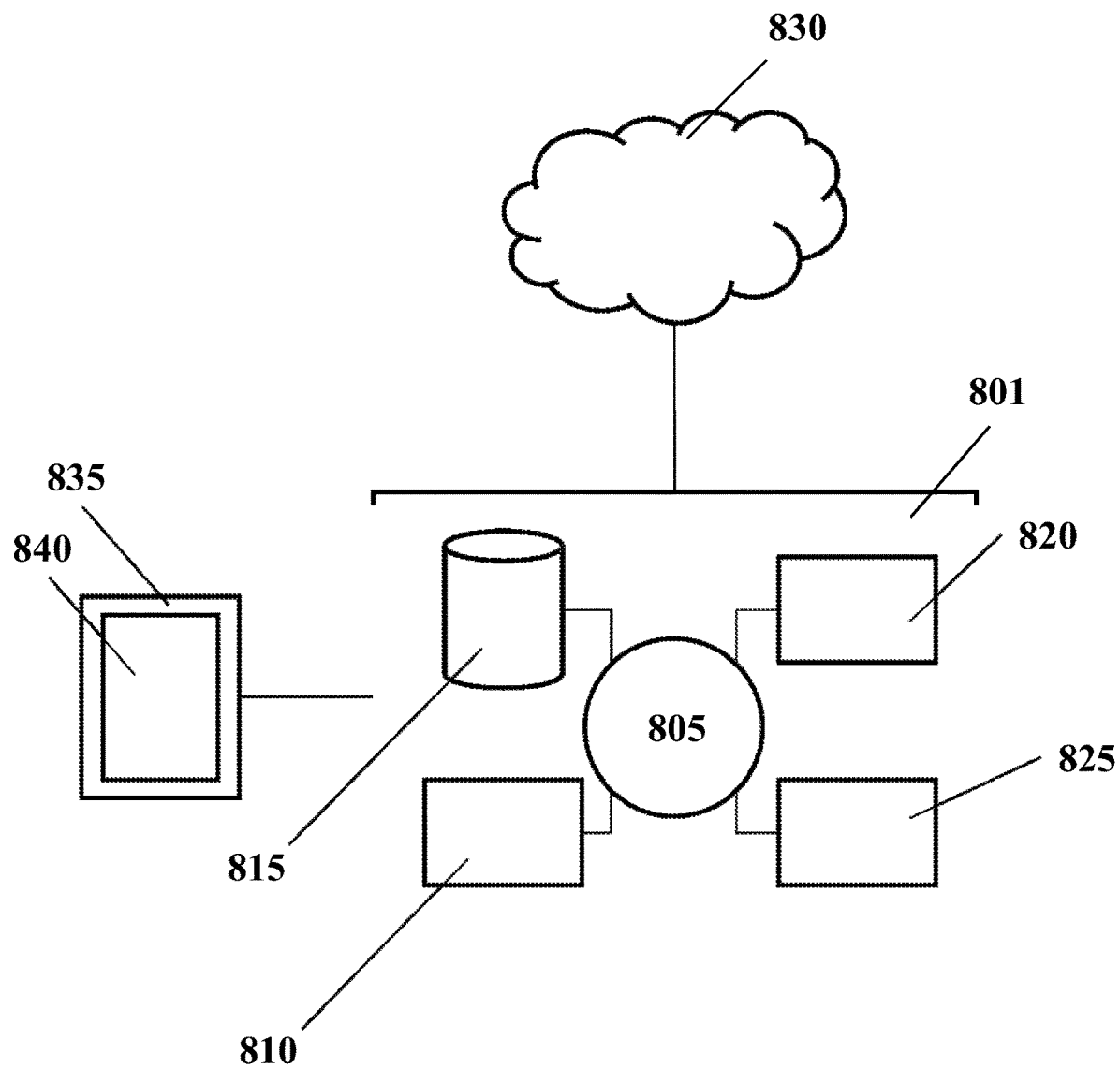
FIG. 8 shows a computer control system that is programmed or otherwise configured to implement methods provided herein.

FIG. 8 shows an exemplary computer system 801 that is programmed or otherwise configured to direct operation of a device or system as described herein, including movement of a base unit, movement of a shield, movement of a mobile cart, movement of a sensor array, acquisition of a measurement, comparison of a measurement to a reference measurement, or any combination thereof. The computer system 801 regulates various aspects of (a) movement of one or more device or system components, (b) operation of one or more sensors, (c) adjustment of one or more parameters of a sensor, (d) computationally evaluation of one or more measurements of a device or system, (e) display of various parameters including input parameters, results of a measurement, or any combination of any of these. In some embodiments, a computer system 801 is an electronic device of a user (e.g. smartphone, laptop) or, in some embodiments, is remotely located with respect to the electronic device. The electronic device, in some embodiments, is a mobile electronic device.

The computer system 801 includes a central processing unit (CPU, also "processor" and "computer processor" herein) 805, which, in some embodiments, is a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 is configured as a data storage unit (or data repository) for storing data. The computer system 801 is operatively coupled to a computer network ("network") 830 with the aid of the communication interface 820. The network 830 is the Internet, an internet and/or extranet, or an intranet and/or extranet that is in communication with the Internet. The network 830 in some embodiments is a telecommunication and/or data network. The network 830 includes one or more computer servers, which enable distributed computing, such as cloud computing. The network 830, in some embodiments, with the aid of the computer system 801, implements a peer-to-peer network, which enables devices coupled to the computer system 801 to behave as a client or a server.

The CPU 805 is configured to execute a sequence of machine-readable instructions, which are be embodied in a program or software. The instructions are stored in a memory location, such as the memory 810. The instructions are directed to the CPU 805, which is subsequently program or otherwise configure the CPU 805 to implement methods of the present disclosure. Examples of operations performed by the CPU 805 include fetch, decode, execute, and writeback.

The CPU 805 is part of a circuit, such as an integrated circuit. One or more other components of the system 801 are included in the circuit. In some embodiments, the circuit is an application specific integrated circuit (ASIC).

The storage unit 815 stores files, such as drivers, libraries and saved programs. The storage unit 815 stores user data, e.g., user preferences and user programs. The computer system 801 in some embodiments include one or more additional data storage units that are external to the computer system 801, such as located on a remote server that is in communication with the computer system 801 through an intranet or the Internet.

The computer system 801 communicates with one or more remote computer systems through the network 830. For instance, the computer system 801 communicates with a remote computer system of a user (e.g., a second computer system, a server, a smart phone, an iPad, or any combination thereof). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user accesses the computer system 801 via the network 830.

Methods as described herein are implemented by way of machine (e.g., computer processor) executable code stored on an electronic storage location of the computer system 801, such as, for example, on the memory 810 or electronic storage unit 815. The machine executable or machine readable code is provided in the form of software. During use, the code is executed by the processor 805. In some embodiments, the code is retrieved from the storage unit 815 and stored on the memory 810 for ready access by the processor 805. In some situations, the electronic storage unit 815 is precluded, and machine-executable instructions are stored on memory 810.

A machine readable medium, such as computer-executable code, takes many forms, including but not limited to, a tangible storage medium, a carrier wave medium or physical transmission medium. Non-volatile storage media include, for example, optical or magnetic disks, such as any of the storage devices in any computer(s) or the like, such as is used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media takes the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer reads programming code and/or data. Many of these forms of computer readable media is involved in carrying one or more sequences of one or more instructions to a processor for execution.

The computer system 801, in some embodiments, includes or is in communication with an electronic display 835 that comprises a user interface (UI) 840 for providing, for example, a graphical representation of one or more signals measured, one or more reference signals, one or more parameters that is input or adjusted by a user or by a controller, or any combination thereof. Examples of UI's include, without limitation, a graphical user interface (GUI) and web-based user interface.

Methods and systems of the present disclosure are, in some embodiments, implemented by way of one or more algorithms. An algorithm, in some embodiments, is implemented by way of software upon execution by the central processing unit 805. The algorithm is, for example, comparing a signal to a reference signal.

Figure 9A:
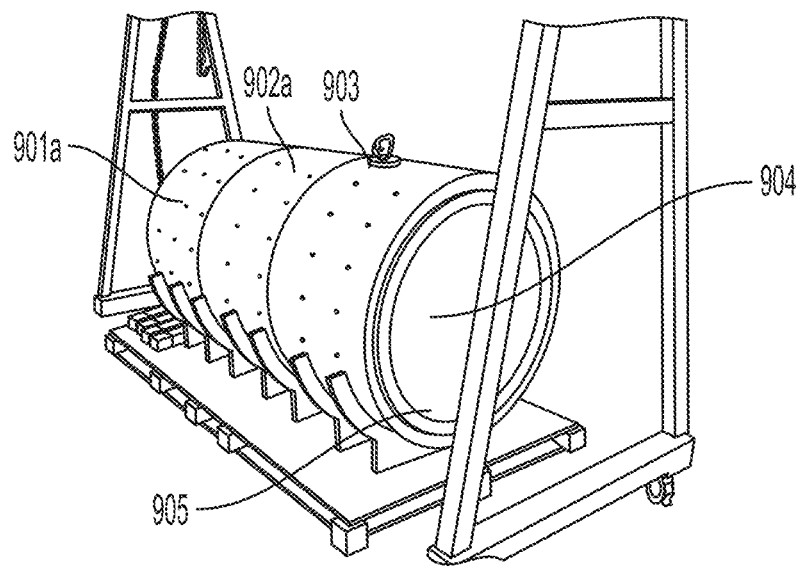
FIGS. 9A-B shows one example of a shield. The shield of FIG. 9A is positioned to show an open end and internal volume of the shield. The shield of FIG. 9B is positioned to show a closed end of the shield having a tapered or conical shape.
Figure 9B:
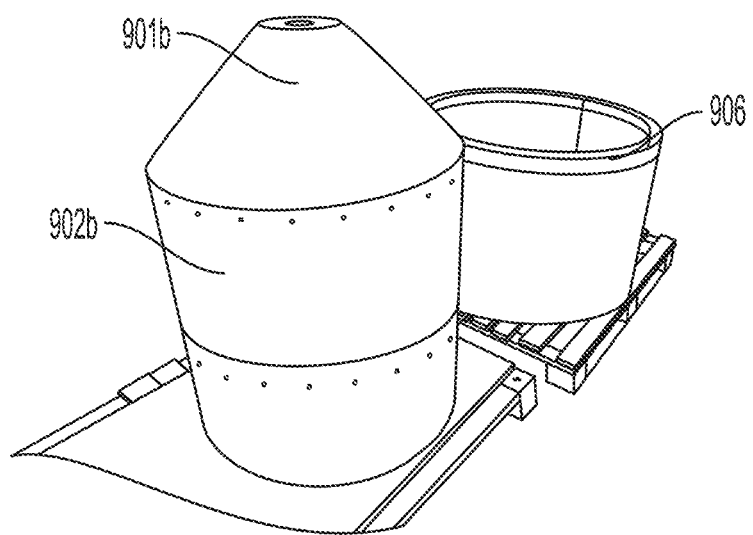

FIGS. 9A-B show an example of a shield. In some embodiments, a shield has a first end and a second end. A first end of a shield, in some embodiments, comprises a closed taper end 901a or 901b. In some embodiments, a second end of the shield comprises an open end 904, substantially cylindrical in shape. In some embodiments, the opening of the second end is configured to receive at least a portion of an individual, a sensor array, a base unit, or any combination thereof into the shield. In some embodiments, a shield is monolith. In some embodiments, a shield is formed of one or more segments, such as a first segment 901*a* or 901*b*, a second segment 902*a* or 902*b*, and a third segment 903. In some embodiments, a shield comprises one layer. A shield, in some embodiments, comprises more than one layer. A shield, in some embodiments, comprises an inner layer 905. A shield, in some embodiments, comprises a spacing 906 between two layers.

Figure 10A:
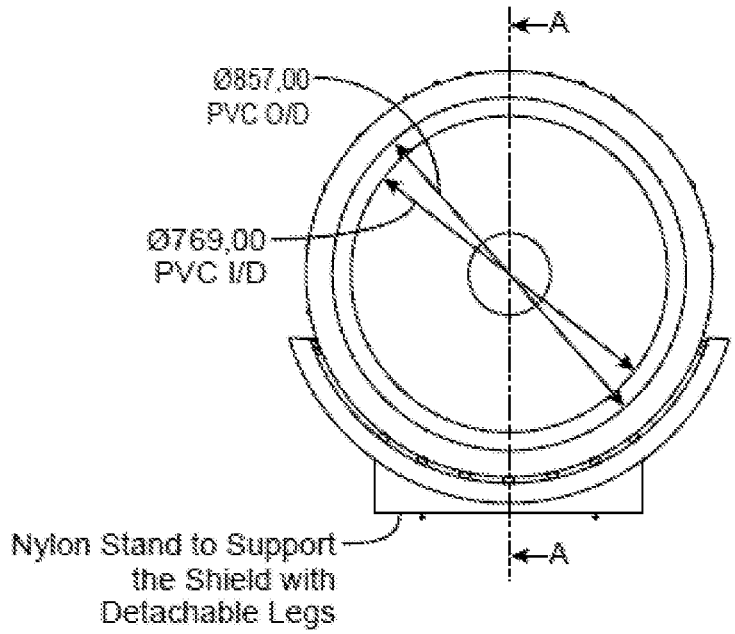
FIGS. 10A-B shows two different cross section views of a shield.
Figure 10B:
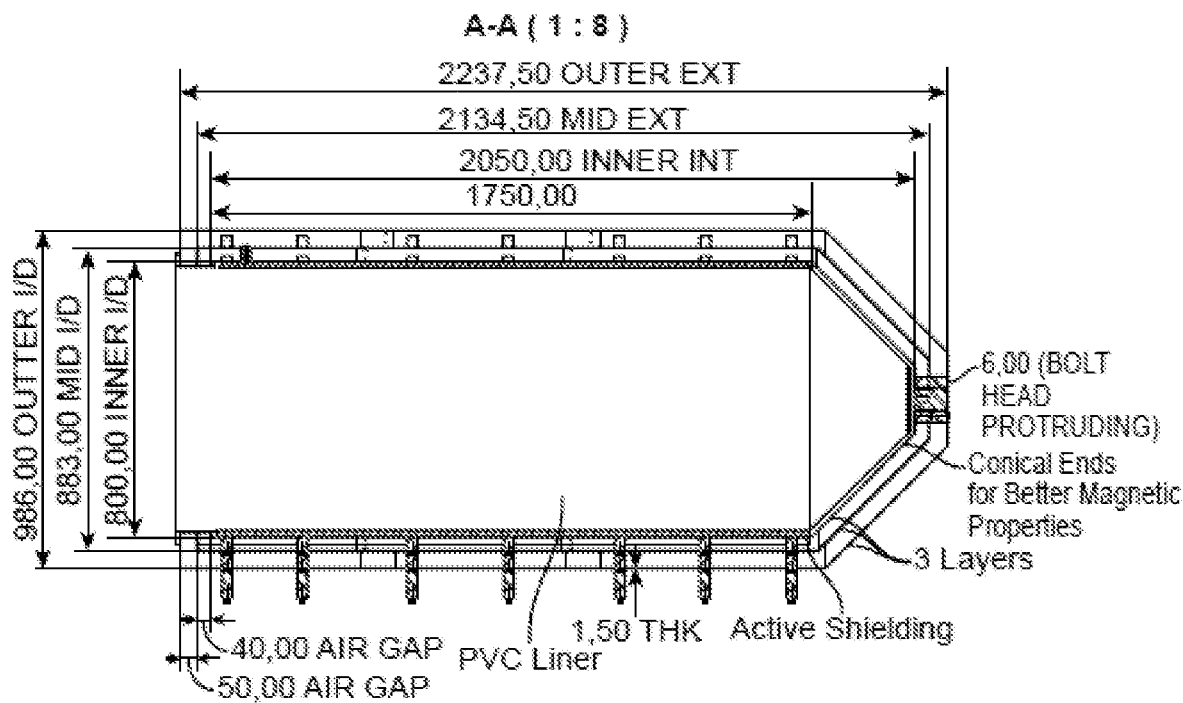
Figure 11A:
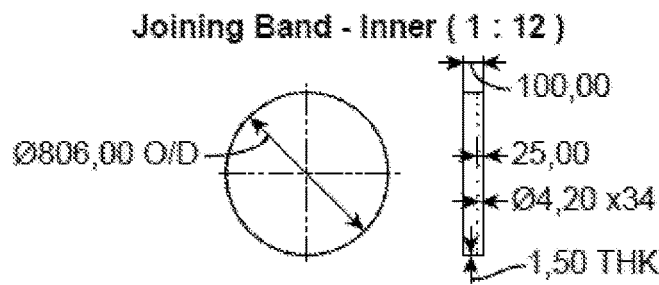
Figure 11B:
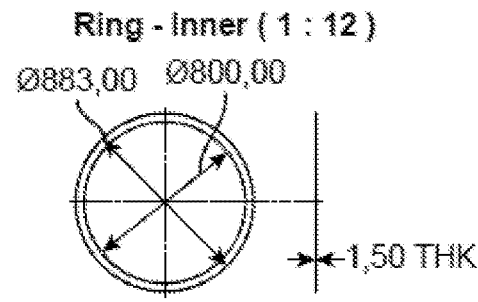
Figure 11C:
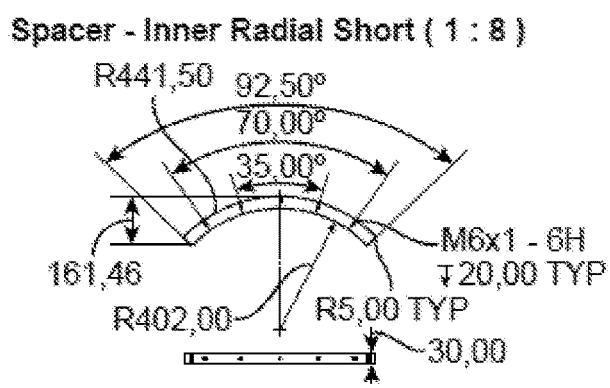
Figure 11D:
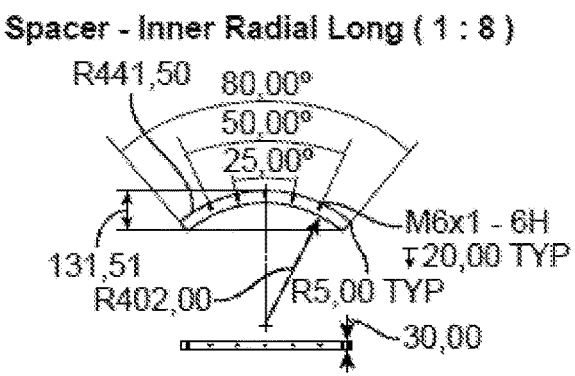
Figure 11E:
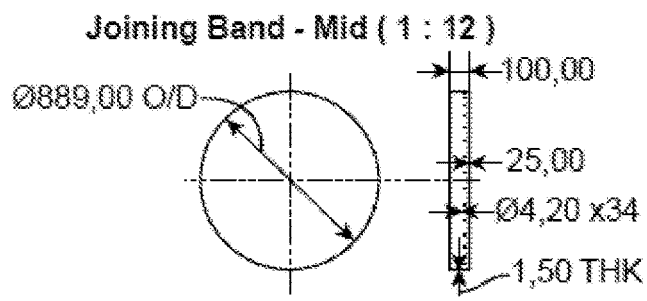
Figure 11F:
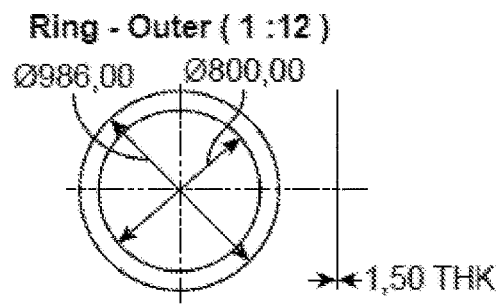
Figure 11G:
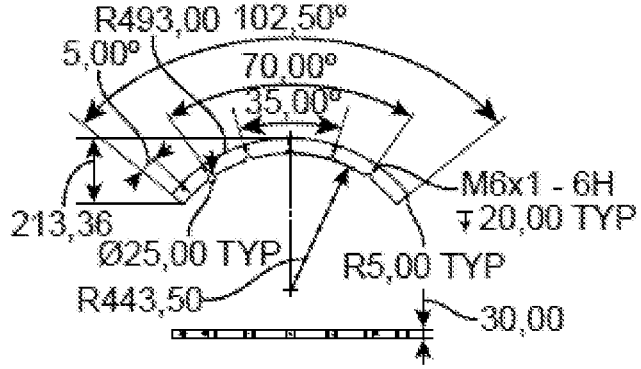
Figure 11H:
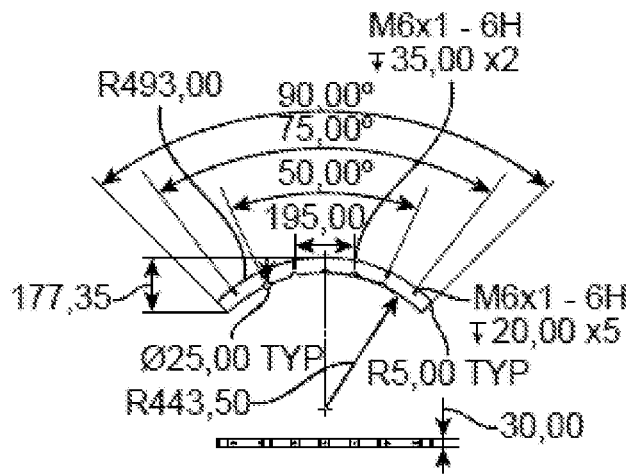
Figure 11I:
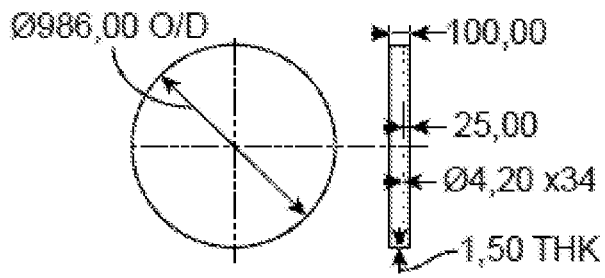

FIGS. 10A-B show an exemplary engineering drawing of the shield that is shown in FIGS. 9A-B. As shown in FIG. 10A, a cross-sectional view of the shield demonstrates an example of suitable geometrical dimensions for a shield. The shield is shown as the cylindrical portion of the picture, with supports below comprising nylon, though attachments and supports is constructed of any nonferrous material known in the art. FIG. 10B shows the longitudinal view of the same sample shield. In some embodiments, a shield has an overall length of from about 2000 millimeters (mm) to about 2500 mm or from about 2200 mm to about 2300 mm (such as about 2272.5 mm), an inner length of from about 1500 mm to about 2000 mm or from about 1700 mm to about 1800 mm (such as about 1750.0 mm), an inner layer with diameter of from about 500 mm to about 1000 mm or from about 700 mm to about 900 mm (such as about 800.0 mm), a middle layer with diameter of from about 600 mm to about 1100 mm or from about 800 mm to about 950 mm (such as about 883.0 mm), and an outer layer with diameter of from about 700 mm to about 1200 mm or from about 900 mm to about 1050 mm (such as about 986.0 mm), as indicated by FIGS. 10A-B.

A shield, in some embodiments, comprises more than one layer with spacing between any two given layers. In some embodiments, a shield has non-uniform spacing between any two layers. Different sets of layers, in some embodiments, have non-uniform spacing relative to each other.

A layer of a shield or portion thereof, in some embodiments, comprises a thickness from about 0.1 to about 10 millimeters. In some embodiments, a layer of a shield has a thickness from about 0.5 to about 5 millimeters. In some embodiments, a layer of a shield has a thickness from about 0.1 to about 2 millimeters. In some embodiments, a layer of a shield has a thickness from about 0.8 to about 5 millimeters. A thickness is substantially the same along a length or a circumference of a shield. In some embodiments, a thickness of a layer of a shield varies along a length or circumference of a shield.

In some embodiments, a shield comprises a plurality of layers. In some embodiments, a space is present between at least two layers of the plurality of layers. In some embodiments, a space is present between each layer of the plurality of layers. In some embodiments, a space is present between a subset of layers of the plurality of layers. In some embodiments, a first layer of a shield is configured to be adjacent a second layer of a shield. In some embodiments, a first layer of a shield is configured to be attached or bonded to a second layer of a shield. In some embodiments, a first layer of a shield is configured to be positioned from about 0.1 inches to about 5 inches from a second layer. In some embodiments, a first layer of a shield is configured to be positioned from about 1 inch to about 3 inches from a second layer. In some embodiments, a first layer of a shield is configured to be positioned from about 1 inch to about 20 inches from a second layer. In some embodiments, a first layer of a shield is configured to be positioned from about 1 inch to about 10 inches from a second layer.

In some embodiments, a length of a shield, such as an internal length or an external length, is about 2× an internal diameter of a shield. In some embodiments, a length of a shield is from about 0.5× to about 3× an internal diameter of a shield. In some embodiments, a length of a shield is from about 1× to about 3× an internal diameter of a shield. In some embodiments, a length of a shield is from about 1.5× to about 3× an internal diameter of a shield.

In some embodiments, as shown in FIGS. 11A-L, the layers of the shield are separated using spacers of variable width, height, and length depending on the application of interest. In some embodiments, the spacers used to separate layers of the shield take the form of an arc. In some embodiments, spacers are used to cover a portion or the entire circumference of two consecutive layers. In some embodiments, spacers cover only part of the circumference of two consecutive layers.

In some embodiments, as shown in FIGS. 12A-B, a shield support is manufactured in one or more pieces and is configured to be operatively connected (such as joined) by way of bolts, fasteners, screws, or any combination thereof. In some embodiments, a shield support is operatively connected (such as attached) to a shield by one or more: fasteners, bolts, screws, or any combination thereof. In some embodiments, a support is also attached using an adhesive fastener. In some embodiments, as seen in FIG. 12A, a shield spacer is positioned anywhere along the circumference of two consecutive layers. In some embodiments, a system of one or more hooks is operatively connected (such as attached) to any surface of any layer of the shield by an adhesive, a fastener, a screw, a bolt, or any combination thereof. A layer, comprises a protective layer. An inner layer, a middle layer, an outer layer, or any combination thereof, in some embodiments, comprises a protective layer. In some embodiments, a portion of a layer comprises a protective layer. A protective layer, in some embodiments, comprises a nonferrous material. A protective layer, in some embodiments, comprises polyvinyl chloride plastic. In some embodiments, a protective layer spans the entire interior surface of a shield. In some embodiments, protective layer spans part of an interior surface of a shield.

Figure 13:
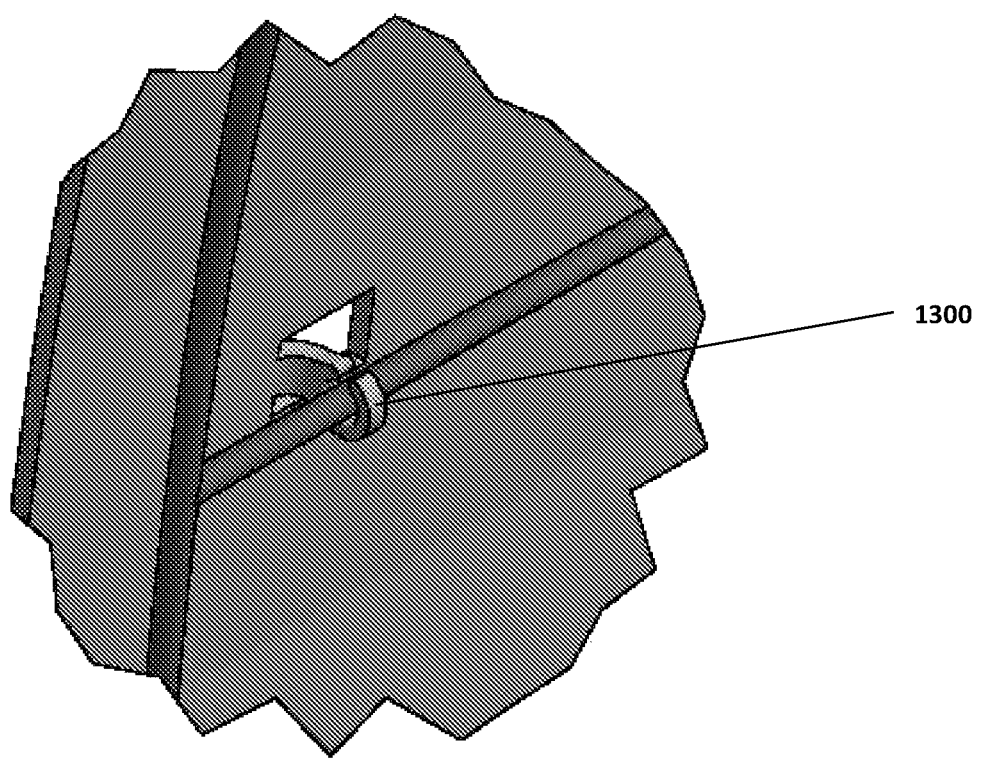
FIG. 13 shows one example of a hook.

FIG. 13, shows an exemplary hook 1300 configured to span a portion of or an entire volume of a shield. In some embodiments, one or more hooks 1300 are operatively connected to a wiring (such as holding a wiring) and is designed to transmit analog electrical signals, digital electrical signals, or a combination thereof. In some embodiments, one or more hooks 1300 are positioned along a single plane of a shield. In some embodiments, hooks 1300 are positioned along more than one plane of a shield. Hooks are positioned along multiple planes. In some embodiments, hooks 1300 are positioned on an inside surface of a shield. In some embodiments, hooks 1300 are positioned circumferentially about a shield at a single cross section. In some embodiments, hooks 1300 are positioned circumferentially about a shield and continuing along a length of a shield. In some embodiments, hooks 1300 are configured to hold an electrical coil system, such as an electrical coil system designed to eliminate an accumulated magnetic field. In some embodiments, hooks 1300 are configured to hold an electrical coil system, such as an electrical coil system designed to create a homogenous magnetic environment inside a shield. In some embodiments, an electrical coil system is configured to employ the use of a wire of variable gauge. An exemplary wire gauge suitable for use with devices and systems described herein is 28 AWG shown in FIG. 13.

Figure 14A:
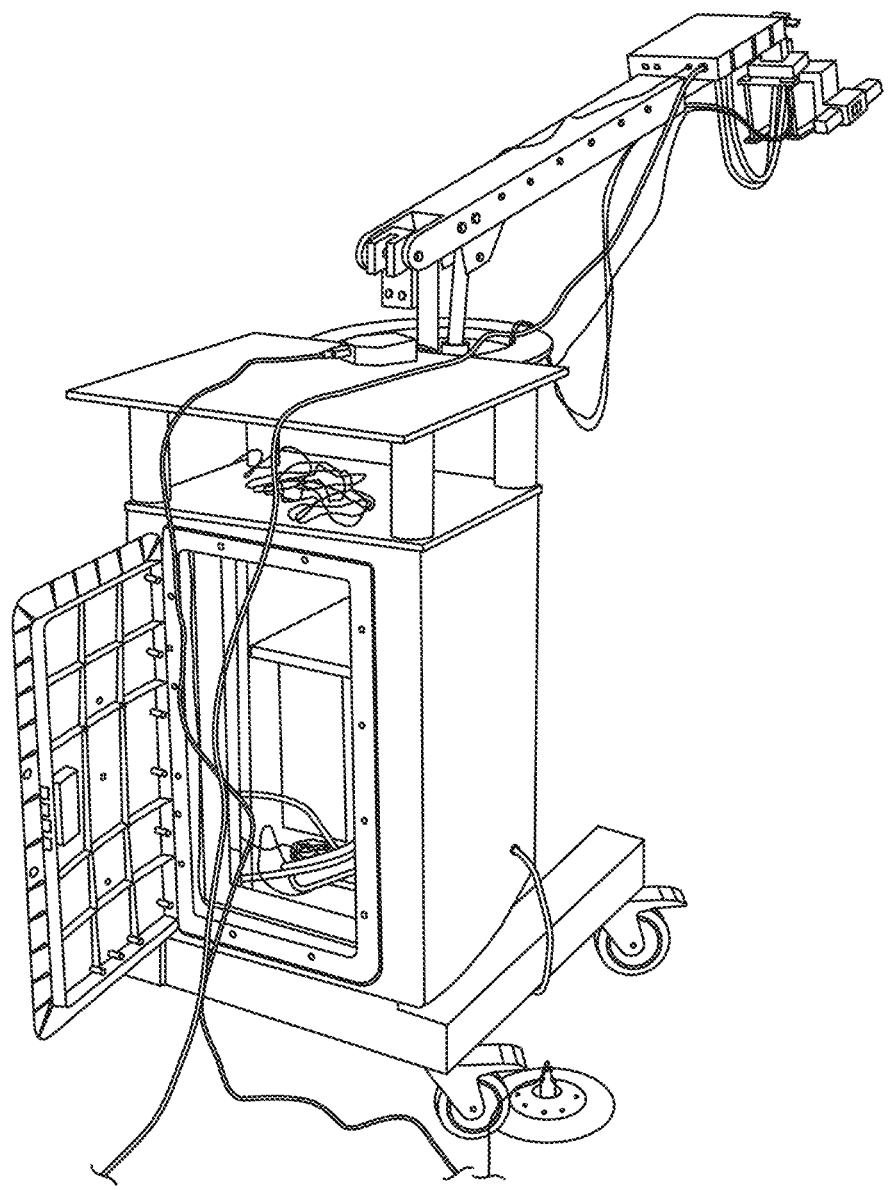
FIGS. 14A-B shows multiple views of a mobile cart device.
Figure 14B:
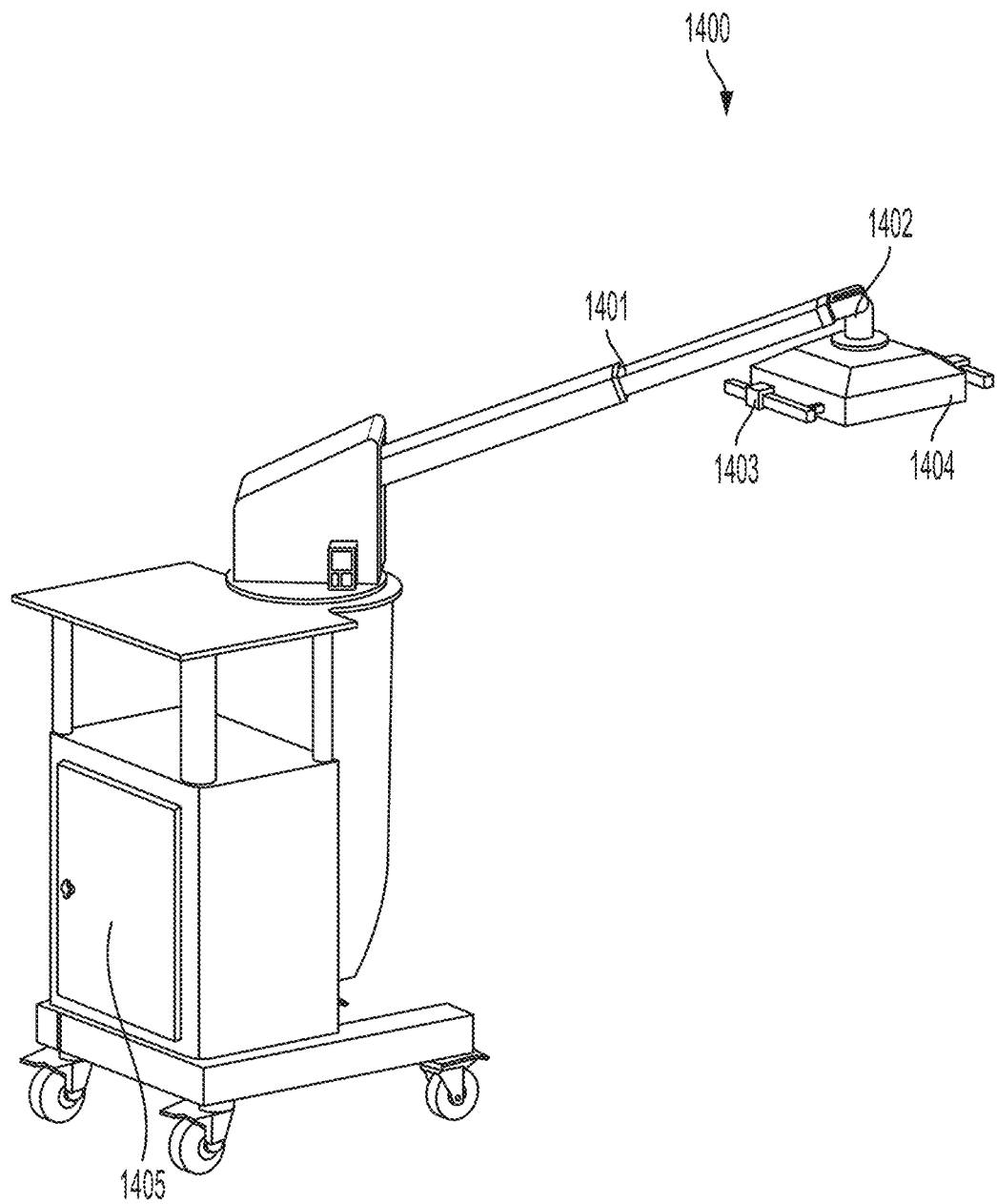

As shown in FIGS. 14A-14B, a mobile cart device, in some embodiments, is capable of operation in a non-magnetically shielded environment. In some embodiments, a computer, electronics, or combination thereof is housed on the mobile cart device itself. In some embodiments, an electronic control module is housed in a compartment (such as a cabinet) of the mobile cart device. In some embodiments, a mobile cart is configured to be powered by a battery (such as a mobile battery). In some embodiments, a device's arm is configured for motorized movement in one or more degrees of freedom.

One example of a mobile cart device 1400 is shown in FIGS. 14A-14B. This example is similar to the example shown in FIG. 4. A device or system as described herein, in some embodiments, comprises a base unit (such as a mobile base unit) and an array of sensors, (such as an optically pumped magnetometer). In some embodiments, the array of sensors is housed in a housing 1404. In some embodiments, the housing 1404 is interchangeable. In some embodiments, the housing 1404 is universally configured to accommodate more than one sensor array configuration. In some embodiments, the housing 1404 is configured to be removable and replaced with a different housing. In some embodiments, the housing 1404 comprises a motor feature 1403, such that an adjusted of a sensor array position is adjusted by pressing the motor feature 1403 on the housing 1404. In some embodiments, the adjustment is automated. In some embodiments, the adjustment is performed manually by a user pressing the motor feature 1403. A base unit, in some embodiments, comprises a structure, such as an arm, a beam, a rod or a protrusion that is configured to allow a user to adjust a position of the array. In some embodiments, the arm is configured to be associated with the sensor array or the housing 1404, such as associated with a bracket 1402. In some embodiments, the arm is extendible. In some embodiments, the arm is movable in one or more degrees of freedom. In some embodiments, a position of an arm, such as an extended arm position, is secured by a locking component 1401. In some embodiments, a locking component 1401, such as a locking solenoid, is positioned on the arm. In some embodiments, a locking component 1401 is operatively integrated with the motor feature 1403. A base unit, in some embodiments, comprises a single compartment 1405. A base unit, in some embodiments, comprises two compartments. A base unit, in some embodiments, comprises a plurality of compartments. In some embodiments, a compartment 1405 is configured to house one or more components. For example, a compartment 1405 is configured to house a power source, such that a base unit is not restricted to remain proximal to a wall outlet or external power source. In some embodiments, a compartment 1405 is configured to house a computer including an operating system, a database, a monitor, a graphical user interface, or any combination thereof. In some embodiments, a compartment 1405 is configured to house one or more sensors or a housing for a sensor. In some embodiments, a compartment 1405 is configured to house a power source, a computer, one or more sensors, a housing for a sensor, wiring, or any combination thereof. A base unit, in some embodiments, comprises a surface, such as a flat surface. In some embodiments, the surface is configured to hold a computer or other component of the system. A base unit, in some embodiments, comprises one or more rotating elements. In some embodiments, a rotating element comprises a wheel, a roller, a conveyor belt, or any combination thereof configured to provide movement of a base unit. A base unit, in some embodiments, comprises an arm. One end of an arm is configured to associate with the array of sensors. In some embodiments, a second end of an arm is configured to associate with the base unit, at for example a compartment 1405 or a surface. In some embodiments, an arm is adjustable. For example, an arm is extendible in length, such as a first portion of an arm that extends from a second portion of an arm. A base unit, in some embodiments, comprises wiring, such as one or more wires. Wiring is configured to associate with one or more sensors of an array, one or more power sources of the base unit, one or more computers of the base unit, or any combination thereof. A base unit, in some embodiments, comprises a shield, such as a disposable shield or a modular shield. In some embodiments, a shield is separate from a base unit. In some embodiments, a shield is associated with a base unit, such as attached to a base unit as a position that is proximal the array. In some embodiments, a shield is integral to the base unit. In some embodiments, a shield, an array, an arm, or any combination thereof is operatively connected (such as by wiring or wirelessly) to a controller or computer system.

Figure 15A:
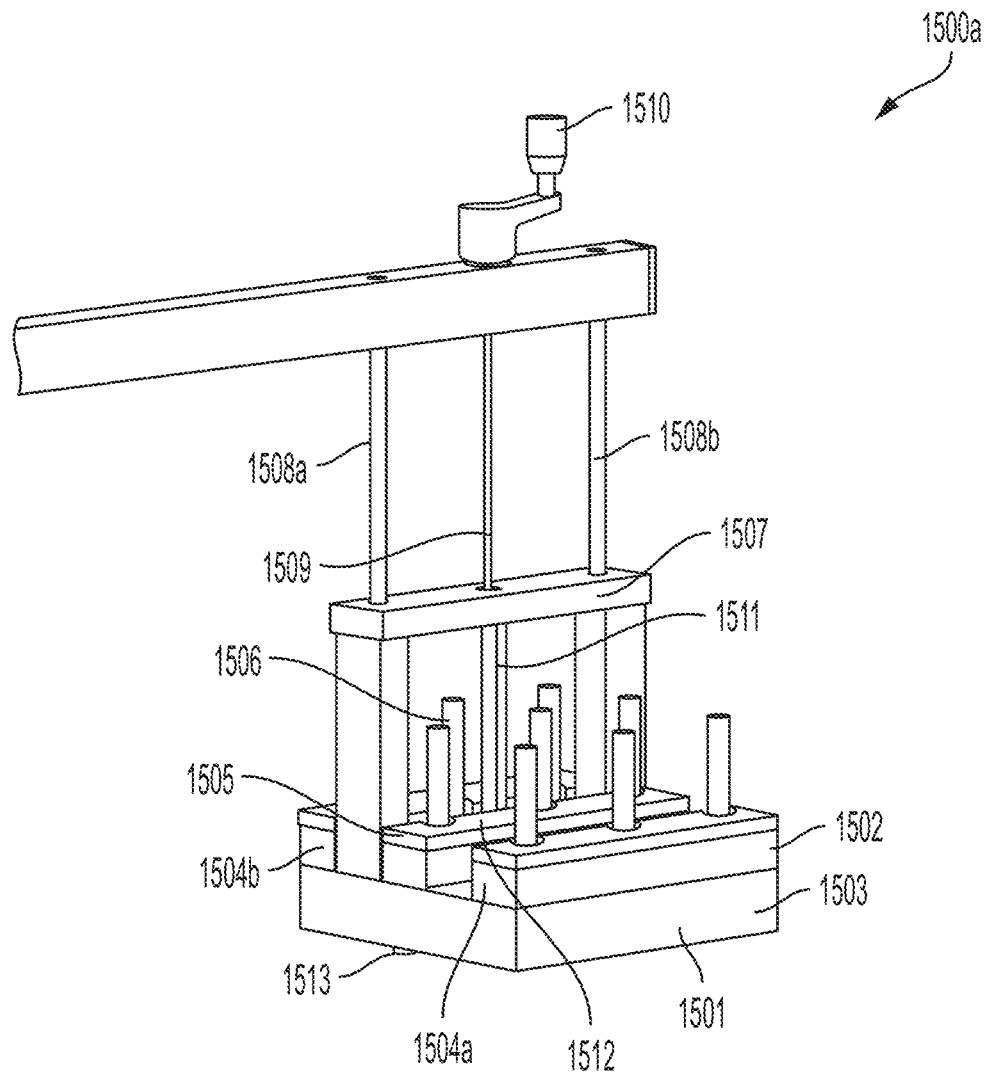
FIGS. 15A-C shows multiple view of a mobile cart device.

FIG. 15A is an enlarged view of one example of the sensor array 1500a. The sensor array, 1500a in some embodiments, comprises one or more sensor plates. For example, a sensor array 1500a, in some embodiments, comprises a bottom sensor plate 1501. In some embodiments, the bottom sensor plate 1501 is secured to other sensor components by one or more mounting bolts, such as 1, 2, 3, 4, 5, 6, 7, 8, 9, 10, 11 or 12 mounting bolts. The sensor array 1500a, in some embodiments, comprises a top sensor plate 1502. In some embodiments, the top sensor plate 1502 is secured to other sensor components by one or more mounting bolts, such as 1, 2, 3, 4, 5, 6, 7, 8, 9, 10, 11, or 12 mounting bolts. The sensor array 1500a, in some embodiments, comprises one or more sensor plate standoffs 1503. For example, a sensor array 1500a, in some embodiments, comprises 1, 2, 3, 4, 5, 6, 7, 8, 9, 10, 11 or 12 sensor plate standoffs.

A sensor array 1500a, in some embodiments, comprises one or more sensors 1506. In some embodiments, a sensor comprises a magnetometer sensor. A sensor, in some embodiments, comprises an optically pumped vector magnetometer or a zero field magnetometer. A sensor, in some embodiments, comprises a superconducting quantum interference device (SQUID), an inductive pickup coil, a vibrating sample magnetometer (VSM), a pulsed field extraction magnetometer, a torque magnetometer, a Faraday force magnetometer, an optical magnetometer, or any combination thereof. A sensor, in some embodiments, comprises a small-scale microelectricalmechanical (MEMS)-based magnetic field sensor.

In some embodiments, a sensor does not comprise a housing. In some embodiments, one or more sensors 1506 of a sensor array 1500a comprises one or more sensor housings 1504a or 1504b. For example, a sensor array 1500a, in some embodiments, comprises 1, 2, 3, 4, 5, 6, 7, 8, 9, 10, 11, 12, 13, 14, 15, 16, 17, 18, 19, 20, 21, 22, 23 or 24 sensor housings. In some embodiments, the sensor array 1500a comprises a sensor housing for each sensor in the array. In some embodiments, the sensor array 1500a comprises a sensor housing for at least every two sensors in the array. In some embodiments, a sensor housing is non-adjustable. In some embodiments, a sensor housing is movable within a sensor array unit to accommodate more than one sensor array configuration. In some embodiments, a sensor housing is secured in a location by one or more mounting bolts. In some embodiments, a sensor array 1500a is secured in a location by a sensor housing cap 1505.

In some embodiments, a sensor array 1500a comprises a handle 1510. In some embodiments, actuation of the handle 1510, such a rotational motion causes motion (such as linear motion) of the sensor array 1500a (i) away or towards an individual, (ii) away or towards an arm of the mobile cart device, or (iii) a combination thereof. The handle 1510 is operated manually. In some embodiments, actuation of the handle 1510 is automated. In some embodiments, when the handle 1510 is actuated, a screw 1509, such as a lead screw rotates. Rotation of the screw 1509, in some embodiments, permits one or more shafts on the sensor array to move.

A sensor, in some embodiments, comprises an element 1512 for coupling of two or more shafts 1508a or 1508b (such as shaft 1508a (such as a linear motion shaft) and shaft 1511 (such as a square motion transfer shaft), for transmission of motion (such as linear motion of the sensor array away or towards an individual). In some embodiments, the shaft also comprises a stopping element, such as a dog clutch. In some embodiments, the element 1512 is operatively coupled to the handle 1510, the screw 1509, one or more shafts such as shaft 1508a and shaft 1511, or any combination thereof.

A sensor array 1500a, in some embodiments, comprises a bracket 1507, such as a support bracket. In some embodiments, the bracket provides a spatial orientation for one or more shafts and one or more screws of the sensor array relative to one another. In some embodiments, a bracket is operatively coupled to a shaft 1508a, a shaft 1511, a screw 1509, an element 1512, or any combination thereof.

A sensor array 1500a, in some embodiments, comprises a stopper 1513, such as an individual stopper. In some embodiments, the stopper 1513 is configured to be positioned at a surface of an individual. In some embodiments, the stopper 1513 is configured to be positioned at a specified distance away from a surface of an individual. In some embodiments, the stopper 1513 is configured to prevent the sensor array from advancing beyond a specified position, such as beyond a surface of an individual. In some embodiments, a stopper 1513 is positioned on surface of the sensor array that when in operation is positioned closest to the subject.

Figure 15B:
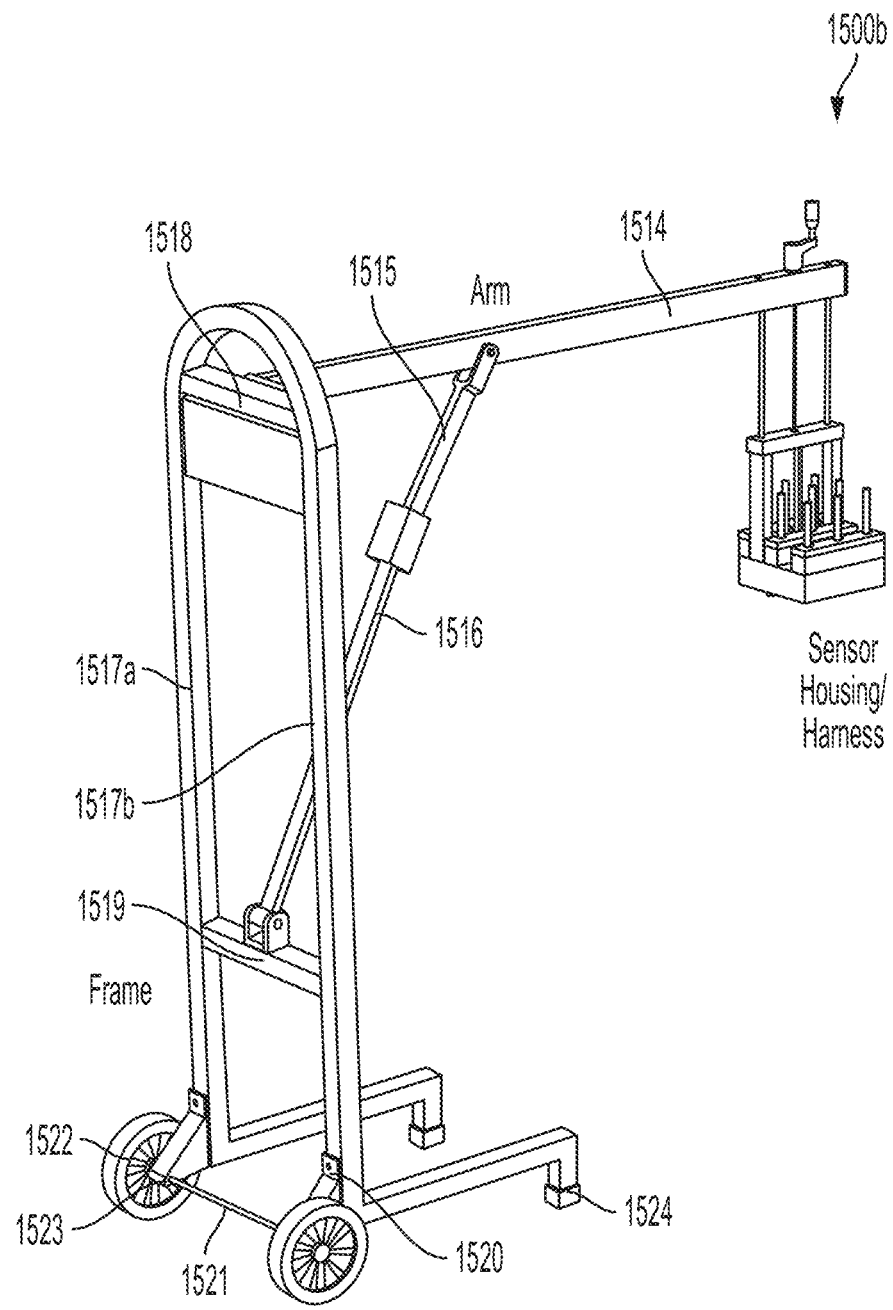

One example of a mobile cart device 1500b is shown in FIG. 15B. This example is similar to the example shown in FIG. 6 and FIG. 7. A mobile cart device 1500b, in some embodiments, comprises an arm 1514. The arm 1514, in some embodiments, comprises a first end and a second end. In some embodiments, a sensor array is coupled to the first end of the arm 1514. In some embodiments, an opposite end of the arm 1514 is coupled to a frame having a first supporting beam 1517a and a second support beam 1517b. In some embodiments, the opposite end of the arm 1514 is coupled to the frame at an upper bracket 1518 of the frame. In some embodiments, the mobile cart device 1500b comprises a second arm. In some embodiments, the second arm comprises a top support arm 1515 and a bottom support arm 1516. In some embodiments, at a location between a first end and second end of the arm 1514, a first end of a second arm is coupled to the arm 1514. In some embodiments, a second end of the second arm is coupled to the frame, such as coupled to the frame at a bracket 1519 (such as a locker bracket) of the frame. In some embodiments, the mobile cart device 1500b comprises one or more rotating elements, such as a wheel 1522. In some embodiments, a rotating element is operatively coupled to one or more axels 1521 (such as two rotating elements operatively coupled to a single axel), one or more bearings 1523, or a combination thereof, such that rotation of the two rotating elements occur in tandem. In some embodiments, the mobile cart device 1500b comprises two rotating elements. In some embodiments, the mobile cart device 1500b comprises one rotating element. In some embodiments, a rotating element is configured to move the mobile cart device 1500b from one location to a different location. A mobile cart device 1500b, in some embodiments, comprises an anchoring element 1524, such as a rubber foot, to anchor a mobile cart device 1500b at a desired location or to prevent further movement of the rotating element. A mobile cart device 1500b, in some embodiments, comprises one anchoring element. A mobile cart device 1500b, in some embodiments, comprises more than one anchoring element, such as two or three anchoring elements. One or more rotating elements, axels, anchoring elements, or any combination thereof is operatively coupled to the mobile cart device 1500b by one or more mounts 1520.

Figure 15C:
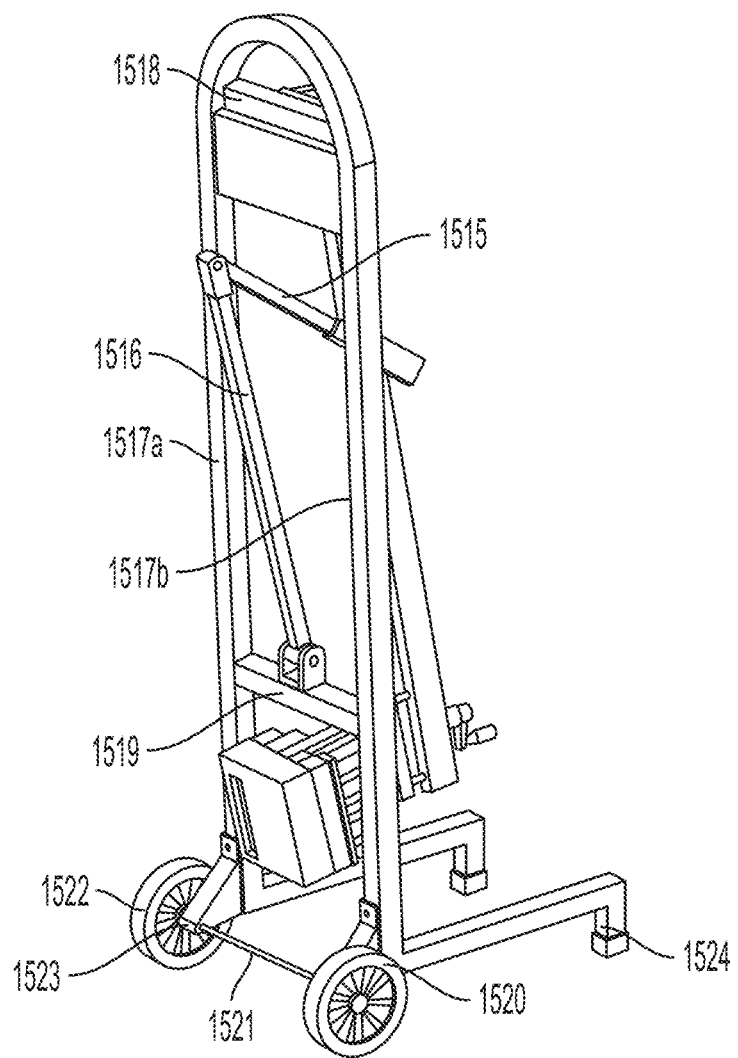

In some embodiments, a mobile cart device 1500b switches configuration from an extended configuration (FIG. 15B) to a closed configuration (FIG. 15C). In embodiments comprising an extended configuration, an arm 1514 is collapsed adjacent a frame, such that the mobile cart device is stored or easily moved to a different location.

In some embodiments, performance of a magnetometer is improved with equilibration. In these embodiments, a gradient of 1 nT/m is achieved within the shield. Equilibration, in some embodiments, comprises the process of degaussing.

In some embodiments, a shield configured for utilization of the equilibration process comprises an arrangement of coils. Typically the coils are arranged in one or more layers. In some embodiments, a shield comprises an inner coil layer and one or more outer coil layers, inner coils for an innermost layer and outer coils for each of the outer layers.

In some embodiments, the inner coils are (for 90 cm diameter of the cylinders) distributed in 45 degrees to effectively form 8 coils. The mechanical mounting precision is about +/−2 cm per wire. Many different configurations are acceptable for the outer coils generally. In some embodiments, a shield comprises 1 outer coil. In some embodiments, a shield comprises 2 outer coils. In some embodiments, a shield comprises 3 outer coils. In some embodiments, a shield comprises 4 outer coils. In some embodiments, a shield comprises 5 outer coils. In some embodiments, a shield comprises 6 outer coils. In some embodiments, a shield comprises 7 outer coils. In some embodiments, a shield comprises 8 outer coils. In some embodiments, a shield comprises 9 outer coils. In some embodiments, a shield comprises 10 outer coils.

In some embodiments, at least the inner layer must be electrically isolated. In some embodiments, ESD PVC is used instead of regular plastic just to avoid charge up effects, which disturb the magnetometers.

Figure 22:
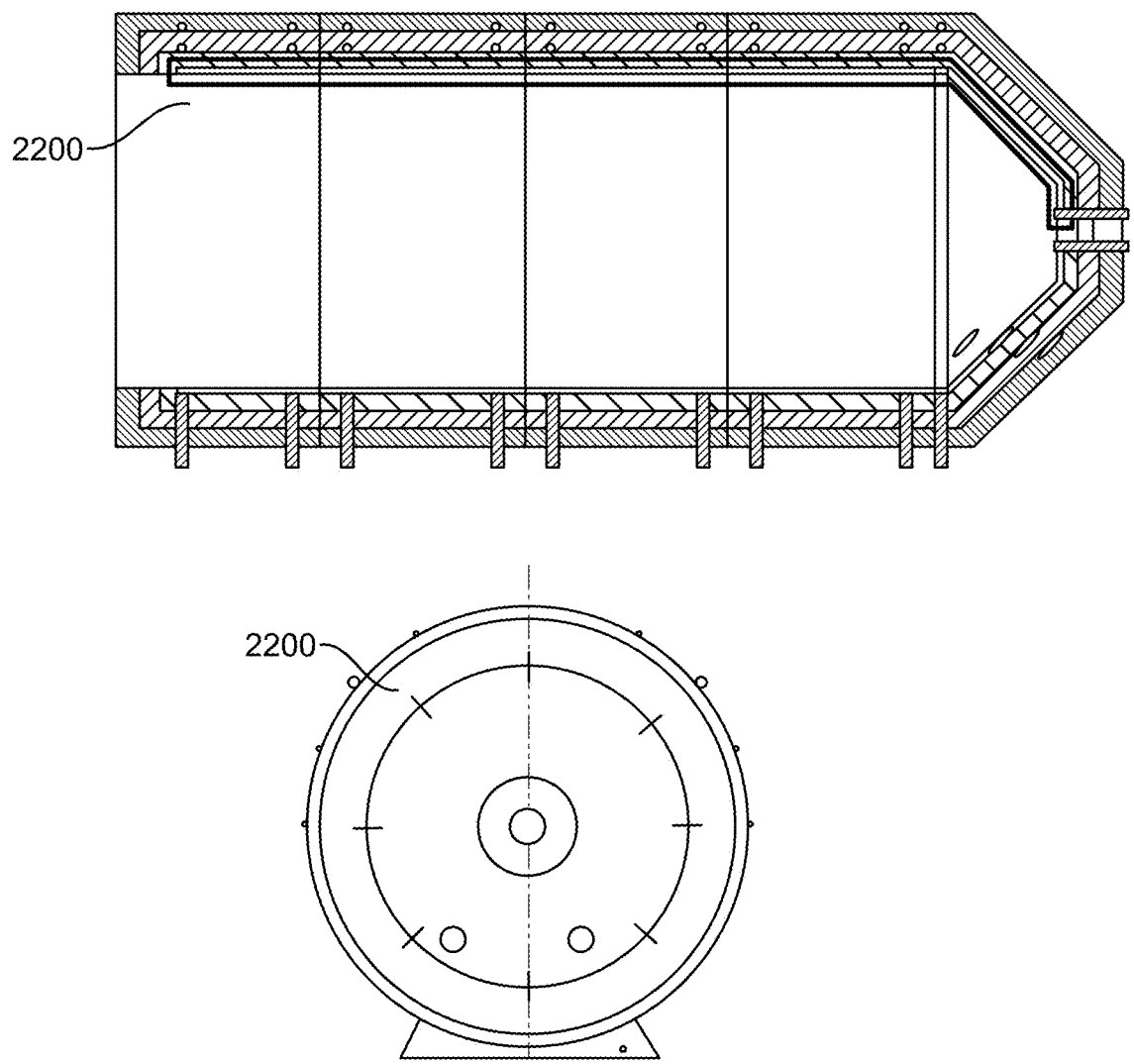
FIG. 22 shows an exemplary layout of one inner coil positioned in an embodiment of a shield.
Figure 23:
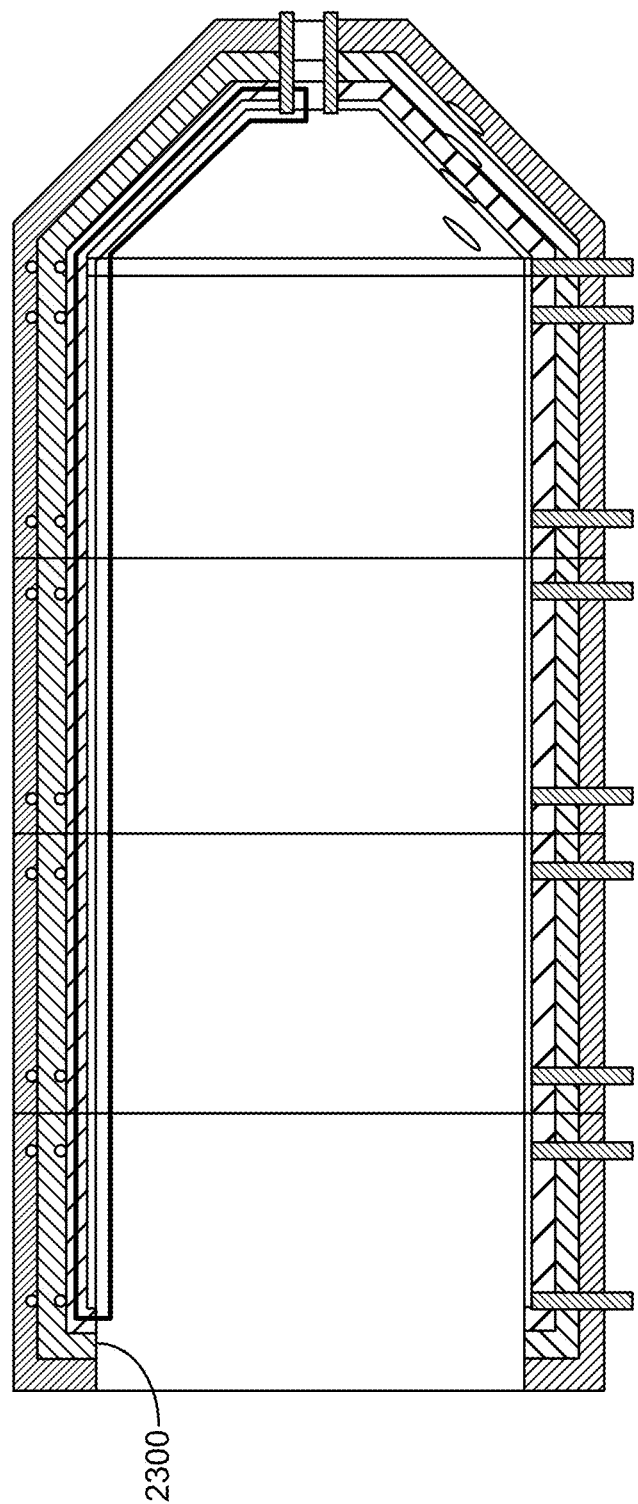
FIG. 23 shows an exemplary layout of outer coils positioned in an embodiment of a shield.

FIG. 22 shows an exemplary layout of one inner coil 2200 positioned in an embodiment of a shield. FIG. 23 shows an exemplary layout of outer coils 2300 positioned in an embodiment of a shield.

In some embodiments, a connection to an amplifier (or transformer) is opened during the measurements with the magnetic field probes. In some embodiments, this is achieved using a mechanical relay.

The wire dimensions are typically at least 2.5 mm2, but 4 mm2 would be preferable. I would suggest for the test device 3 turns at each 8th of the coil, resulting in 24 turns. I cannot estimate the permeability, but it should be comparable to Krupp Magnifer Material (which I am more used to). So the 24 turns would be about 1 Ohm and with 10 A saturation current, this gives 10 V..

In some embodiments, an equilibration sequence would be a 30 s sequence with linearly decreasing envelope, starting from saturation of the inner layer. This sequence is needed every time some large change in the field is applied. During regular operation I would guess 1-3 times a day would make sense. The outer shields must be equilibrated only once, when the shield is installed, or when the external fields change direction by 90 degrees or so, using the same amplifier. (Therefore, there must be a similar amount of turns for the coils, to use the same equipment).

In some embodiments, the coils for equilibration are individual wires with gold plated contacts. Due to magnetization issues, no Ni substrates or coatings can be used for connectors inside. In some embodiments, the required level of precision the equilibration coils of the outer shield can be placed randomly without special precautions, whereas the inner coils require at least a 6 fold symmetry for the distribution of the current to obtain a reasonably shaped residual field for 60 cm diameter and 8 for 1 m diameter. For the demonstrated project we chose connectors from brass with gold coating without a nickel intermediate layer (this is rare!) to avoid excessive magnetization. All connectors must be placed outside the inner shield layer. Their magnetization (on this level) is not relevant for the residual field inside.

Figure 24:
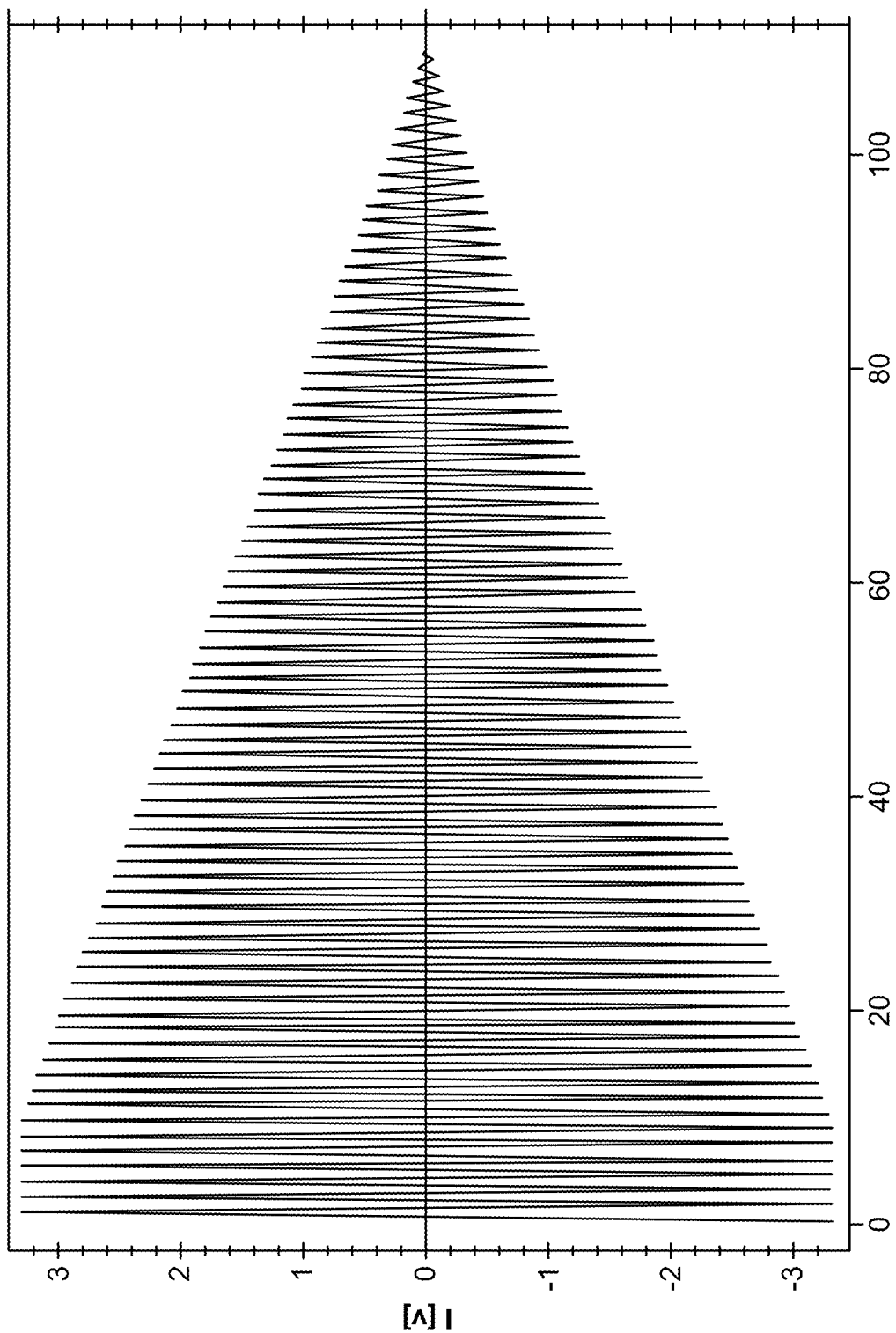
FIG. 24 shows a typical equilibration function.

An equilibration process employed in some embodiments of the shields described herein, is a process for bringing magnetizable material in an equilibrium with a surrounding magnetic field. In some embodiments, this is done by applying a sinusoidal current around a magnetizable material. The oscillation is extremely well centered around zero and is large enough to saturate the material in both directions. By decreasing the amplitude to zero, a very low magnetic field strength outside the magnetizable material (inside the cylinder) is obtained. For initial tests, a linearly decreasing envelope is useful, as it is a very reliable function. This model is programmed into the equilibration unit. An exponentially decreasing function may be advantageous in future. The pre-set function (which can be changed by the user on the PC) is shown below:

FIG. 24 shows a typical equilibration function. At the beginning, the maximum current is kept for 10 cycles and then decreased until zero amplitude is reached. Note that at the ultimate performance level, many options for changing and improvements are available.

In some embodiments, the equilibration coils are connected to the electrical equipment using twisted-pair cables. No RF shielding or other precautions are required, as higher frequencies are damped by the inductance of the shielding material and coil configuration (mH range).

In some embodiments, a computing device programs a sinusoidal function with envelope function, which is converted to a voltage signal by an NI 6281 data acquisition device. The voltage is fed to a voltage divider and then drives a power amplifier. The function can be set by the user and is programmable. The timing resolution of the curve is 10 kHz.

In some embodiments, inside the control box there is a box with potentiometers. These potentiometers can be adjusted manually to set the ratio of DAC voltage to current out of the amplifier. This minimizes any bit-size effects for the residual field (16 bit for 20 V=0.3 mV resolution). From experience, the optimization of this will be relevant for <0.5 nT residual fields. There are 2 potentiometers to tune different currents, they can then be selected via software. In case of a noisy environment, the voltage divider box is a useful place to add additional frequency filtering by a capacitor. In some embodiments, the band pass filtering of the amplifier will be sufficient for most applications.

In some embodiments, a power amplifier comprises a 4-quadrant amplifier which can be operated with large inductive loads and is intrinsically fail-safe against mistakes operation, e.g shortcuts, many inductive spikes etc.. For magnetic equilibration, the amplifier should be used in current-controlled mode, but can also be operated in any configuration. Due to extreme noise requirements, it is preferable to change the coils around the magnetizable material (cross section and number of turns) to match the maximum power of the amplifier. The power is chosen to be very small to achieve extremely low noise operation. Bandpass filters can be set manually on the front side to reduce noise effects. The amplifier can be fully remote controlled via a sub-d connector on the back side. A unique feature if this amplifier is the possibility to adjust the base-line by 1% via an analog +/−10 V input, independent of the signal input. In some embodiments, to perform DC measurements, the noise and the drift of the magnetic field probes is relevant. In some embodiments, two three-cannel Bartington Fluxgates type Mag03-IEL-70 with <6 pT noise-amplitude (peak-to-peak) are employed. Two electronics units supply three sensors each, with flying lead sensors with 5 m cable length each. In some embodiments, a readout of, for example, one or more fluxgates is done with a NI 628118-bit analog input unit to provide sufficient resolution of the fluxgate analog signals (+/−10 V). No voltage divider is required to match the range. The USB control is only for data transfer to the PC, the NI unit is independently grounded and has an independent power supply. In some embodiments, the readout rate is set up to 625.000 samples per second.

EXAMPLES

Non-limiting examples of embodiments and elements of embodiments of the devices and systems described herein are as follows:

A magnetically shielded environment: comprises minimum dimensions of about 7 foot width×about 7 foot depth×about 7 foot height. A magnetically shielded environment, in some embodiments, comprises a DC shielding factor of at least about 500 with minimum shielding factor of about 56 decibel (dB) from a bandwidth of from about 0.1 Hz to about 500 Hz at all points at least about 1 foot from each surface of a magnetically shielded environment.

A cart with a computer: is stationed outside of the magnetically shielded environment. Connected to the computer is a sensor's electronic control module, which is part of a supplied device. In some embodiments, each module provides power and control instructions to one sensor in the array, which is located on a device arm. Setup 1600 in an exemplary embodiment, appears as shown in FIG. 16.

Figure 16:
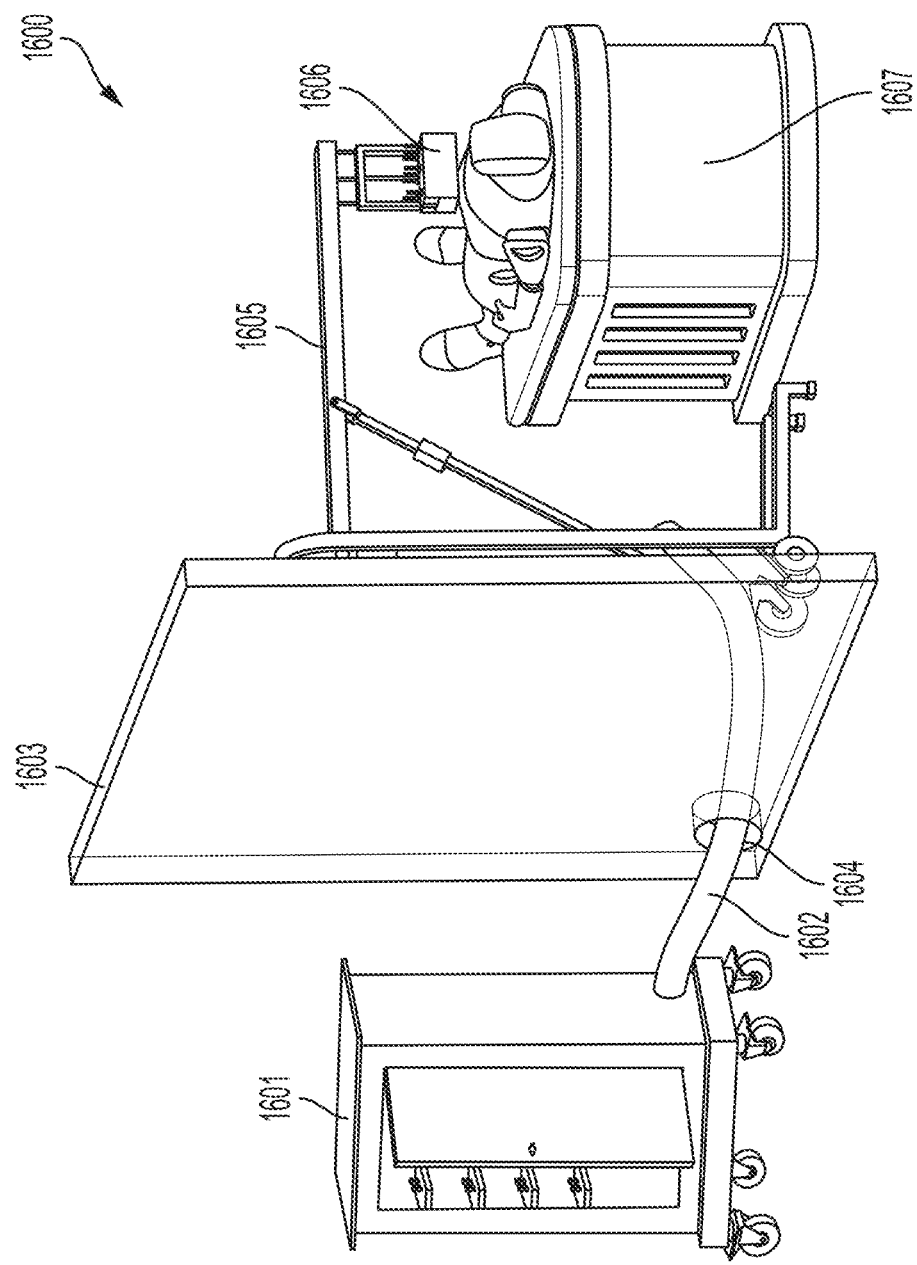
FIG. 16 shows one example of a device in use in a magnetically shielded environment.

As shown in FIG. 16, an individual lies in a supine position on a base unit (such as a bed) 1607. The sensor array 1606 is positioned adjacent to a location on the subject, such as adjacent to a chest position, by adjusting an arm 1605 of a mobile cart device. A shield 1603 is positioned between (i) the subject and sensor array 1606 and (ii) one or more additional devices 1601 such as an electrical device, a power supply, a computer, or any combination thereof. One or more subcomponents 1602 (such as wiring) that are needed to operatively connect the one or more additional devices and the sensor array 1606 is housed in a tubing or a covering. An opening 1604 in the shield 1603 is configured to accept the one or more subcomponents 1602 to pass there through.

Figure 17:
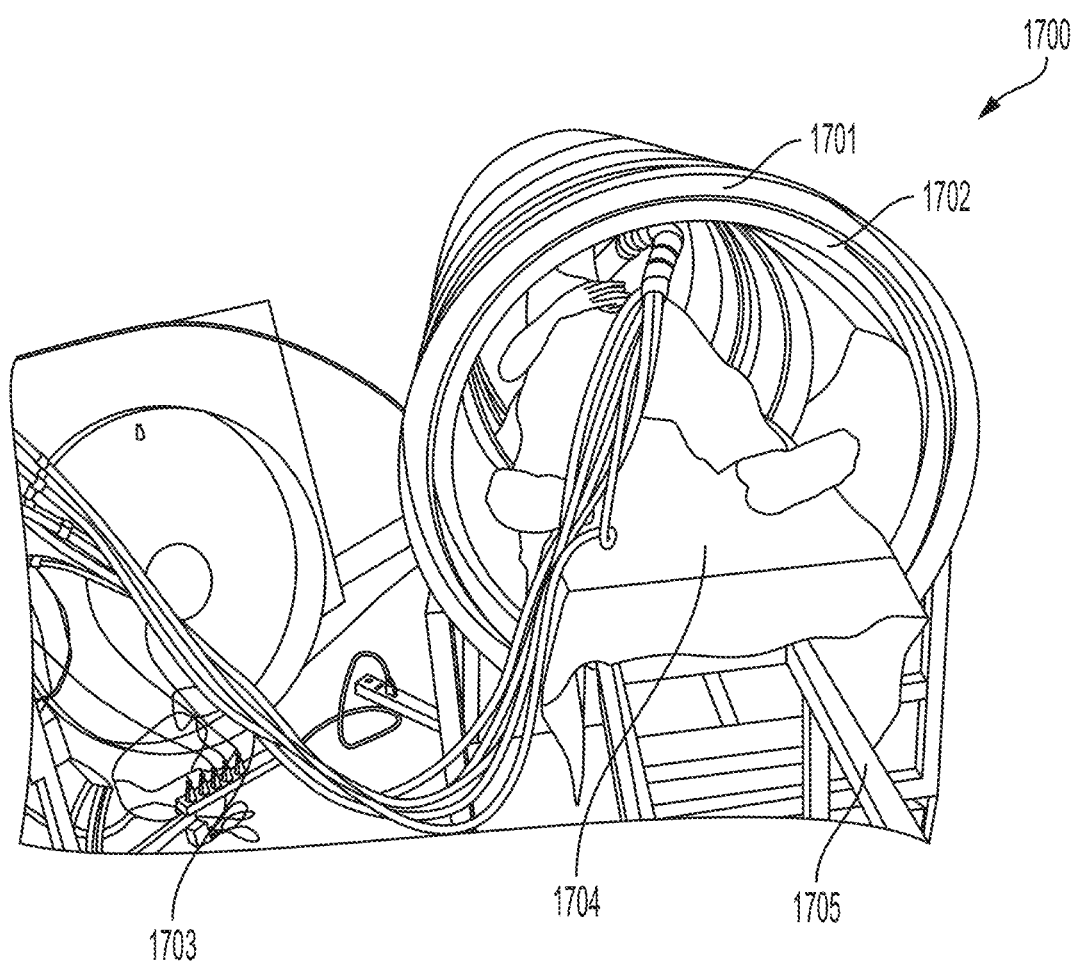
FIG. 17 shows an example of an individual sliding into a shield.

As shown in FIG. 17, a shield 1700, in some embodiments, comprises more than one layer, such as a first layer 1701 and a second layer 1702. In some embodiments, the first layer 1701 and second layer 1702 are adjacent to one another. In some embodiments, the first layer 1701 and second layer 1702 are separated by a spacing A base unit: (such as a patient bed), in some embodiments, is positioned within a magnetically shielded environment upon which an individual is positioned (such as lying supine) prior to device use. This bed is constructed of non-ferromagnetic materials (such as entirely constructed of non-ferromagnetic materials) and non-permanent magnets in order to minimize the amount of interference the device may read.

Setup: To setup a device for use, one or more of the following exemplary steps are carried out:

Ensure that device frame and sensor housing are located inside a magnetically shielded room. Keep a device in storage mode with a device's arm collapsed.

Ensure that the control units are connected to a sensor housing and a device frame through one or more portals of the magnetically shielded room.

Power on the computer interface and launch the software application (such as Maxwell).

Power on an Electronic Control Module.

Position an individual on a base unit 1704 (i.e. bed) with the individual's head aligned with one side of the base unit 1704 and the individual's feet aligned towards a second side of the base unit 1704, such as shown in FIG. 17. A magnetically shielded room has enough clearance to position a magnetocardiograph along at least one side of the base unit 1704.

An individual is positioned on a base unit 1704 that is configured such that at least a portion of the base unit 1704 is slidable into and out of a shield opening. The base unit 1704 is configured to slide on a track 1705 or may slide on one or more rollers or wheels. As least a portion of subcomponents 1703, such as a wiring, is configured to operatively connect the sensor array to one or more other devices, is configured to enter at least a portion of the shield 1700. Subcomponents 1703 are associated with a hook or latch or track structure within the shield 1700.

Extend an arm of the frame such that the arm makes about a 90 degree angle with a vertical portion of the frame with a handle (such as a curved handle).

Move the device towards the subject by pulling the handle on the frame. Position the device such that the sensor housing is above an area of interest on the subject (such as the chest area). Make small adjustments such that the square platform is put in an optimal position.

Align the housing on the individual's left side with the rightmost side of a sensor array platform on or proximally above and parallel to the individual's center line.

Use a lift mechanism at the end of the frame's arm to adjust a height of the sensor housing. The sensor housing is lowered to a location where rests on or proximally above an area of interest on the individual (e.g. chest). The handle is rotated in a first direction in order to lower the sensor housing. The handle is rotated in a second direction to raise the sensor housing.

Initiation: After a frame is in position, one or more sensors are activated to prepare for recording a signal, such as cardiac magnetic activity. To begin initiation, a user logs in to a software application (such as Maxwell) and selects the data acquisition module. If there is trouble with any of the steps below, the application is closed and attempts to reopen.

If a problem does not go away, the computer interface is rebooted. To initiate a device for use, one or more of the following is adhered to:

Ensure connection to all sensors (such as 8 sensors) exists by checking sensor status in the data acquisition software user interface.

Initiate the autostart procedure through the software application by pressing "autostart" in the data acquisition software user interfaces. This process calibrates one or more sensors for use. Before continuing, ensure that the readiness indicator found in the software UI has turned green and the status reads "ready".

Recording: After initiation is complete, the device is ready to capture a signal, such as a cardiac magnetic field data. To begin, one or more of the following is carried out:

Select the "acquire" button in the software application. Selecting this option plots the magnetic field collected from the sensors in a viewing window found on the acquisition software UI.

Ensure a collected magnetic field is characteristic of a signal, such as a cardiac electrical activity.

To save data to a file, select the "record" option. Select preferences for period length of data acquisition, file name, and file save location. Select "save" to begin saving to file. Application, in some embodiments, automatically cease saving after a selected amount of time that has elapsed. Files are named in accordance with institutional policy to protect subject identifying information.

Power-down and Storage: After device use is complete, the system is powered down by following one or more of the following:

Close the application on the computer.

Power off the electronic control modules by turning the toggle switch to the "off" position.

Power off the computer.

Within the magnetically shielded enclosure a handle of the device is rotated in a first direction to raise a sensor platform. A device is repositioned by pulling a handle (such as a curved handle) so that the arm does not intersect with the subject or base unit (such as a bed). The extension arm is moved downward towards the ground to return the device to a storage mode. The subject is assisted in rising from the base unit. The user, the subject, or a combination thereof has the magnetically shielded enclosure.

Example 2

Setup: To setup a device for use, one or more of the following exemplary steps are carried out:

Ensure that a device frame and a sensor housing are free of defects or damage.

Power on a computer interface and launch a software application.

Power on the Electronic Control Modules.

Pull out a base unit (such as a bed) from the magnetic shielding chamber until the bed is fully outside of the shielding chamber.

Ensure locking components of the sensor array and arm (such as an extension arm) are unlocked. Move the sensor array away from the base unit so that the sensor array or portion thereof is not above the base unit.

Assist an individual onto a surface of the base unit. Position the individual on the base unit with an individual's head aligned towards to opening of the bore and an individual's feet aligned towards the other, such as shown in FIG. 17.

Move the sensor array over an area of interest on the individual (such as an individual's chest).

Make adjustments such that a sensor array platform is positioned correctly. The housing is aligned on the subject's left side, with the rightmost side of the sensor array platform above and parallel to the subject's center line.

Lower the sensor array platform to adjust height of the sensor housing. Housing is lowered to a point where it may rest on or proximally above a position of interest on the subject (e.g. chest).

Lock pivots or joints or extension points of the sensor array to restrict motion of the array.

Slide the base unit into the recess opening of the shield until an external light on the device is indicated (such as turned on, or changed color such as turning green).

Initiation: After the frame is in position, one or more sensors are activated to prepare for recording a signal, such as a cardiac magnetic activity. To begin initiation, a logs in to a software application and selects the data acquisition module. If there is trouble with any of the steps below, the application is closed and attempts to reopen. If the problem does not go away, the computer interface is rebooted. To initiate a device for use, one or more of the following is carried out:

Ensure connection to one or more sensors (such as 8 sensors) exists by checking sensor status in the data acquisition software user interface.

Initiate the autostart procedure through the software application by pressing "autostart" in the data acquisition software user interface. This process calibrates one or more sensors for use. Before continuing, ensure that the readiness indicator found in the software UI has turned green and the status reads "ready".

Recording: After initiation is complete, the device is ready to capture a signal, such as a cardiac magnetic field data. To begin, one or more of the following is adhered to:

Select the "acquire" button in the software application. Selecting this option plots the magnetic field collected from the sensors in a viewing window found on the acquisition software UI.

Ensure one or more collected magnetic field is characteristic of a signal, such as a cardiac electrical activity.

To save the data to file, select the "record" option. Select preferences for period length of data acquisition, file name, and file save location. Select "save" to begin saving to file. Application automatically ceases saving after the selected amount of time has elapsed. Files are named in accordance with institutional policy to protect subject identifying information.

Power-down and Storage: After device use is complete, the system is powered down by following one or more of the following:

Close the application on the computer.

Power off the electronic control modules by turning the toggle switch to the "off" position.

Power off the computer.

The base unit (such as a bed) is moved out of the magnetic shielding chamber. One or more joints or pivots or extensions or combinations thereof of the sensor array or arm is unlocked and is moved away from the base unit such that the path of motion is out of an individual's way. The subject is assisted from leaving the base unit. One or more of the sensor arrays, sensor housing, an internal surface of a shield, a surface of a base unit, or any combination thereof is cleaned or sanitized between use of a first subject and a second subject.

Example 3

Setup: To setup device for use, one or more of the following exemplary steps is carried out:

Power on a computer interface and launch a software application.

Power on an Electronic Control Modules

Position an individual on a base unit (such as a standard hospital bed) with an individual's head aligned with one side of the base unit and individual's feet aligned towards a second side of the base unit, such as shown in FIG. 17. The room of operation having sufficient clearance to position a sensor array (such as a magnetocardiograph) along at least one side of the base unit.

Extend a device's arm and increase a height of the device by either pulling up on the arm or using the "raise/lower" button on a sensor array so that the sensor array is positioned above an individual.

Move the device towards the individual by pushing the mobile cart. Position the device such that the sensor housing is above the subject (such as above the subject's chest).

Use a lift mechanism at an end of a frame's arm to adjust a height of the sensor housing. A sensor housing is lowered to the position where it rests on or proximally above the position (such as an individual's chest) at the point of normal subject inhalation.

Make adjustments such that the sensor array platform is positioned correctly. The housing is aligned on the subject's left side, with the rightmost side of the sensor array platform above and parallel to the subject's center line.

Initiation: After the frame is in a position, one or more sensors are activated to prepare for recording a signal, such as a cardiac magnetic activity. To begin initiation, a user logs in to a software application and selects the data acquisition module. If there is trouble with any of the steps below, the application is closed and is attempted to reopen. If the problem does not go away, the computer interface is rebooted. To initiate a device for use, one or more of the following is carried out:

Ensure connection to one or more sensors (such as 8 sensors) exists by checking sensor status in the data acquisition software user interface.

Initiate the autostart procedure through the software application by pressing "autostart" in the data acquisition software user interfaces. This process calibrates one or more sensors for use. Before continuing, ensure that the readiness indicator found in the software UI has turned green and the status reads "ready".

Recording: After initiation is complete, the device is ready to capture a signal, such as a cardiac magnetic field data. To begin, one or more of the following is carried out:

Select the "acquire" button in the software application. Selecting this option plots the magnetic field collected from the sensors in a viewing window found on the acquisition software UI Ensure one or more collected magnetic fields are characteristic of a signal, such as a cardiac electrical activity.

To save the data to file, select the "record" option. Select preferences for period length of data acquisition, file name, and file save location. Select "save" to begin saving to file. Application automatically ceases saving after the selected amount of time has elapsed. Files are named in accordance with institutional policy to protect subject identifying information.

Power-down and Storage: After device use is complete, the system is powered down by following one or more of the following:

Close the application on the computer.

Power off the electronic control modules by turning the toggle switch to the "off" position.

Power off the computer.

The device's arm is raised by pushing up on the arm or using a "raise/lower" button on the sensor array so that the sensor array is above the subject's chest level. The subject is assisted in rising from the base unit.

Example 4

Figure 18:
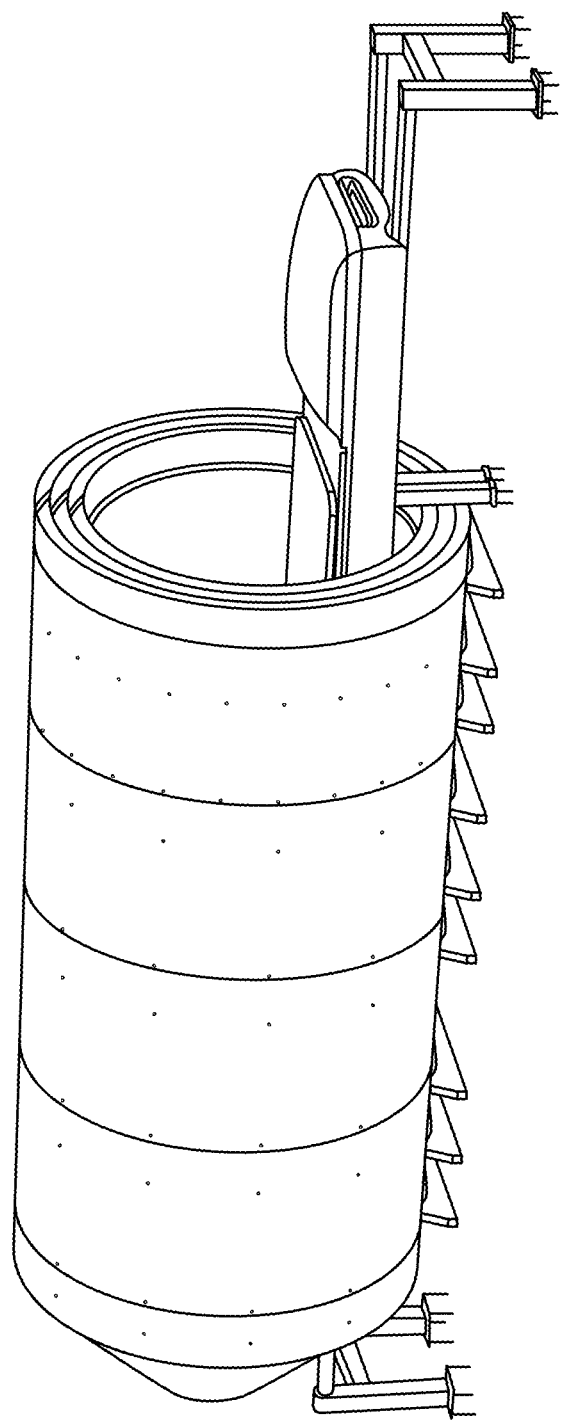
FIG. 18 shows an example of an embodiment of a shield comprising three layers of mu-metal (three innermost layers) and one layer of aluminum alloy (outer layer).

FIG. 18 shows an example of an embodiment of a shield comprising three layers of mu-metal (three innermost layers) and one layer of aluminum alloy (outer layer). The truncated end to the left and the open end to the right. Although one end of the shielding cylinder is completely open, if the sensor assembly is located far enough from this open end, the EM noise entering the shield bore through the open end will decay to a level low enough so as not to affect the accuracy of any magnetic fields measurements taken from an individual positioned within the shield.

Figure 19:
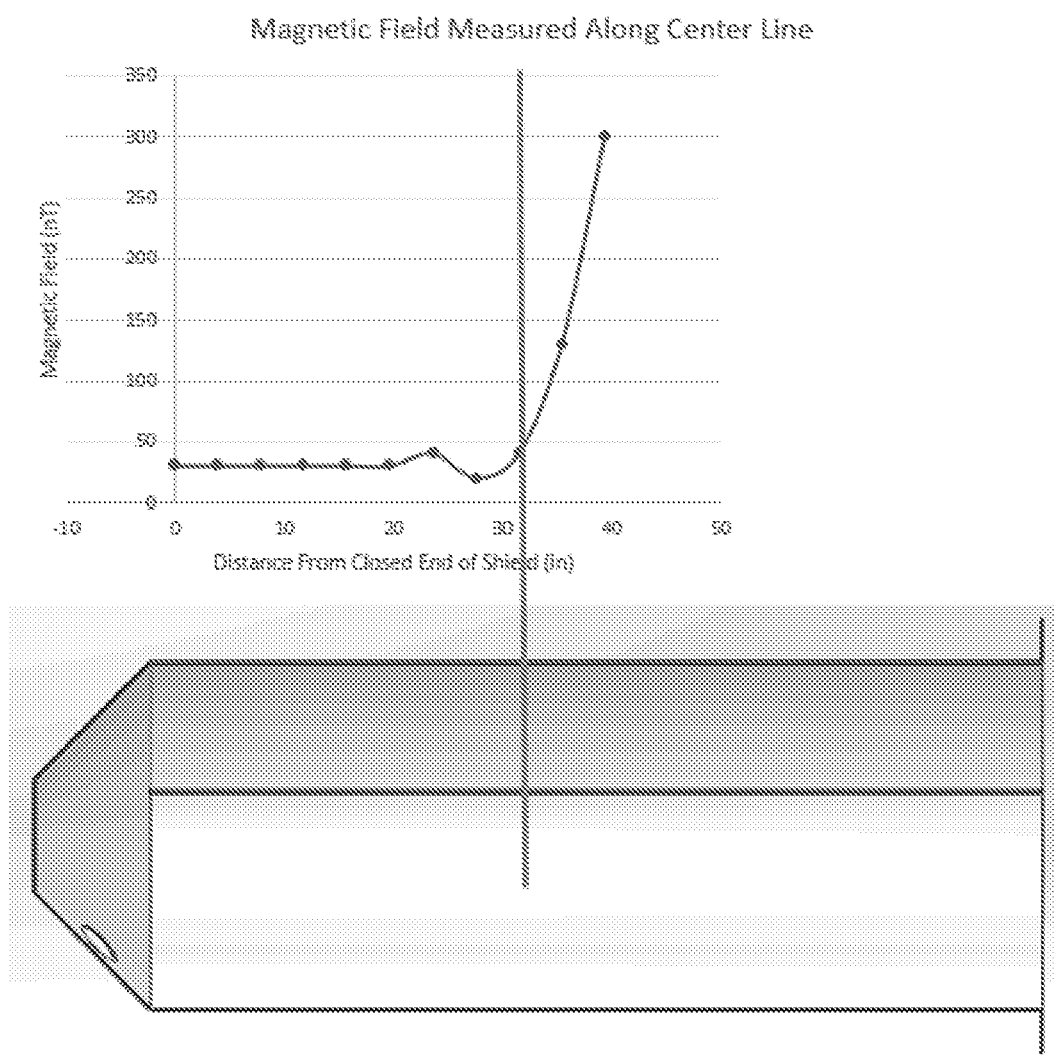
FIG. 19 shows a plot of magnetic field measurements along the centerline of a shield.

FIG. 19 shows a plot of magnetic field measurements along the centerline of a shield such as the one shown in FIG. 18. Field levels less than 50 nT are acceptable for system operation. The decay of ambient noise has been measured and is shown in FIG. 19. Since the head of a patient will be positioned roughly at the point where the cylinder begins to taper, the location of, for example, an organ of interest such as, for example, the heart of an individual, within the EM shield can be expected to lie comfortably within a level of background noise (<50 nT) deemed acceptable for reliable device performance.

Example 5

Figure 20:
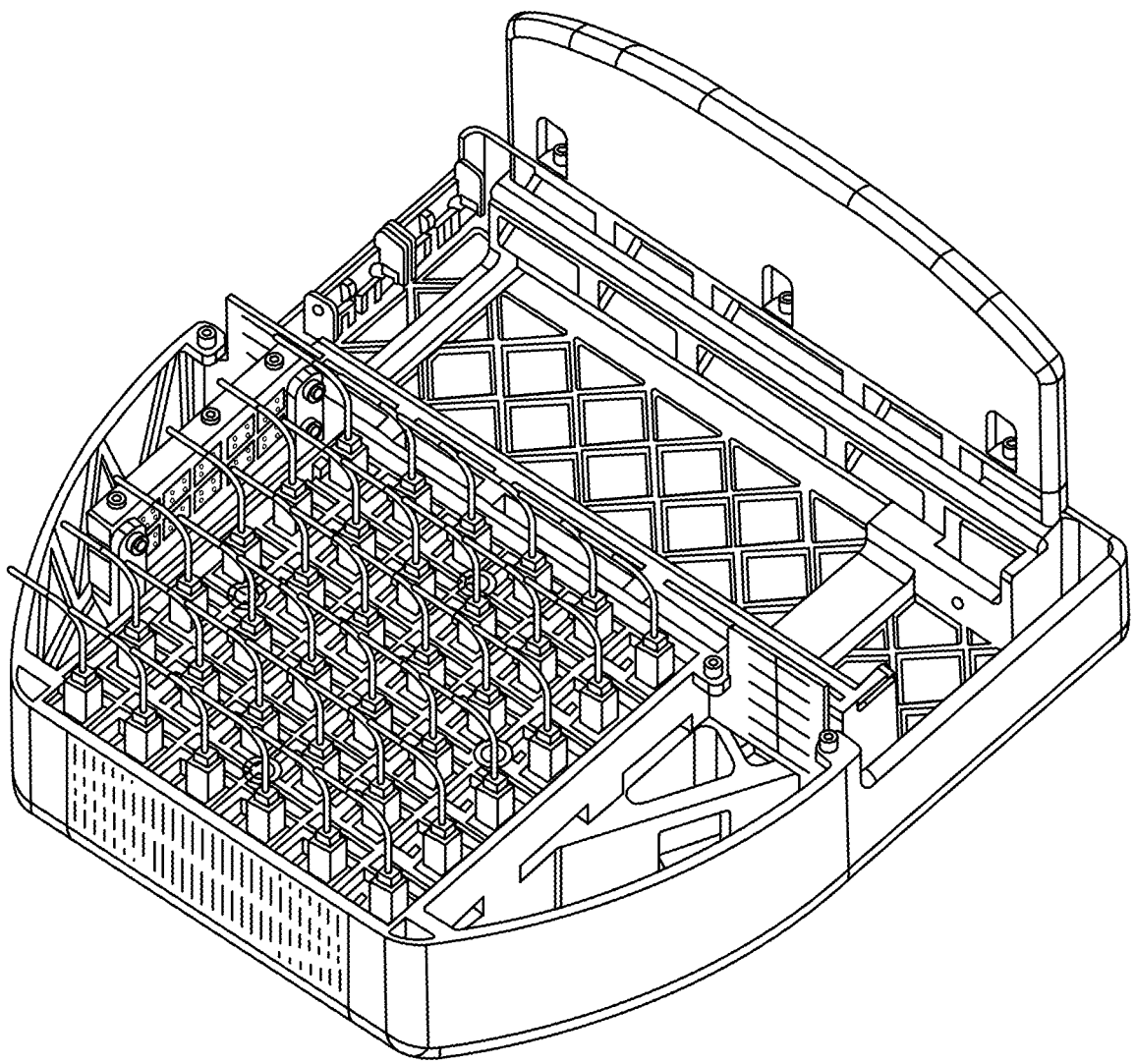
FIG. 20 shows an example of a sensor array.

FIG. 20 shows an example of a sensor array (sensors shown in black, cables cut for clarity). For precise positioning of this sensor array above the patient's heart, the housing can be raised, lowered and translated in a transverse direction (shoulder to shoulder) via a manually operated gear mechanism.

Figure 21:
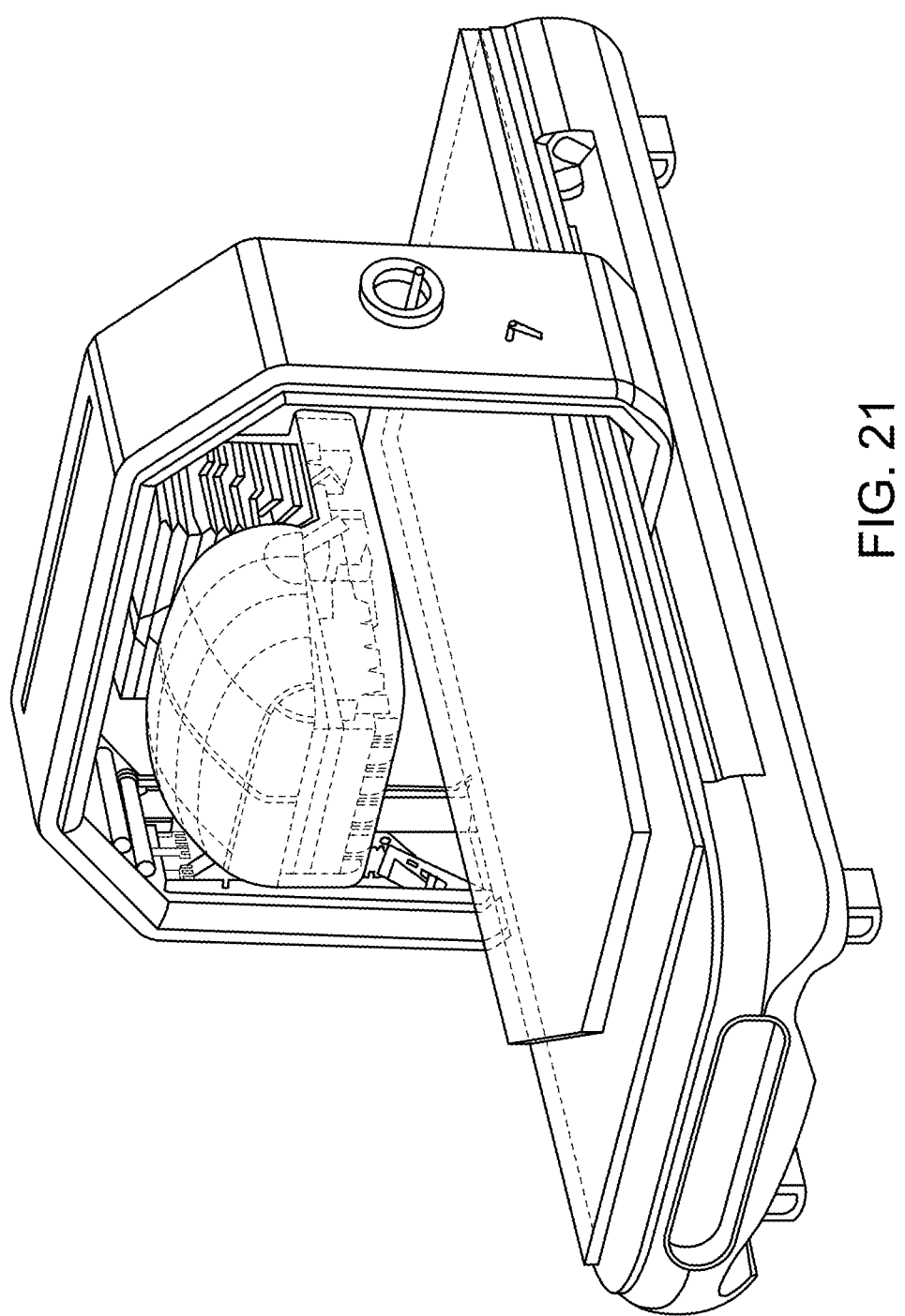
FIG. 21 shows an example of a 3D rendering of a sensor head cage mounted on a bed of a shield.

FIG. 21 shows an example of a 3D rendering of a sensor head cage mounted on a bed of a shield such as the shield of FIG. 18 (the patient's head would be on the left, chest underneath the arch within the shield).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein is employed in practicing the invention. It is intended that the following claims define the scope of the invention and that methods and structures within the scope of these claims and their equivalents be covered thereby.

What is claimed is:

1. A device for sensing a magnetic field associated with an individual, comprising:
   a. a movable base unit;
   b. an arm having a proximal end and a distal end, the proximal end being coupled to the movable base unit by a first joint, the first joint configured so that the arm moves relative to the movable base unit with at least one degree of freedom;
   c. an array of one or more optically pumped magnetometers coupled to the distal end of the arm, the array of the one or more optically pumped magnetometers configured to sense the magnetic field associated with the individual, wherein the array of the one or more optically pumped magnetometers is configured to be arranged to conform to at least a portion of a chest of the individual; and
   d. a non-transitory computer-readable medium encoded with a computer program comprising instructions executable by a processor, the instructions configured to cause the processor to:
      i. receive the sensed magnetic field; and
      ii. determine a condition of the individual based on the sensed magnetic field,
      wherein the device is coupled to a shield configured to shield the device from one or more environment magnetic fields, the shield comprising coils arranged in one or more layers.

2. The device of claim 1, wherein the shield is configured to at least partially enclose a portion of a body of the individual.

3. The device of claim 2, wherein the portion of the body of the individual is at least a portion of a chest of the individual.

4. The device of claim 1, wherein the shield comprises two or more layers.

5. The device of claim 4, wherein each of the two or more layers has a thickness of from 0.1 to 10 millimeters.

6. The device of claim 1, wherein the shield comprises a permalloy or a mumetal.

7. The device of claim 1, wherein the arm comprises a proximal segment and a distal segment, and wherein a second joint is positioned between the proximal segment and the distal segment, the second joint configured so that the distal segment articulates relative to the proximal segment.

8. The device of claim 1, wherein the array of the one or more optically pumped magnetometers is movably coupled to the distal end of the arm so that the array of the one or more optically pumped magnetometers moves relative to the arm with at least one degree of freedom.

9. The device of claim 1, wherein the array of the one or more optically pumped magnetometers comprises at least three optically pumped magnetometers configured to be arranged to match a generalized contour of the at least the portion of the chest of the individual.

10. The device of claim 1, wherein the computer program comprises instructions configured to cause the processor to further filter the sensed magnetic field.

11. The device of claim 10, wherein the computer program comprises instructions configured to cause the processor to further filter the sensed magnetic field by cancelling out a magnetic field sensed by a gradiometer or subtracting a frequency-based measurement from the sensed magnetic field.

12. The device of claim 1, wherein the computer program comprises instructions configured to cause the processor to further generate a visual representation of the sensed magnetic field comprising a waveform.

13. The device of claim 1, wherein the condition comprises a diagnosis of the individual or a prognosis of the individual.

14. The device of claim 1, wherein the condition relates to a cardiovascular system of the individual.

15. A method for sensing a magnetic field associated with an individual, comprising:
   a. using a shield to at least partially enclose a portion of a body of the individual, the shield comprising coils arranged in one or more layers;
   b. positioning a mobile electromagnetic sensing device within proximity to the individual;
   c. positioning an arm of the mobile electromagnetic sensing device that is coupled to an array of one or more optically pumped magnetometers, such that the array of the one or more optically pumped magnetometers is configured to be arranged to conform to at least a portion of a chest of the individual;
   d. using the array of the one or more optically pumped magnetometers to sense the magnetic field associated with the individual; and
   e. determining a condition of the individual based on the sensed magnetic field using a computing device.

16. The method of claim 15, wherein the method further comprises shielding the mobile electromagnetic sensing device from one or environmental magnetic fields using the shield.

17. The method of claim 15, wherein the portion of the body of the individual is at least a portion of a chest of the individual.

18. The method of claim 15, wherein the shield comprises two or more layers.

19. The method of claim 18, wherein each of the two or more layers has a thickness of from 0.1 to 10 millimeters.

20. The method of claim 15, wherein the shield comprises a permalloy or a mumetal.

21. The method of claim 15, wherein the arm comprises a proximal segment and a distal segment, and wherein a second joint is positioned between the proximal segment and the distal segment, the second joint configured so that the distal segment articulates relative to the proximal segment.

22. The method of claim 15, wherein the array of the one or more optically pumped magnetometers is movably coupled to the distal end of the arm so that the array of one or more optically pumped magnetometers moves relative to the arm with at least one degree of freedom.

23. The method of claim 15, wherein the array of the one or more optically pumped magnetometers comprises at least three optically pumped magnetometers is configured to be arranged to match a generalized contour of the at least the portion of the chest of the individual.

24. The method of claim 15, wherein determining the condition of the individual based on the sensed magnetic field comprises filtering the magnetic field using the computing device.

25. The method of claim 24, wherein the filtering comprises cancelling out a magnetic field sensed by a gradiometer or subtracting a frequency-based measurement from the sensed magnetic field, using the computing device.

26. The method of claim 24, further comprising generating a visual representation of the magnetic field comprising a waveform using the computing device.

27. The method of claim 15, wherein the condition comprises a diagnosis of the individual or a prognosis of the individual.

28. The method of claim 15, wherein the condition relates to a cardiovascular system of the individual.

29. The device of claim 1, wherein the array of the one or more optically pumped magnetometers is configured to be arranged to conform to the at least the portion of the chest of the individual without contacting the individual.

30. The method of claim 15, wherein the array of the one or more optically pumped magnetometers is configured to be arranged to conform to the at least the portion of the chest of the individual without contacting the individual.

31. The method of claim 1, wherein the one or more layers of coils comprise one inner coil layer and one or more outer coil layers, wherein the inner coil layer is isolated from the one or more outer coil layers.

32. The method of claim 31, wherein coils in the inner coil layer are distributed in 45 degrees to effectively form a predefined number of coils.

33. The method of claim 31, wherein the coils in the inner coil layer are organized with at least a 6 fold symmetry.

34. The method of claim 1, wherein the coils comprise individual wires with gold plated contacts.

35. The method of claim 1, wherein a connection to an amplifier is opened when the optically pumped magnetometers sense the magnetic field associated with the individual.

* * * * *